United States Patent
Mahmoud et al.

(10) Patent No.: US 11,813,239 B2
(45) Date of Patent: Nov. 14, 2023

(54) COMPOSITIONS AND METHODS FOR IMPROVING CARDIAC STRUCTURE AND/OR FUNCTION

(71) Applicant: Wisconsin Alumni Research Foundation, Madison, WI (US)

(72) Inventors: Ahmed I Mahmoud, Middleton, WI (US); Jiyoung Bae, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 112 days.

(21) Appl. No.: 17/177,976

(22) Filed: Feb. 17, 2021

(65) Prior Publication Data

US 2021/0251938 A1    Aug. 19, 2021

Related U.S. Application Data

(60) Provisional application No. 62/978,243, filed on Feb. 18, 2020.

(51) Int. Cl.
*A61K 31/225* (2006.01)
*A61K 31/4412* (2006.01)
*A61P 9/04* (2006.01)

(52) U.S. Cl.
CPC ........ *A61K 31/225* (2013.01); *A61K 31/4412* (2013.01); *A61P 9/04* (2018.01)

(58) Field of Classification Search
CPC ...... A61K 31/4412; A61K 31/225; A61P 9/04
See application file for complete search history.

(56) References Cited

U.S. PATENT DOCUMENTS

| 2015/0065556 A1* | 3/2015 | Birsoy | A01K 67/0276 435/6.12 |
| 2017/0135977 A1* | 5/2017 | Chouchani | A61P 3/10 |

OTHER PUBLICATIONS

Xu et. al. (Neuroscience (2018) 393:24-32). (Year: 2018).*
Valls-Lacalle et. al. (Cardiovascular Research (2016) 109:374-384). (Year: 2016).*
Antico Arciuch VG, Elguero ME, Poderoso JJ and Carreras MC. Mitochondrial regulation of cell cycle and proliferation. Antioxid Redox Signal. 2012;16:1150-80.
Aurora AB, Porrello ER, Tan W, Mahmoud AI, Hill JA, Bassel-Duby R, Sadek HA and Olson EN. Macrophages are required for neonatal heart regeneration. J Clin Invest. 2014;124:1382-92.
Bajpai G, Bredemeyer A, Li W, Zaitsev K, Koenig AL, Lokshina I, Mohan J, Ivey B, Hsiao HM, Weinheimer C, Kovacs A, Epelman S, Artyomov M, Kreisel D and Lavine KJ. Tissue Resident CCR2– and CCR2+ Cardiac Macrophages Differentially Orchestrate Monocyte Recruitment and Fate Specification Following Myocardial Injury. Circ Res. 2019;124:263-278.
Bassat E, Mutlak YE, Genzelinakh A, Shadrin IY, Baruch Umansky K, Yifa O, Kain D, Rajchman D, Leach J, Riabov Bassat D, Udi Y,
Sarig R, Sagi I, Martin JF, Bursae N, Cohen S and Tzahor E. The extracellular matrix protein agrin promotes heart regeneration in mice. Nature. 2017;547:179-184.
Becker RO, Chapin S and Sherry R. Regeneration of the ventricular myocardium in amphibians. Nature. 1974;248:145-7.
Bryant DM, OMeara CC, Ho NN, Gannon J, Cai L and Lee RT. A systematic analysis of neonatal mouse heart regeneration after apical resection. JMol Cell Cardiol. 2015;79:315-8.
B van de Water, JP Zoeteweij, HJ de Bont, JF Nagelkerke. Inhibition of succinate:ubiquinone reductase and decrease of ubiquinol in nephrotoxic cysteine S-conjugate-induced oxidative cell injury. Mol Pharmacol. Nov. 1995;48(5):928-37.
Cai W, Zhang J, de Lange WJ, Gregorich ZR, Karp H, Farrell ET, Mitchell SD, Tucholski T, Lin Z, Biermann M, McIlwain SJ, Ralphe JC, Kamp TJ and Ge Y. An Unbiased Proteomics Method to Assess the Maturation of Human Pluripotent Stem Cell-Derived Cardiomyocytes. CircRes. 2019;125:936-953.
Chen Q, Vazquez EJ, Moghaddas S, Hoppel CL and Lesnefsky EJ. Production of reactive oxygen species by mitochondria: central role of complex III. J Biol Chem. 2003;278:36027-31.
Chouchani ET, Pell VR, Gaude E, Aksentijevic D, Sundier SY, Robb EL, Logan A, Nadtochiy SM, Ord ENJ, Smith AC, Eyassu F, Shirley R, Hu CH, Dare AJ, James AM, Rogatti S, Hartley RC, Eaton S, Costa ASH, Brookes PS, Davidson SM, Duchen MR, Saeb-Parsy K, Shattock MJ, Robinson AJ, Work LM, Frezza C, Krieg T and Murphy MP. Ischaemic accumulation of succinate controls reperfusion injury through mitochondrial ROS. Nature. 2014;515:431-435.
Chouchani ET, Methner C, Nadtochiy SM, Logan A, Pell VR, Ding S, James AM, Cocheme HM, Reinhold J, Lilley KS, Partridge L, Feamley IM, Robinson AJ, Hartley RC, Smith RA, Krieg T, Brookes PS and Murphy MP. Cardioprotection by S-nitrosation of a cysteine switch on mitochondrial complex I. Nat Med. 2013;19:753-9.
Das S, Goldstone AB, Wang H, Farry J, D'Amato G, Paulsen MJ, Eskandari A, Hironaka CE, Phansalkar R, Sharma B, Rhee S, Shamskhou EA, Agalliu D, de Jesus Perez V, Woo YJ and Red-Horse K. A Unique Collateral Artery Development Program Promotes Neonatal Heart Regeneration. Cell. 2019;176:1128-1142 e18.

(Continued)

*Primary Examiner* — Marcos L Sznaidman
(74) *Attorney, Agent, or Firm* — Daniel A. Blasiole; DeWitt LLP

(57) ABSTRACT

Compositions and methods for improving cardiac structure and/or function in subjects in need thereof. The methods include administering to a subject a succinate dehydrogenase inhibitor in an amount and for a time effective to elicit an improvement in cardiac structure and/or function. The subjects include subjects suffering from cardiac damage, such as damage resulting from myocardial infarction or other cardiac events. Improvements in cardiac function include one or more of an increase in cardiomyocyte proliferation, an increase in ejection fraction, an increase in fractional shortening, a decrease in left ventricle internal diameter diastole, and a decrease in left ventricle internal diameter systole. Improvements in cardiac structure include one or more of decreased fibrosis, an increase in myocardial thickness, an increase in coronary artery formation, an increase in capillary density, an increase in revascularization, and a decrease in myocardial lesion size. Compositions for performing the methods are provided.

19 Claims, 43 Drawing Sheets
(43 of 43 Drawing Sheet(s) Filed in Color)

(56) References Cited

OTHER PUBLICATIONS

De Bock K, Georgiadou M, Schoors S, Kuchnio A, Wong BW, Cantelmo AR, Quaegebeur A, Ghesquiere B, Cauwenberghs S, Eelen G, Phng LK, Betz I, Tembuyser B, Brepoels K, Welti J, Geudens I, Segura I, Cruys B, Bifari F, Decimo I, Blanco R, Wyns S, Vangindertael J, Rocha S, Collins RT, Munck S, Daelemans D, Imamura H, Devlieger R, Rider M, Van Veldhoven PP, Schuit F, Bartrons R, Hofkens J, Fraisl P, Telang S, Deberardinis RJ, Schoonjans L, Vinckier S, Chesney J, Gerhardt H, Dewerchin M and Carmeliet P. Role of PFKFB3-driven glycolysis in vessel sprouting. Cell. 2013;154:651-63.

Dhital KK, Iyer A, Connellan M, Chew HC, Gao L, Doyle A, Hicks M, Kumarasinghe G, Soto C, Dinale A, Cartwright B, Nair P, Granger E, Jansz P, Jabbour A, Kotlyar E, Keogh A, Hayward C, Graham R, Spratt P and Macdonald P. Adult heart transplantation with distant procurement and ex-vivo preservation of donor hearts after circulatory death: a case series. Lancet. 2015;385:2585-91.

Dikalov SI and Harrison DG. Methods for detection of mitochondrial and cellular reactive oxygen species. Antioxid Redox Signal. 2014;20:372-82.

Eelen G, de Zeeuw P, Simons M and Carmeliet P. Endothelial cell metabolism in normal and diseased vasculature. Circ Res. 2015;116:1231-44.

Fathollahipour S, Patil PS and Leipzig ND. Oxygen Regulation in Development: Lessons from Embryogenesis towards Tissue Engineering. Cells Tissues Organs. 2018;205:350-371.

Flink IL. Cell cycle reentry of ventricular and atrial cardiomyocytes and cells within the epicardium following amputation of the ventricular apex in the axolotl, Amblystoma mexicanum: confocal microscopic immunofluorescent image analysis of bromodeoxyuridine labeled nuclei. Anat Embryol (Berl). 2002;205:235-44.

Gertz EW, Wisneski JA, Stanley WC and Neese RA. Myocardial substrate utilization during exercise in humans. Dual carbon-labeled carbohydrate isotope experiments. J Clin Invest. 1988;82:2017-25.

Gonzalez-Rosa JM, Sharpe M, Field D, Soonpaa MH, Field LJ, Burns CE and Burns CG. Myocardial Polyploidization Creates a Barrier to Heart Regeneration in Zebrafish. Dev Cell. 2018;44:433-446 e7.

Gottlieb E and Tomlinson IP. Mitochondrial tumour suppressors: a genetic and biochemical update. Nat Rev Cancer. 2005;5:857-66.

Harris SP, Bartley CR, Hacker TA, McDonald KS, Douglas PS, Greaser ML, Powers PA and Moss RL. Hypertrophic cardiomyopathy in cardiac myosin binding protein-C knockout mice. Circ Res. 2002;90:594-601.

Hashimoto H, Olson EN and Bassel-Duby R. Therapeutic approaches for cardiac regeneration and repair. Nat Rev Cardiol. 2018;15:585-600.

Hausenloy DJ and Yellon DM. Myocardial ischemia-reperfusion injury: a neglected therapeutic target. J Clin Invest. 2013;123:92-100.

Her YF and Maher LJ, 3rd. Succinate Dehydrogenase Loss in Familial Paraganglioma: Biochemistry, Genetics, and Epigenetics. Int J Endocrinol. 2015;2015:296167.

Hirose K, Payumo AY, Cutie S, Hoang A, Zhang H, Guyot R, Lunn D, Bigley RB, Yu H, Wang J, Smith M, Gillett E, Muroy SE, Schmid T, Wilson E, Field KA, Reeder DM, Maden M, Yartsev MM, Wolfgang MJ, Grutzner F, Scanlan TS, Szweda LI, Buffenstein R, Hu G, Flamant F, Olgin JE and Huang GN. Evidence for hormonal control of heart Regenerative capacity during endothermy acquisition. Science. 2019;364:184-188.

Hochachka PW and Dressendorfer RH. Succinate accumulation in man during exercise. Eur J Appl Physiol Occup Physiol. 1976;35:235-42.

Honkoop H, de Bakker DE, Aharonov A, Kruse F, Shakked A, Nguyen PD, de Heus C, Garric L, Muraro MJ, Shoffner A, Tessadori F, Peterson JC, Noort W, Bertozzi A, Weidinger G, Posthuma G, Grun D, van der Laarse WJ, Klumperman J, Jaspers RT, Poss KD, van Oudenaarden A, Tzahor E and Bakkers J. Single-cell analysis uncovers that metabolic reprogramming by ErbB2 signaling is essential for cardiomyocyte proliferation in the regenerating heart. Elife. 2019;8.

Hu D, Linders A, Yamak A, Correia C, Kijlstra JD, Garakani A, Xiao L, Milan DJ, van der Meer P, Serra M, Alves PM and Domian IJ. Metabolic Maturation of Human Pluripotent Stem Cell-Derived Cardiomyocytes by Inhibition of HIF1alpha and LDHA. Circ Res. 2018;123:1066-1079.

Jessup M and Brozena S. Heart failure. The New England journal of medicine. 2003;348:2007-18.

Jopling C, Sleep E, Raya M, Marti M, Raya A and Belmonte JCI. Zebrafish heart regeneration occurs by cardiomyocyte dedifferentiation and proliferation. Nature. 2010;464:606-9.

Kaelin WG, Jr. and McKnight SL. Influence of metabolism on epigenetics and disease. Cell. 2013;153:56-69.

Kelly B and O'Neill LA. Metabolic reprogramming in macrophages and dendritic cells in innate immunity. Cell Res. 2015;25:771-84.

Khera R, Pandey A, Ayers CR, Agusala V, Pruitt SL, Halm EA, Drazner MH, Das SR, de Lemos JA and Berry JD. Contemporary Epidemiology of Heart Failure in Fee-For-Service Medicare Beneficiaries Across Healthcare Settings. Circ Heart Fail. 2017;10.

Kikuchi K, Holdway JE, Werdich AA, Anderson RM, Fang Y, Egnaczyk GF, Evans T, MacRae CA, Stainier DYR and Poss KD. Primary contribution to zebrafish heart regeneration by gata4(+) cardiomyocytes. Nature. 2010;464:601-5.

Kimura W, Xiao F, Canseco DC, Muralidhar S, Thet S, Zhang HM, Abderrahman Y, Chen R, Garcia JA, Shelton JM, Richardson JA, Ashour. Am, Asaithamby A, Liang H, Xing C, Lu Z, Zhang CC and Sadek HA. Hypoxia fate mapping identifies cycling cardiomyocytes in the adult heart. Nature. 2015;523:226-30.

King A, Selak MA and Gottlieb E. Succinate dehydrogenase and fumarate hydratase: linking mitochondrial dysfunction and cancer. Oncogene. 2006;25:4675-82.

Knobloch M, Pilz GA, Ghesquiere B, Kovacs WJ, Wegleiter T, Moore DL, Hruzova M, Zamboni N, Carmeliet P and Jessberger S. A Fatty Acid Oxidation-Dependent Metabolic Shift Regulates Adult Neural Stem Cell Activity. Cell Rep. 2017;20:2144-2155.

Kula-Alwar D, Prag HA and Krieg T. Targeting Succinate Metabolism in Ischemia/Reperfusion Injury. Circulation. 2019;140:1968-1970.

Kumar D, Hacker TA, Buck J, Whitesell LF, Kaji EH, Douglas PS and Kamp TJ. Distinct mouse coronary anatomy and myocardial infarction consequent to ligation. Coron Artery Dis. 2005;16:41-4.

Lavine KJ, Epelman S, Uchida K, Weber KJ, Nichols CG, Schilling JD, Ornitz DM, Randolph GJ and Mann DL. Distinct macrophage lineages contribute to disparate patterns of cardiac recovery and remodeling in the neonatal and adult heart. Proceedings of the National Academy of Sciences of the United States of America. 2014;111:16029-34.

Leach JP, Heallen T, Zhang M, Rahmani M, Morikawa Y, Hill MC, Segura A, Willerson JT and Martin JF. Hippo pathway deficiency reverses systolic heart failure after infarction. Nature. 2017;550:260-264.

Letouze E, Martinelli C, Loriot C, Burnichon N, Abermil N, Ottolenghi C, Janin M, Menara M, Nguyen AT, Benit P, Buffet A, Marcaillou C, Bertherat J, Amar L, Rustin P, De Reynies A, Gimenez-Roqueplo AP and Favier J. SDH mutations establish a hypermethylator phenotype in paraganglioma. Cancer Cell. 2013;23:739-52.

Li Xiong, Hua Li, Li-Na Jiang, Jing-Ming Ge, Wen-Chao Yang, Xiao Lei Zhu, and Guang-Fu Yang. Structure-Based Discovery of Potential Fungicides as Succinate Ubiquinone Oxidoreductase Inhibitors. J. Agric. Food Chem. 2017, 65, 5, 1021-1029.

Lian X, Hsiao C, Wilson G, Zhu K, Hazeltine LB, Azarin SM, Raval KK, Zhang J, Kamp TJ and Palecek SP. Robust cardiomyocyte differentiation from human pluripotent stem cells via temporal modulation of canonical Wnt signaling. Proceedings of the National Academy of Sciences of the United States of America. 2012;109:E1848-57.

Lian X, Zhang J, Azarin SM, Zhu K, Hazeltine LB, Bao X, Hsiao C, Kamp TJ and Palecek SP. Directed cardiomyocyte differentiation

(56) References Cited

OTHER PUBLICATIONS from human pluripotent stem cells by modulating Wnt/beta-catenin signaling under fully defined conditions. Nature protocols. 2013;8:162-75.
Lian X, Bao X, Zilberter M, Westman M, Fisahn A, Hsiao C, Hazeltine LB, Dunn KK, Kamp TJ and Palecek SP. Chemically defined, albumin-free human cardiomyocyte generation. Nat Methods. 2015;12:595-6.
Lili Guo, Alexander A Shestov, Andrew J Worth, Kavindra Nath, David S Nelson, Dennis B Leeper, Jerry D Glickson, Ian A Blair. Inhibition of Mitochondrial Complex II by the Anticancer Agent Lonidamine. J Biol Chem. Jan. 1, 2016;291(1):42-57.
Lopaschuk GD, Collins-Nakai RL and Itoi T. Developmental changes in energy substrate use by the heart. Cardiovasc Res. 1992;26:1172-80.
Mahmoud AI, Kocabas F, Muralidhar SA, Kimura W, Koura AS, Thet S, Porrello ER and Sadek HA. Meisl regulates postnatal cardiomyocyte cell cycle arrest. Nature. 2013;497:249-253.
Mahmoud AI, Porrello ER, Kimura W, Olson EN and Sadek HA. Surgical models for cardiac regeneration in neonatal mice. Nature protocols. 2014;9:305-11.
Mahmoud AI, OMeara CC, Gemberling M, Zhao L, Bryant DM, Zheng R, Gannon JB, Cai L, Choi WY, Egnaczyk GF, Burns CE, Burns CG, MacRae CA, Poss KD and Lee RT. Nerves Regulate Cardiomyocyte Proliferation and Heart Regeneration. Dev Cell. 2015;34:387-99.
Mahmoud AI and Porrello ER. Turning back the cardiac regenerative clock: lessons from the neonate. Trends Cardiovasc Med. 2012;22:128-33.
Mills EL, Kelly B, Logan A, Costa ASH, Varma M, Bryant CE, Tourlomousis P, Dabritz JHM, Gottlieb E, Latorre I, Corr SC, McManus G, Ryan D, Jacobs HT, Szibor M, Xavier RJ, Braun T, Frezza C, Murphy MP and O'Neill LA. Succinate Dehydrogenase Supports Metabolic Repurposing of Mitochondria to Drive Inflammatory Macrophages. Cell. 2016;167:457-470 e13.
Miyadera H, Shiomi K, Ui H, Yamaguchi Y, Masuma R, Tomoda H, Miyoshi H, Osanai A, Kita K, Omura S. Atpenins, potent and specific inhibitors of mitochondrial complex II (succinate-ubiquinone oxidoreductase). Proc Natl Acad Sci USA. Jan. 20 21, 2003;100(2):473-7.
Monroe TO, Hill MC, Morikawa Y, Leach JP, Heallen T, Cao S, Krijger PHL, de Laat W, Wehrens XHT, Rodney GG and Martin Jf. Yap Partially Reprograms Chromatin Accessibility to Directly Induce Adult Cardiogenesis In Vivo. Dev Cell. 2019;48:765-779 e7.
Morikawa Y, Heallen T, Leach J, Xiao Y and Martin JF. Dystrophin-glycoprotein complex sequesters Yap to inhibit cardiomyocyte proliferation. Nature. 2017;547:227-231.
Murphy MP. How mitochondria produce reactive oxygen species. Biochem J. 2009;417:1-13.
Nakada Y, Canseco DC, Thet S, Abdisalaam S, Asaithamby A, Santos CX, Shah AM, Zhang H, Faber JE, Kinter MT, Szweda LI, Xing C, Hu Z, Deberardinis RJ, Schiattarella G, Hill JA, Oz O, Lu Z, Zhang CC, Kimura W and Sadek HA. Hypoxia induces heart regeneration in adult mice. Nature. 2017;541:222-227.
Oberpriller JO and Oberpriller JC. Response of the adult newt ventricle to injury. JExp Zool. 1974;187:249-53.
Parikh SS, Blackwell DJ, Gomez-Hurtado N, Frisk M, Wang L, Kim K, Dahl CP, Fiane A, Tonnessen T, Kryshtal DO, Louch WE and Knollmann BC. Thyroid and Glucocorticoid Hormones Promote Functional T-Tubule Development in Human-Induced Pluripotent Stem Cell-Derived Cardiomyocytes. CircRes. 2017;121:1323-1330.
Patterson M, Barske L, Van Handel B, Rau CD, Gan P, Sharma A, Parikh S, Denholtz M, Huang Y, Yamaguchi Y, Shen H, Allayee H, Crump JG, Force TI, Lien CL, Makita T, Lusis AJ, Kumar SR and Sucov HM. Frequency of mononuclear diploid cardiomyocytes underlies natural variation in heart regeneration. Nat Genet. 2017;49:1346-1353.
Pisarenko O, Studneva I, Khlopkov V, Solomatina E and Ruuge E. An assessment of anaerobic metabolism during ischemia and reperfusion in isolated guinea pig heart. Biochim Biophys Acta. 1988;934:5563.

Pollard PJ, Briere JJ, Alam NA, Barwell J, Barclay E, Wortham NC, Hunt T, Mitchell M, Olpin S, Moat SJ, Hargreaves IP, Heales SJ, Chung YL, Griffiths JR, Dalgleish A, McGrath JA, Gleeson MJ, Hodgson SV, Poulsom R, Rustin P and Tomlinson IP. Accumulation of Krebs cycle intermediates and over-expression of HIF1alpha in tumours which result from germline FH and SDH mutations. Hum Mol Genet. 2005;14:2231-9.
Porrello ER, Mahmoud AI, Simpson E, Hill JA, Richardson JA, Olson EN and Sadek HA. Transient regenerative potential of the neonatal mouse heart. Science. 2011;331:1078-80.
Porrello ER, Mahmoud AI, Simpson E, Johnson BA, Grinsfelder D, Canseco D, Mammen PP, Rothermel BA, Olson EN and Sadek HA. Regulation of neonatal and adult mammalian heart regeneration by the miR-15 family. Proceedings of the National Academy of Sciences of the United States of America. 2013;110:187-92.
Poss KD, Wilson LG and Keating MT. Heart regeneration in zebrafish. Science 2002;298:2188-2190.
Puente, Bao N. et al., The oxygen-rich postnatal environment induces cardiomyocyte cell-cycle arrest through DNA damage response. Cell. Apr. 24, 2014;157(3):565-79.
Quaife-Ryan GA, Sim CB, Ziemann M, Kaspi A, Rafehi H, Ramialison M, El-Osta A, Hudson JE and Porrello ER. Multicellular Transcriptional Analysis of Mammalian Heart Regeneration. Circulation. 2017;136:1123-1139.
Rodriguez-Cuenca S, Cocheme HM, Logan A, Abakumova I, Prime TA, Rose C, Vidal-Puig A, Smith AC, Rubinsztein DC, Fearnley IM, Jones BA, Pope S, Heales SJ, Lam BY, Neogi SG, McFarlane I, James AM, Smith RA and Murphy MP. Consequences of longterm oral administration of the mitochondria-targeted antioxidant MitoQ to wild-type mice. Free Radic Biol Med. 2010;48:161-72.
Sadek H and Olson EN. Toward the Goal of Human Heart Regeneration. Cell Stem Cell. 2020;26:7-16.
Sciacovelli M, Guzzo G, Morello V, Frezza C, Zheng L, Nannini N, Calabrese F, Laudiero G, Esposito F, Landriscina M, Defilippi P, Bernardi P and Rasola A. The mitochondrial chaperone TRAP1 promotes neoplastic growth by inhibiting succinate dehydrogenase. Cell Metab. 2013;17:988-999.
Scialo F, Femandez-Ayala DJ and Sanz A. Role of Mitochondrial Reverse Electron Transport in ROS Signaling: Potential Roles in Health and Disease. Front Physiol. 2017;8:428.
Seim GL, Britt EC, John SV, Yeo FJ, Johnson AR, Eisenstein RS, Pagliarini DJ and Fan J. Two-stage metabolic remodelling in macrophages in response to lipopolysaccharide and interferon-y stimulation. Nature Metabolism. 2019;1:731-742.
Singla DK, Hacker TA, Ma L, Douglas PS, Sullivan R, Lyons GE and Kamp TJ. Transplantation of embryonic stem cells into the infarcted mouse heart: formation of multiple cell types. J Mol Cell Cardiol. 2006;40:195-200.
Smith RA and Murphy MP. Animal and human studies with the mitochondria-targeted antioxidant MitoQ. Ann NY Acad Sci. 2010;1201:96-103.
Son G and Han J. Roles of mitochondria in neuronal development. BMB Rep. 2018;51:549-556.
Tseng PL, Wu WH, Hu TH, Chen CW, Cheng HC, Li CF, Tsai WH, Tsai HJ, Hsieh MC, Chuang JH and Chang WT. Decreased succinate dehydrogenase B in human hepatocellular carcinoma accelerates tumor malignancy by inducing the Warburg effect. Sci Rep. 2018;8:3081.
Vagnozzi RJ, Maillet M, Sargent MA, Khalil H, Johansen AKZ, Schwanekamp JA, York AJ, Huang V, Nahrendorf M, Sadayappan S and Molkentin JD. An acute immune response underlies the benefit of cardiac stem cell therapy. Nature. 2020;577:405-409.
Valls-Lacalle L, Barba I, Miro-Casas E, Alburquerque-Bejar JJ, Ruiz-Meana M, Fuertes-Agudo M, Rodriguez-Sinovas A and Garcia-Dorado D. Succinate dehydrogenase inhibition with malonate during reperfusion reduces infarct size by preventing mitochondrial permeability transition. Cardiovasc Res. 2016;109:374-84.
Valls-Lacalle L, Barba I, Miro-Casas E, Ruiz-Meana M, Rodriguez-Sinovas A and Garcia-Dorado D. Selective Inhibition of Succinate Dehydrogenase in Reperfused Myocardium with Intracoronary Malonate Reduces Infarct Size. Sci Rep. 2018;8:2442.
Virani SS, Alonso A, Benjamin EJ, Bittencourt MS, Callaway CW, Carson AP, Chamberlain AM, Chang AR, Cheng S, Delling FN,

(56) References Cited

OTHER PUBLICATIONS

Djousse L, Elkind MSV, Ferguson JF Fornage M, Khan SS, Kissela BM, Knutson KL, Kwan TW, Lackland DT, Lewis TT, Lichtman JH, Longenecker CT, Loop MS, Lutsey PL, Martin SS, Matsushita K, Moran AE, Mussolino ME, Perak AM, Rosamond WD, Roth GA, Sampson UKA, Satou GM, Schroeder EB, Shah SH, Shay CM, Spartano NL, Stokes A, Tirschwell DL, VanWagner LB, Tsao CW, American Heart Association Council on E, Prevention Statistics C and Stroke Statistics S. Heart Disease and Stroke Statistics—2020 Update: A Report From the American Heart Association. Circulation. 2020;141:e139-e596.

Wang Z, Ying Z, Bosy-Westphal A, Zhang J, Schautz B, Later W, Heymsfield SB and Muller MJ. Specific metabolic rates of major organs and tissues across adulthood: evaluation by mechanistic model of resting energy expenditure. Am J Clin Nutr. 2010;92:1369-77.

Webster WS and Abela D. The effect of hypoxia in development. Birth Defects Res C Embryo Today. 2007;81:215-28.

Writing Group M, Mozaffarian D, Benjamin EJ, Go AS, Arnett DK, Blaha MJ, Cushman M, Das SR, de Ferranti S, Despres JP, Fullerton HJ, Howard VJ, Huffman MD, Isasi CR, Jimenez MC, Judd SE, Kissela BM, Lichtman JH, Lisabeth LD, Liu S, Mackey RH, Magid DJ, McGuire DK, Mohler ER, 3rd, Moy CS, Muntner P, Mussolino ME, Nasir K, Neumar RW, Nichol G, Palaniappan L, Pandey DK, Reeves MJ, Rodriguez CJ, Rosamond W, Sorlie PD, Stein J, Towfighi A, Turan TN, Virani SS, Woo D, Yeh RW, Turner MB, American Heart Association Statistics C and Stroke Statistics S. Heart Disease and Stroke Statistics-2016 Update: A Report From the American Heart Association. Circulation. 2016;133:e38-360.

Yacoub M. Cardiac donation after circulatory death: a time to reflect. Lancet. 2015;385:2554-6.

Ye L, D'Agostino G, Loo SJ, Wang CX, Su LP, Tan SH, Tee GZ, Pua CJ, Pena EM, Cheng RB, Chen WC, Abdurrachim D, Lalic J, Tan RS, Lee TH, Zhang J and Cook SA. Early Regenerative Capacity in the Porcine Heart. Circulation. 2018;138:2798-2808.

Yu J, Hu K, Smuga-Otto K, Tian S, Stewart R, Slukvin, II and Thomson JA. Human induced pluripotent stem cells free of vector and transgene sequences. Science. 2009;324:797-801.

Zhang J, Wang YT, Miller JH, Day MM, Munger JC and Brookes PS. Accumulation of Succinate in Cardiac Ischemia Primarily Occurs via Canonical Krebs Cycle Activity. Cell Rep. 2018;23:2617-2628.

Zhu W, Zhang E, Zhao M, Chong Z, Fan C, Tang Y, Hunter JD, Borovjagin AV, Walcott GP, Chen JY, Qin G and Zhang J. Regenerative Potential of Neonatal Porcine Hearts. Circulation. 2018;138:2809-2816.

Zweier JL, Flaherty JT and Weisfeldt ML. Direct measurement of free radical generation following reperfusion of ischemic myocardium. Proceedings of the National Academy of Sciences of the United States of America. 1987;84:1404-7.

\* cited by examiner

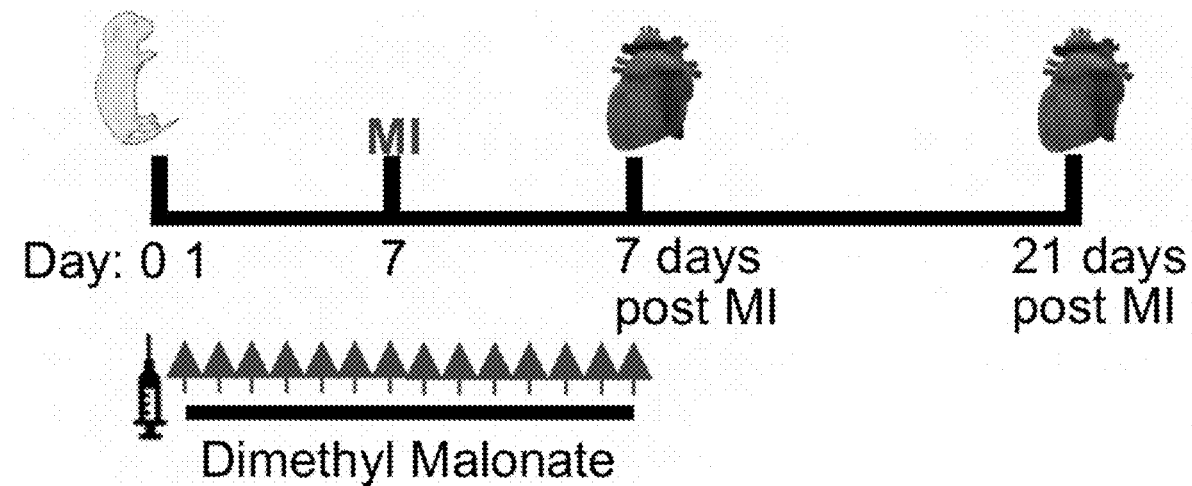
FIG. 10A
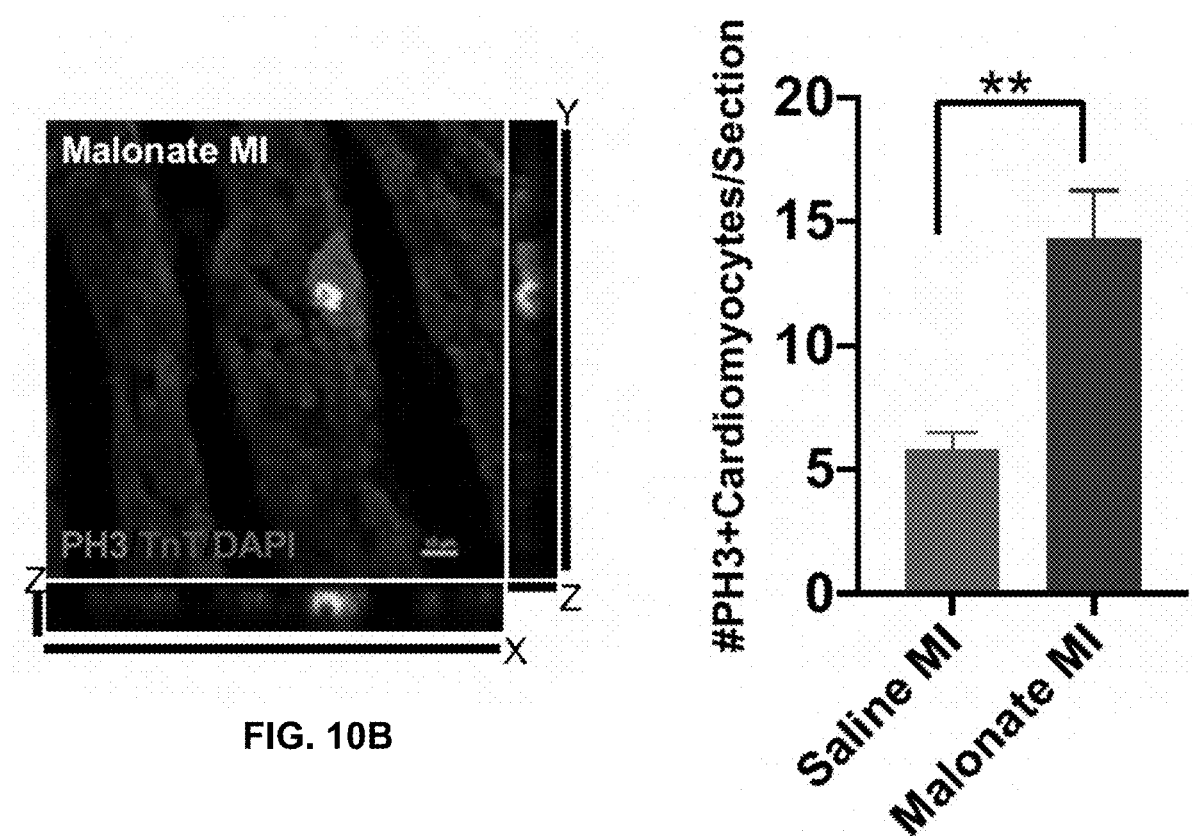
FIG. 10B
FIG. 10C

Mitosis

Cytokinesis

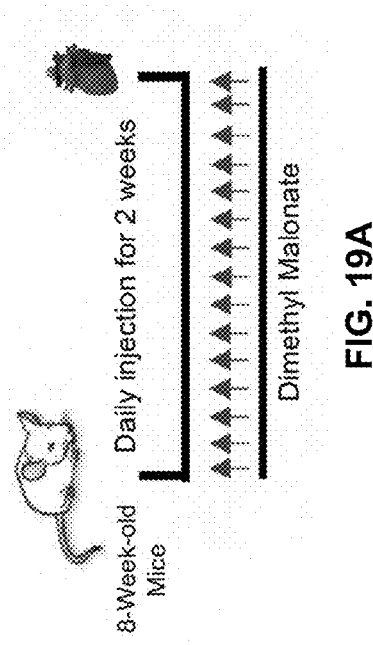
FIG. 19A
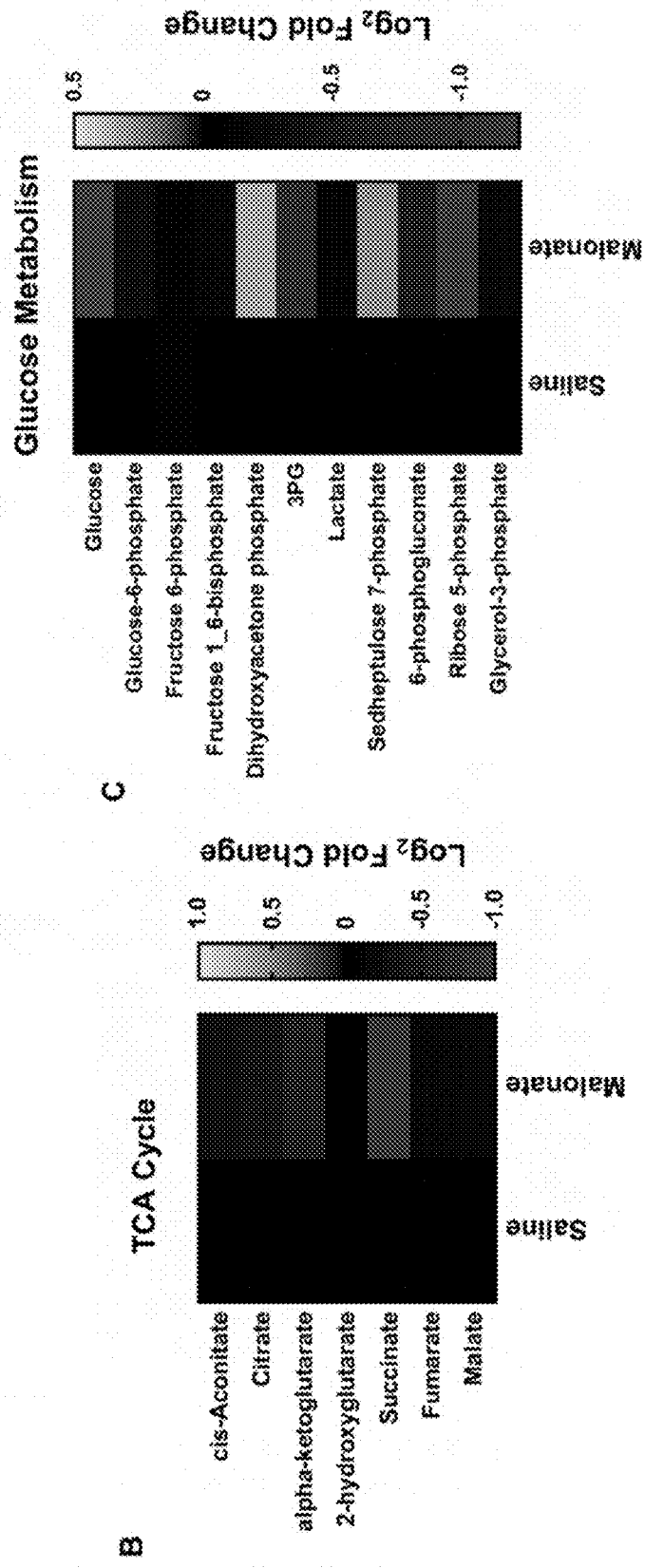
FIG. 19C
FIG. 19B

COMPOSITIONS AND METHODS FOR IMPROVING CARDIAC STRUCTURE AND/OR FUNCTION

FIELD OF THE INVENTION

The invention is directed to compositions and methods for improving cardiac structure and/or function, including heart regeneration, in subjects in need thereof.

BACKGROUND

A major cause of systolic heart failure is the inability of the adult mammalian heart to regenerate following injuries, with the most common being infarction. In contrast, lower vertebrates, such as zebrafish, are capable of regenerating their heart following injury. Neonatal mice are capable of regenerating their hearts but lose this potential in the first week of life. This regenerative response is mediated by proliferation of pre-existing cardiomyocytes. Adult humans and mice appear to lack the critical cardiac regeneration potential present in lower vertebrates and neonatal mice. Treatments for stimulating this process in adult humans are needed.

SUMMARY OF THE INVENTION

One aspect of the invention is directed to methods of improving cardiac structure and/or function in a subject in need thereof. The methods comprise administering to the subject a succinate dehydrogenase inhibitor in an amount and for a time effective to elicit an improvement in cardiac structure and/or function.

In some versions, the subject comprises a myocardial lesion. In some versions, the myocardial lesion comprises fibrosis (fibrotic scarring), decreased myocardial thickness, a myocardial infarct, or any combination thereof. In some versions, the subject comprises a myocardial infarct.

In some versions, the administering comprises administering the succinate dehydrogenase inhibitor to the subject after a cardiac event. In some versions, the administering comprises administering the succinate dehydrogenase inhibitor to the subject after a cardiac event, wherein if the cardiac event comprises cardiac ischemia-reperfusion, the succinate dehydrogenase inhibitor is administered to the subject after the cardiac ischemia-reperfusion. In some versions, the administering comprises administering the succinate dehydrogenase inhibitor to the subject at least 90 minutes after the cardiac event, such as the cardiac ischemia-reperfusion.

In some versions, the administering comprises administering the succinate dehydrogenase inhibitor to the subject over a period of time after a cardiac event. In some versions, the administering comprises administering the succinate dehydrogenase inhibitor to the subject over a period of time after a cardiac event, wherein if the cardiac event comprises cardiac ischemia-reperfusion, the succinate dehydrogenase inhibitor administered to the subject over a period of time after the cardiac ischemia-reperfusion. In some versions, the period of time comprises a point in time at least 90 minutes after the cardiac event, such as the cardiac ischemia-reperfusion. In some versions, the period of time spans at least 24 hours. In some versions, the succinate dehydrogenase inhibitor is intermittently administered to the subject over the period of time.

In some versions, the administering comprises administering the succinate dehydrogenase inhibitor to the subject after a cardiac event comprising cardiac ischemia, cardiac ischemia-reperfusion, myocardial infarction, or any combination thereof. In some versions, the administering comprises administering the succinate dehydrogenase inhibitor to the subject after a cardiac event comprising cardiac ischemia, cardiac ischemia-reperfusion, myocardial infarction, or any combination thereof, wherein if the cardiac event comprises cardiac ischemia-reperfusion, the succinate dehydrogenase inhibitor is administered to the subject after the cardiac ischemia-reperfusion. In some versions, the administering comprises administering the succinate dehydrogenase inhibitor to the subject at least 90 minutes after the cardiac event, such as the cardiac ischemia-reperfusion.

In some versions, the administering comprises administering the succinate dehydrogenase inhibitor to the subject over a period of time after a cardiac event comprising cardiac ischemia, cardiac ischemia-reperfusion, myocardial infarction, or any combination thereof. In some versions, the administering comprises administering the succinate dehydrogenase inhibitor to the subject over a period of time after a cardiac event comprising cardiac ischemia, cardiac ischemia-reperfusion, myocardial infarction, or any combination thereof, wherein if the cardiac event comprises cardiac ischemia-reperfusion, the succinate dehydrogenase inhibitor administered to the subject over a period of time after the cardiac ischemia-reperfusion. In some versions, the period of time comprises a point in time at least 90 minutes after the cardiac event, such as the cardiac ischemia-reperfusion. In some versions, the period of time spans at least 24 hours. In some versions, the succinate dehydrogenase inhibitor is intermittently administered to the subject over the period of time.

In some versions, the succinate dehydrogenase inhibitor is administered in an amount and for a time effective to elicit an improvement in cardiac function. In some versions, the improvement in cardiac function comprising any one or more of an increase in cardiomyocyte proliferation, an increase in ejection fraction, an increase in fractional shortening, a decrease in left ventricle internal diameter diastole, and a decrease in left ventricle internal diameter systole, in any combination.

In some versions, the succinate dehydrogenase inhibitor is administered in an amount and for a time effective to elicit an improvement in cardiac structure. In some versions, the improvement in cardiac structure comprising any one or more of decreased fibrosis, an increase in myocardial thickness, an increase in coronary artery formation, an increase in capillary density, an increase in revascularization, and a decrease in myocardial lesion size, in any combination. In some versions, the improvement in cardiac structure occurs in an infarcted zone in the heart.

In some versions, the succinate dehydrogenase inhibitor comprises a succinate-analog inhibitor. In some versions, the succinate-analog inhibitor comprises a malonate compound.

In some versions, the succinate dehydrogenase inhibitor comprises a ubiquinone-type inhibitor. In some versions, the ubiquinone-type inhibitor comprises an atpenin.

Another aspect of the invention is directed to compositions suitable for carrying out the methods of the invention. In some versions, the compositions comprise a succinate dehydrogenase inhibitor in combination with a carrier.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 5A) Schematic of dimethyl malonate injection and MI strategy. (FIGS. 5B-5D) Immunostaining and quantification of pH3 positive cardiomyocytes showing a significant increase in the levels of mitotic myocytes in dimethyl malonate-injected hearts at 7 days post-MI compared to controls. (FIGS. 5E and 5F) Immunostaining and quantification of Aurora B positive cardiomyocytes demonstrating a significant increase in myocyte cytokinesis in the dimethyl malonate-injected mice. (n=5 mice per group)

(FIG. 7A) Z-stack confocal image of a pH3 positive cardiomyocyte (FIG. 7B) Quantification of mitotic cardiomyocytes showing a significant increase in the number of mitotic cardiomyocytes in MitoQ-injected hearts at 7 days post-MI, compared to controls. (FIG. 7C) MitoQ-injected mice show persistence of the fibrotic scar similar to controls. (FIG. 7D) Echo measurements demonstrating that MitoQ did not result in any improvement in contractile function following injury. (n=5-8 mice per group)

(FIG. 8A) Trichrome staining of malonate-injected hearts at 4 weeks following adult MI, showing complete restoration of cardiac structure and no scar in malonate-injected mice compared to controls. (FIG. 8B) Left ventricular systolic function quantified by EF and FS at 4 weeks post-MI showing complete functional recovery in malonate-injected hearts compared to saline-injected controls. (n=5-6 mice per group) (FIG. 8C) Malonate-dependent induction of re-vascularization in the infarcted zone as shown by coronary vessel casting by Microfil.

(FIG. 9A) Schematic of injection period and myocardial infarction strategy in neonatal mice. (FIG. 9B) High magnification Z-stack image of a mitotic cardiomyocyte following immunostaining of pH3 and cTnT at 7 days post-MI. Scale bar, 10 μm. (FIG. 9C) Quantification of the number of mitotic cardiomyocytes per section showing a significant decrease in cardiomyocyte mitosis following dimethyl succinate injection. (FIG. 9D) Immunostaining of the DNA double-strand breaks marker γH2AX. Scale bar, 100 μm. (FIG. 9E) Quantification of cardiomyocytes with increased γH2AX foci demonstrating a significant increase in DNA damage in succinate-treated mice compared to controls. (FIG. 9F) Trichrome staining demonstrating persistence of the fibrotic scar following MI in the dimethyl succinate-injected mice compared to saline-injected controls. Scale bar, 1 mm. (FIG. 9G) Echocardiography at 21 days post-MI showing a significant reduction in the cardiac function of dimethyl succinate-injected mice following MI compared to saline-injected controls as measured by ejection fraction (EF), fractional shortening (FS), left ventricle internal diameter diastole (LVIDD) and left ventricle internal diameter systole (LVIDS). (n=5-8 mice per group). *P<0.05 by Student's t-test.

FIGS. 10A-10I. Malonate promotes cardiomyocyte proliferation and heart regeneration in the postnatal heart following MI. (FIG. 10A) Schematic of dimethyl malonate injection and MI strategy. (FIGS. 10B and 10C) Immunostaining and quantification of pH3 positive cardiomyocytes showing a significant increase in the levels of mitotic myocytes in dimethyl malonate-injected hearts at 7 days post-MI compared to controls. Scale bar, 10 μm. (FIGS. 10D and 10E) Immunostaining and quantification of Aurora B positive cardiomyocytes demonstrating a significant increase in myocyte cytokinesis in the dimethyl malonate-injected mice. Scale bar, 10 μm. (FIGS. 10F and 10G) Wheat germ agglutinin (WGA) staining and cell size quantification showing decrease in the cardiomyocyte size in malonate-injected hearts at 21 days post-MI. Quantitative analyses represent counting of multiple fields from independent samples per group (~700 cells per group). Scale bar, 10 µm. (FIG. 10H) Trichrome staining of malonate-injected hearts at 21 days post-MI at P7, showing complete regeneration in dimethyl malonate-injected mice compared to control. Scale bar, 1 mm. (FIG. 10I) Left ventricular systolic function quantified by EF, FS, LVIDD and LVIDS at 3 weeks post-MI demonstrating functional recovery in dimethyl malonate-injected MI hearts compared to the saline-injected controls. (n=5-8 mice per group). *P<0.05, P<0.005, *P<0.0001 by Student's t-test.

(FIG. 12A) Schematic of Atpenin A5 injection and MI strategy. (FIG. 12B) Z-stack confocal image of a mitotic cardiomyocyte stained with pH3 and cTnT. Scale bar, 10 µm. (FIG. 12C) Quantification of mitotic cardiomyocytes showing a significant increase in the number of mitotic cardiomyocytes in Atpenin A5-injected mice at 7 days post-MI compared to controls. (FIG. 12D) Z-stack confocal image of an Aurora B positive cardiomyocyte. Scale bar, 10 µm. (FIG. 12E) Quantification of cardiomyocytes undergoing cytokinesis showing a significant increase in the number of cardiomyocytes in cytokinesis in Atpenin A5-injected mice at 7 days post-MI compared to controls. (FIG. 12F) Trichrome staining of Atpenin A5-injected mice at 3 weeks post-MI at P7 demonstrating myocardial regeneration and a significant reduction in scar size in Atpenin A5-injected mice compared to controls. Scale bar, 1 mm. (FIG. 12G) Quantification of scar size by ImageJ software from serial sections from ligature to apex. (FIG. 12H) Echocardiography measurements of EF, FS, LVIDD and LVIDS at 3 weeks post-MI showing restoration of cardiac function in Atpenin A5-injected mice compared to controls. (n=6-8 mice per group). *P<0.05, **P<0.005 by Student's t-test.

(FIG. 13A) Schematic of dimethyl malonate injection following adult MI. (FIG. 13B) TTC viability stain and quantification showing no significant difference in myocardial necrosis (white) in both saline and dimethyl malonate-injected mice at 3 days post-MI (DPMI). Scale bar, 1 mm. (FIG. 13C) Quantification of TUNEL positive cardiomyocytes demonstrating no significant difference between TUNEL positive myocytes in saline and malonate-injected mice at 3 days post-MI. (FIG. 13D) Z-stack confocal image of a pH3 positive cardiomyocyte at 14-days post-MI. Scale bar, 10 µm. Quantification of the percentage of pH3 positive cardiomyocytes showing a significant increase in the numbers of mitotic cardiomyocytes in dimethyl malonate-injected hearts at 14-days post-MI compared to controls. (FIG. 13E) Z-stack confocal image of an Aurora B-positive cardiomyocyte at 14-days post-MI. Scale bar, 10 µm. Quantification of the percentage of Aurora B-positive cardiomyocytes demonstrating a significant increase in the numbers of cardiomyocytes undergoing cytokinesis in dimethyl malonate-injected hearts at 14-days post-MI compared to controls. (FIG. 13F) Representative image and quantification of BrdU-positive cardiomyocytes demonstrating a significant increase in BrdU-positive cardiomyocytes at 14 days post-MI in malonate-treated mice. Scale bar, 10 µm. (FIG. 13G) Cardiomyocyte nucleation staining with connexin 43 (Cx43) and DAPI and quantification at 14 days post-MI demonstrating a significant increase in mononucleated cardiomyocytes as well as a significant decrease in binucleated cardiomyocytes following malonate treatment. Scale bar, 50 µm. (FIG. 13H) Immunostaining and quantification of the DNA double-strand breaks marker γH2AX demonstrating a significant decrease in DNA damage in malonate-treated mice compared to controls. Scale bar, 10 µm. (FIG. 13I) Relative intracellular abundance of succinate showing a significant increase in succinate levels in malonate-treated mice at 14 days post-MI (n=3-6 mice per group). *P<0.05, ***P<0.0001 by Student's t-test. n.s. indicates not significant.

(FIG. 16A) Trichrome staining of heart sections from saline and dimethyl malonate-injected mice at 14 and 28 days following adult MI, showing restoration of cardiac structure and no fibrotic scarring by 28 days post-MI in dimethyl malonate-injected mice. Quantification of scar size demonstrating a significant reduction in fibrosis in dimethyl malonate treated mice at 28 days post-MI. (FIG. 16B) Echocardiography of cardiac function measured by EF, FS, LVIDD and LVIDS at 14- and 28-days post-MI showing a significant functional recovery in dimethyl malonate-injected hearts compared to saline-injected controls at 28 days post-MI. (FIG. 16C) Wheat germ agglutinin (WGA) staining and cell size quantification showing decrease in cardiomyocyte size in dimethyl malonate-injected hearts at 4 weeks post-MI. Quantitative analyses represent counting of multiple fields from 5-6 independent samples per group (750~1000 cells per group). Scale bar, 10 µm. (FIG. 16D) Heart weight-to-body weight ratios at 28 days post-MI showing no significant difference between saline and malonate-injected mice. (n=5-6 mice per group). *P<0.05, P<0.005, *P<0.0001 by Student's t-test. One-way ANOVA was performed by Tukey's multiple comparison test to determine the differences of group mean among treatment groups. Different letters indicate significant differences among groups. n.s. indicates not significant.

FIGS. 19A-19F. Malonate induces a dynamic metabolic shift in the adult heart and promotes revascularization following MI. (FIG. 19A) Schematic of malonate administration for metabolomics. (FIGS. 19B and 19C) Metabolomic changes of tricarboxylic acid (TCA) cycle and glucose metabolism in saline and malonate treated mice at 14 days following treatment. Relative abundance of metabolites in malonate-treated mice is compared to saline-treated mice and presented as a heatmap on a $\log_2$ scale demonstrating a dynamic metabolic shift from oxidative phosphorylation to glucose metabolism in malonate-treated mice. (FIG. 19D) Coronary vessel casting by MICROFIL injection at 28 days post-MI showing a significant increase in revascularization of the infarct zone in malonate-treated mice compared to controls. Quantification of vasculature in region of interest (ROI) by analyzing binarized images for grey level intensity by ImageJ demonstrating a significant increase in vascular density in the infarct zone. (FIG. 19E) Immunostaining with the endothelial marker PECAM and vascular smooth muscle cell marker α-SMA. Scale bar, 100 μm. (FIG. 19F) Quantification of vascular lineages demonstrating a significant increase in endothelial capillary density and vascular smooth muscle cells in the infarct zone at 28 days post-MI. (n=3-4 mice per group). *P<0.05, P<0.005, *P<0.0001 by Student's t-test.

(FIG. 20A) Schematic of malonate injection and MI strategy. (FIG. 20B) Trichrome staining of heart sections from saline and malonate-injected mice at 6 weeks post-MI. (FIG. 20C) Scar size quantification by ImageJ from serial sections per heart showing a significant reduction in scar size in malonate treated mice at 6 weeks post-MI. (FIG. 20D) Serial echocardiography measurements of EF, FS, LVID, LVIDS showing significant functional recovery in malonate-injected mice over time compared to controls. (n=6 mice per group). *P<0.05, P<0.005, *P<0.0001 by Student's t-test.

DETAILED DESCRIPTION OF THE INVENTION

Figure 1:
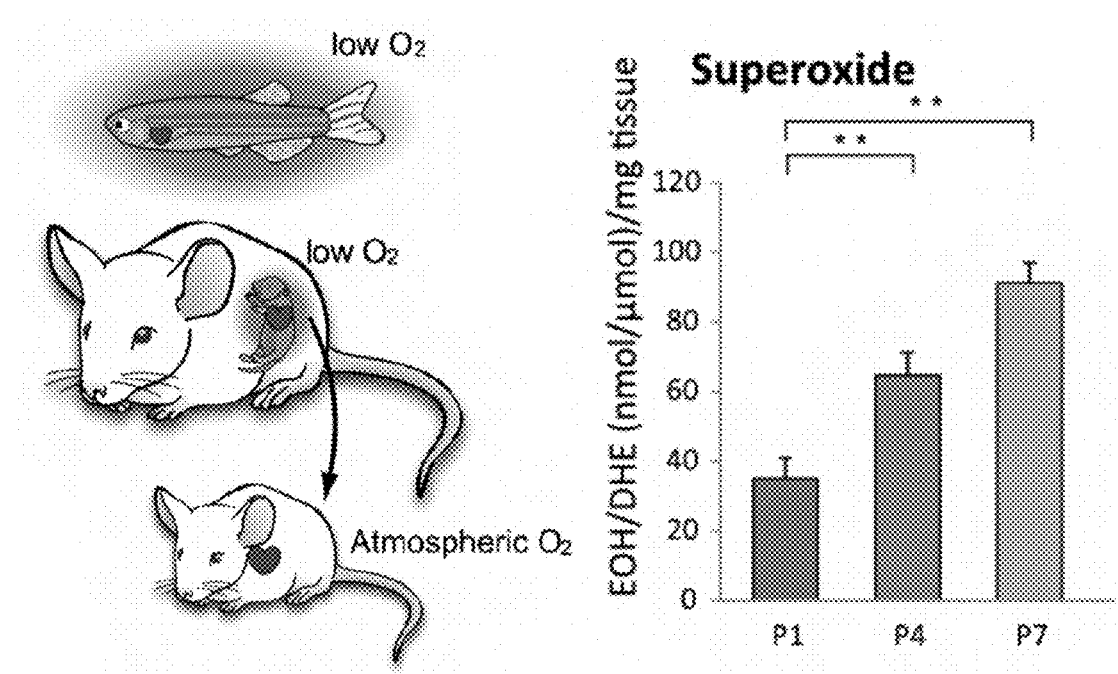
FIG. 1. Oxidation state and reactive oxygen species (ROS) levels correspond to cardiac regeneration capacity. (Left) Zebrafish and mammalian fetuses that possess robust regenerative ability reside in low oxygen environments. In contrast, postnatal mammals are exposed to high atmospheric oxygen levels, which correlates with loss of cardiac regenerative potential. (Right) Quantification of superoxide production demonstrating a significant increase in ROS in the first week after birth. Modified from Puente et al. 2014 (Bao N Puente, Wataru Kimura, Shalini A Muralidhar, Jesung Moon, James F Amatruda, Kate L Phelps, David Grinsfelder, Beverly A Rothermel, Rui Chen, Joseph A Garcia, Celio X Santos, SuWannee Thet, Eiichiro Mori, Michael T Kinter, Paul M Rindler, Serena Zacchigna, Shibani Mukherjee, David J Chen, Ahmed I Mahmoud, Mauro Giaccal, Peter S Rabinovitch, Asaithamby Aroumougame, Ajay M Shah, Luke I Szweda, Hesham A Sadek. The oxygen-rich postnatal environment induces cardiomyocyte cell-cycle arrest through DNA damage response. *Cell.* 2014 Apr. 24; 157(3):565-79).

Methods of the invention include methods of improving cardiac structure and/or function in a subject in need thereof. The methods can include administering to the subject a succinate dehydrogenase inhibitor in an amount and for a time effective to elicit an improvement in cardiac structure and/or function.

The subject can include any animal. Exemplary animals include mammals, such as humans.

The subject can be a subject with a myocardial lesion. The myocardial lesion can include any dead, damaged, or defective tissue in the myocardium. The myocardial lesion can result from cardiac ischemia, cardiac ischemia-reperfusion, myocardial infarction, blunt trauma, congenital defect(s), or any other injury or defect. As is known in the art, ischemia is a restriction in blood supply to tissues, such as due to an occlusion or blockage, causing a shortage of oxygen that is needed for cellular metabolism. Ischemia-reperfusion is the return of blood supply to tissue after a brief period of ischemia, such as within a period of 90 minutes of ischema. Myocardial infarction is the death (necrosis) of heart muscle secondary to prolonged ischemia. Accordingly, the myocardial lesion can comprise an ischemic injury, an ischemic-reperfusion injury, a myocardial infarct, or any combination thereof. Exemplary myocardial lesions include fibrosis (fibrotic scarring), decreased myocardial thickness, and myocardial infarcts. Decreased myocardial thickness is an area of the myocardium having reduced thickness relative to surrounding, contiguous, or proximal areas of the myocardium. The myocardial lesion can cause or contribute to a defect or deficiency in cardiac function.

The subject can be a subject undergoing or previously having undergone (in the past) a cardiac event. As used herein, "cardiac event" refers to any event causing or having the potential to cause a myocardial lesion. In some versions, the cardiac event comprises cardiac ischemia, cardiac ischemia-reperfusion, myocardial infarction, or any combination thereof.

The subject can be a subject comprising a defect or deficiency in cardiac structure and/or function. Such defects or deficiencies can result from a cardiac event. Exemplary defects or deficiencies in cardiac structure include myocardial lesions, such as fibrosis, decreased myocardial thickness, and myocardial infarcts. Exemplary defects or deficiencies in cardiac function include decreased ejection fraction, decreased fractional shortening, increased left ventricle internal diameter diastole, and increased left ventricle internal diameter systole. The defects or deficiencies can be relative to the subject prior to a cardiac event or relative to standard clinical values.

The succinate dehydrogenase inhibitor can be administered in an amount and for a time effective to elicit an improvement in cardiac function. Exemplary improvements in cardiac function include an increase in cardiomyocyte proliferation, an increase in ejection fraction, an increase in fractional shortening, a decrease in left ventricle internal diameter diastole, a decrease in left ventricle internal diameter systole, and any combination thereof. The improvements can be relative to the subject at a point in time prior to administration of the succinate dehydrogenase inhibitor, such as prior to a cardiac event.

The succinate dehydrogenase inhibitor can be administered in an amount and for a time effective to elicit an improvement in cardiac structure. Exemplary improvements in cardiac structure include decreased fibrosis, an increase in myocardial thickness, an increase in coronary artery formation, an increase in capillary density, an increase in revascularization, a reduction in myocardial lesion size, and any combination thereof. In some versions, the improvement in cardiac structure occurs in an infarcted zone in the heart. The improvements can be relative to the subject at a point in time prior to administration of the succinate dehydrogenase inhibitor, such as prior to a cardiac event.

The administering preferably comprises administering the succinate dehydrogenase inhibitor to the subject after a cardiac event, such as after any cardiac ischemia-reperfusion. Administering the succinate dehydrogenase inhibitor after the cardiac event does not preclude administering the succinate dehydrogenase inhibitor during or before the cardiac event, but the administration during or before the cardiac event is not considered to constitute administering the succinate dehydrogenase inhibitor after the cardiac event. In some versions, the administering comprises administering the succinate dehydrogenase inhibitor to the subject at least 5 minutes, at least 10 minutes, at least 30 minutes, at least 45 minutes, at least 60 minutes, at least 75 minutes, at least 90 minutes, at least 2 hours, at least 6 hours, at least 12 hours, at least 1 day, at least 4 days, at least 1 week, at least 2 weeks, at least 3 weeks, at least 4 weeks, at least 5 weeks, at least 6 weeks, or at least 8 weeks after the cardiac event, such as any cardiac ischemia-reperfusion. In some versions, the administering comprises administering the succinate dehydrogenase inhibitor to the subject within 5 minutes, within 10 minutes, within 30 minutes, within 45 minutes, within 60 minutes, within 75 minutes, within 90 minutes, within 2 hours, within 6 hours, within 12 hours, within 1 day, within 4 days, within 1 week, within 2 weeks, within 3 weeks, within 4 weeks, within 5 weeks, within 6 weeks, within 7 weeks, within 8 weeks, within 4 months, within 6 months, within 8 months, within 10 months, within 12 months, within 2 years, within 5 years, within 10 years, or within 20 years of the cardiac event, such as any cardiac ischemia-reperfusion.

The administering can comprise administering the succinate dehydrogenase inhibitor to the subject over a period of time after a cardiac event, such as any cardiac ischemia-reperfusion. By definition, the period of time commences with the first administration of the succinate dehydrogenase inhibitor after the cardiac event. This definition does not preclude administering the succinate dehydrogenase inhibitor during or before the cardiac event, but such administration during or before the cardiac event is not considered to be included within the period of time after the cardiac event.

The period of time can commence any time after the cardiac event, such as 5 minutes, 10 minutes, 30 minutes, 45 minutes, 60 minutes, 75 minutes, 90 minutes, 2 hours, 6 hours, 12 hours, 1 day, 4 days, 1 week, 2 weeks, 3 weeks, 4 weeks, 5 weeks, 6 weeks, or 8 weeks after the cardiac event, such as any cardiac ischemia-reperfusion. In some versions, the period of time commences at least 5 minutes, at least 10 minutes, at least 30 minutes, at least 45 minutes, at least 60 minutes, at least 75 minutes, at least 90 minutes, at least 2 hours, at least 6 hours, at least 12 hours, at least 1 day, at least 4 days, at least 1 week, at least 2 weeks, at least 3 weeks, at least 4 weeks, at least 5 weeks, at least 6 weeks or at least 8 weeks after the cardiac event, such as any cardiac ischemia-reperfusion. In some versions, the period of time commences within 5 minutes, within 10 minutes, within 30 minutes, within 45 minutes, within 60 minutes, within 75 minutes, within 90 minutes, within 2 hours, within 6 hours, within 12 hours, within 1 day, within 4 days, within 1 week, within 2 weeks, within 3 weeks, within 4 weeks, within 5 weeks, within 6 weeks, within 7 weeks, within 8 weeks, within 4 months, within 6 months, within 8 months, within 10 months, within 12 months, within 2 years, within 5 years, within 10 years, or within 20 years of the cardiac event, such as any cardiac ischemia-reperfusion.

In some versions, the period of time comprises a point in time at least 5 minutes, at least 10 minutes, at least 30 minutes, at least 45 minutes, at least 60 minutes, at least 75 minutes, at least 90 minutes, at least 2 hours, at least 6 hours, at least 12 hours, at least 1 day, at least 4 days, at least 1 week, at least 2 weeks, at least 3 weeks, at least 4 weeks, at least 5 weeks, or at least 6 weeks after the cardiac event, such as any cardiac ischemia-reperfusion. In some versions, the period of time comprises a point in time within 5 minutes, within 10 minutes, within 30 minutes, within 45 minutes, within 60 minutes, within 75 minutes, within 90 minutes, within 2 hours, within 6 hours, within 12 hours, within 1 day, within 4 days, within 1 week, within 2 weeks, within 3 weeks, within 4 weeks, within 5 weeks, within 6 weeks, within 7 weeks, within 8 weeks, within 4 months, within 6 months, within 8 months, within 10 months, within 12 months, within 2 years, within 5 years, within 10 years, or within 20 years of the cardiac event, such as any cardiac ischemia-reperfusion.

The period of time can span a period of at least 6 hours, at least 12 hours, at least 28 hours, at least 24 hours, at least 3 days, at least a week, at least two weeks, at least a month, at least two months, at least 6 months, at least 9 months, at least 1 year, at least 2 years, at least 5 years, at least 10 years, or at least 20 years. There is no theoretical limit to the length of the period of time. The period of time can extend for as long as the subject is alive.

The succinate dehydrogenase inhibitor can be administered continuously or intermittently (non-continuously) over the period of time. If intermittently, the succinate dehydrogenase inhibitor can be administered, for example, 1, 2, 3, 4, 5, or more times a day, 1, 2, 3, 4, 5, 6, 7, 10, 14, or more times a week, 5, 10, 15, 30, or more times a month, etc. The intermittent administration can be performed acutely, e.g., by injection, or over time, e.g., infusion. In some versions, the intermittent administration comprises delivering the succinate dehydrogenase inhibitor to the subject at least one or more times a day, one or more times every 2 days, one or more times every 3 days, one or more times every 4 days, one or more times every 5 days, one or more times every 6 days, one or more times a week, one or more times every two weeks, one or more times every three weeks, one or more times a month, or one or more times every two months.

The succinate dehydrogenase inhibitor can include any compound capable of inhibiting succinate dehydrogenase. Succinate dehydrogenase is also known as succinate-coenzyme Q reductase (SQR), succinate-ubiquinone oxidoreductase, respiratory complex II, and complex II and has activity under EC number 1.3.5.1. Succinate dehydrogenase inhibitors are well known in the art.

Two classes of succinate dehydrogenase inhibitors include succinate-analog inhibitors and ubiquinone-type inhibitors.

Succinate-analog inhibitors are succinate dehydrogenase inhibitors that bind in the succinate pocket of succinate dehydrogenase. Exemplary succinate-analog inhibitors include malonate compounds, TCA cycle intermediates such as malate and oxaloacetate, and any malate or oxaloacetate acids, salts, ions, or esters. Malonate compounds include compounds having the following structure:

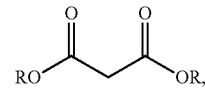

wherein each R is independently H, alkyl (e.g., C1-C6 alkyl), absent (in which case each 0 carries a negative charge), or a cation ionically bound to the oxygen (which is negatively charged). Malonate compounds include malonic acids, malonate ion, malonate salts, and malonate esters. Malonic acids are compounds in which at least one R is H. Malonate ions are compounds in which at least one R is absent. Malonate salts are compounds in which at least one R is a cation. Exemplary malonate salts include disodium malonate ($Na_2(C_3H_2O_4)$). Malonate esters are compounds in which at least one R is alkyl. Exemplary malonate esters include diethyl malonate (($C_2H_5)_2(C_3H_2O_4)$) and dimethyl malonate (($CH_3)_2(C_3H_2O_4)$).

Ubiquinone-type inhibitors are succinate dehydrogenase inhibitors that bind in the ubiquinone pocket of succinate dehydrogenase. Exemplary ubiquinone-type inhibitors include atpenins (e.g., atpenin A4, atpenin A5, atpenin B), carboxin (5,6-dihydro2-methyl-N-phenyl-1,4-oxathiin-3-carboxamide), and thenoyltrifluoroacetone (4,4,4-trifluoro-1-(2-thienyl)-1,3-butanedione) (Miyadera H, Shiomi K, Ui H, Yamaguchi Y, Masuma R, Tomoda H, Miyoshi H, Osanai A, Kita K, Omura S. Atpenins, potent and specific inhibitors of mitochondrial complex II (succinate-ubiquinone oxidoreductase). *Proc Natl Acad Sci USA.* 2003 Jan. 21; 100 (2):473-7).

Additional exemplary succinate dehydrogenase inhibitors include 2-heptyl-4-hydroxyquinoline N-oxide (Miyadera H, Shiomi K, Ui H, Yamaguchi Y, Masuma R, Tomoda H, Miyoshi H, Osanai A, Kita K, Omura S. Atpenins, potent and specific inhibitors of mitochondrial complex II (succinate-ubiquinone oxidoreductase). *Proc Natl Acad Sci USA*. 2003 Jan. 21; 100(2):473-7), harzianopyridone (Miyadera H, Shiomi K, Ui H, Yamaguchi Y, Masuma R, Tomoda H, Miyoshi H, Osanai A, Kita K, Omura S. Atpenins, potent and specific inhibitors of mitochondrial complex II (succinate-ubiquinone oxidoreductase). Proc Natl Acad Sci USA. 2003 Jan. 21; 100(2):473-7), lonidamine (1-(2,4-dichlorobenzyl)-1H-indazole-3-carboxylic acid) (Lili Guo, Alexander A Shestov, Andrew J Worth, Kavindra Nath, David S Nelson, Dennis B Leeper, Jerry D Glickson, Ian A Blair. Inhibition of Mitochondrial Complex II by the Anticancer Agent Lonidamine. *J Biol Chem*. 2016 Jan. 1; 291(1):42-57), diphenyl ether-containing pyrazole-carboxamides (Li Xiong, Hua Li, Li-Na Jiang, Jing-Ming Ge, Wen-Chao Yang, Xiao Lei Zhu, and Guang-Fu Yang. Structure-Based Discovery of Potential Fungicides as Succinate Ubiquinone Oxidoreductase Inhibitors. *J. Agric. Food Chem*. 2017, 65, 5, 1021-1029), among others (B van de Water, J P Zoeteweij, H J de Bont, J F Nagelkerke. Inhibition of succinate: ubiquinone reductase and decrease of ubiquinol in nephrotoxic cysteine S-conjugate-induced oxidative cell injury. *Mol Pharmacol*. 1995 November; 48(5):928-37). A common moiety in succinate dehydrogenase inhibitors is the β-dicarbonyl moiety, which is present in both malonate compounds and atpenin compounds.

Structures herein rendered without indicated stereochemistry include all stereoisomers thereof, in any ratio (i.e., enantiomers and diasteriomers, racemic mixtures thereof, or any mixture at any enantiomeric/diasteriomeric excess).

A "salt" is any acid or base addition salt. The salts herein are preferably pharmaceutically suitable salts. A "pharmaceutically suitable salt" is any acid or base addition salt whose counter-ions are non-toxic to a patient (including a veterinary patient) in pharmaceutical doses of the salts, so that the beneficial pharmacological effects inherent in the free base or free acid are not vitiated by side effects ascribable to the counter-ions. A host of pharmaceutically suitable salts are well known in the art. For basic active ingredients, all acid addition salts are useful as sources of the free base form even if the particular salt, per se, is desired only as an intermediate product as, for example, when the salt is formed only for purposes of purification, or identification, or when it is used as intermediate in preparing a pharmaceutically suitable salt by ion exchange procedures. Pharmaceutically suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. The terms "pharmaceutically acceptable" and "pharmaceutically suitable" are used interchangeably herein.

In the course of the methods of the present invention, a therapeutically effective amount of a succinate dehydrogenase inhibitor of the invention can be administered to an animal, including mammals and humans, in many ways. In some versions, the succinate dehydrogenase inhibitor is systemically administered. In some versions, the succinate dehydrogenase inhibitor is locally administered directly to the heart or myocardial lesion. In some versions, the succinate dehydrogenase inhibitor is orally administered. In some versions, the succinate dehydrogenase inhibitor is parenterally administered. In some versions, the succinate dehydrogenase inhibitor is administered by injection. In some versions, the succinate dehydrogenase inhibitor is administered by infusion. In some versions, the succinate dehydrogenase inhibitor is administered topically. In some versions, the succinate dehydrogenase inhibitor is administered via an aerosol.

For oral administration, the effective amount of succinate dehydrogenase inhibitor may be administered in, for example, a solid, semi-solid, liquid, or gas state. Specific examples include tablet, capsule, powder, granule, solution, suspension, syrup, and elixir agents. The succinate dehydrogenase inhibitors are not limited to these forms.

To formulate the succinate dehydrogenase inhibitor of the invention into tablets, capsules, powders, granules, solutions, or suspensions, the succinate dehydrogenase inhibitor is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the succinate dehydrogenase inhibitor of the invention may be administered rectally or by injection or infusion. For rectal administration, a suppository may be used. The suppository may be prepared by mixing the succinate dehydrogenase inhibitor of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection or infusion, the succinate dehydrogenase inhibitor of the present invention may be injected or infused hypodermically, intracutaneously, intravenously, intraarterially, or intramuscularly. In some versions, the succinate dehydrogenase inhibitor is injected or infused directly into the heart, such as with a syringe or a catheter. In some versions, the succinate dehydrogenase inhibitor infused into the heart via a catheter fed through the femoral artery. In some versions, the succinate dehydrogenase inhibitor is injected or infused through the femoral artery. Medicinal drugs for such injection may be prepared by dissolving, suspending or emulsifying the succinate dehydrogenase inhibitor of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

In some versions, the succinate dehydrogenase inhibitor is administered via a patch, which can be placed directly on heart, such as on the myocardial lesion, and locally absorbed, or placed anywhere else on the body and systemically absorbed.

To formulate the succinate dehydrogenase inhibitor of the invention into suspensions, syrups, or elixirs, a pharmaceutically suitable solvent may be used. Included among these is the non-limiting example of water.

The succinate dehydrogenase inhibitor of the invention may also be used together with an additional compound having other pharmaceutically suitable activity to prepare a medicinal drug. A drug, either containing a succinate dehydrogenase inhibitor of the invention as a stand-alone compound or as part of a composition, may be used in the treatment of subjects in need thereof.

The succinate dehydrogenase inhibitor of the invention may also be administered in the form of an aerosol or inhalant prepared by charging the succinate dehydrogenase inhibitor in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

The succinate dehydrogenase inhibitor of the invention may be administered to an animal, including mammals and humans, in need thereof as a pharmaceutical composition, such as tablets, capsules, solutions, or emulsions. Administration of other forms of the succinate dehydrogenase inhibitor of the invention, including but not limited to esters thereof, pharmaceutically suitable salts thereof, metabolites thereof, structurally related compounds thereof, analogs thereof, and combinations thereof, in a single dose or a multiple dose, are also contemplated by the present invention.

The succinate dehydrogenase inhibitor of the invention can also be administered topically, such as directly to the infarct or injury itself. The succinate dehydrogenase inhibitor of the invention can be topically administered directly on the infarct or injury itself via a patch or other delivery mechanism surgically placed, for example, directly on the infarct or injury.

The succinate dehydrogenase inhibitor of the invention can also be administered topically in a manner that reaches the bloodstream, such as through a skin or mucosal patch.

The terms "preventing," "treating," or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The succinate dehydrogenase inhibitor of the invention is preferably used and/or administered in the form of a composition. Suitable compositions are, preferably, a pharmaceutical composition, a food composition, or a food supplement. These compositions provide a convenient form in which to deliver the succinate dehydrogenase inhibitor. Compositions of the invention may comprise an antioxidant in an amount effective to increase the stability of the succinate dehydrogenase inhibitor with respect to oxidation or solubility.

The amount of the succinate dehydrogenase inhibitor that is administered in the method of the invention or that is for administration in the use of the invention is any suitable amount. In some versions, the amount is 1 ng/kg body weight to 20 g/kg body weight, such as 1 µg/kg body weight to 1 g/kg body weight, or 1 mg/kg body weight to 100 mg/kg body weight of the succinate dehydrogenase inhibitor per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, beads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the succinate dehydrogenase inhibitor on the subject.

Pharmaceutically acceptable carriers suitable for use in such compositions are well known in the art of pharmacy. The compositions of the invention may contain 0.01-99% by weight of the succinate dehydrogenase inhibitor of the invention. The compositions of the invention are generally prepared in unit dosage form. In some versions, the unit dosage of succinate dehydrogenase inhibitor is from 0.1 mg to 2000 mg, such as 50 mg to 1000 mg. The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like. In some versions, the unit dosage of the succinate dehydrogenase inhibitor is from 0.1 mg to 2000 mg, more preferably from 50 mg to 1000 mg.

In general, the term carrier may be used throughout this application to represent a composition with which the succinate dehydrogenase inhibitor may be mixed, be it a pharmaceutical carrier, foodstuff, nutritional supplement, or dietary aid. The materials described above may be considered carriers for the purposes of the invention. In certain embodiments of the invention, the carrier has little to no biological activity on the succinate dehydrogenase inhibitor of the invention.

Dose: The methods of the present invention can comprise administering a therapeutically effective amount of the succinate dehydrogenase inhibitor to an animal in need thereof. The effective amount of the succinate dehydrogenase inhibitor depends on the form of the succinate dehydrogenase inhibitor administered, the duration of the administration, the route of administration (e.g., oral or parenteral), the age of the animal, and the condition of the animal, including mammals and humans.

In certain other embodiments, the present invention provides for the use of the succinate dehydrogenase inhibitor and also structurally related compounds, such as esters thereof, pharmaceutically suitable salts thereof, metabolites thereof, structurally related compounds thereof, or combinations thereof.

When practiced, the methods of the invention can be by way of administering the succinate dehydrogenase inhibitor to a subject via any acceptable administration route using any acceptable form, as is described above, and allowing the body of the subject to distribute the succinate dehydrogenase inhibitor to the target cell through natural processes. As is described above, administering can likewise be by direct injection to a site (e.g., organ, tissue) containing a target cell (i.e., a cell to be treated).

Furthermore, administering can follow any number of regimens. It thus can comprise a single dose or dosing of the succinate dehydrogenase inhibitor, or multiple doses or dosings over a period of time. Accordingly, treatment can comprise repeating the administering step one or more times until a desired result is achieved. In certain embodiments, treating can continue for extended periods of time, such as weeks, months, or years. Dosing regimens can entail administration of the succinate dehydrogenase inhibitor between 6 times daily to once per week, with some regimens being between three times daily to once daily. Those of skill in the art are fully capable of easily developing suitable dosing regimens for individuals based on known parameters in the art. The dosage amounts for the succinate dehydrogenase inhibitor of the invention may be used in the methods of these embodiments of the invention.

The amount to be administered will vary depending on the subject, stage of disease or disorder, age of the subject, general health of the subject, and various other parameters known and routinely taken into consideration by those of skill in the medical arts. As a general matter, a sufficient amount of the succinate dehydrogenase inhibitor will be administered in order to make a detectable change. Suitable amounts are disclosed herein, and additional suitable amounts can be identified by those of skill in the art without undue or excessive experimentation, based on the amounts disclosed herein.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1

Targeting Metabolism to Stimulate Adult Heart Regeneration

Cardiovascular diseases are a major cause of morbidity and mortality in the world[1]. This is due to the inability of the adult mammalian heart to replace damaged tissue following injury. Existing heart failure therapy focuses on prevention of the progressive weakening of heart muscle following injury, and the current best option for end-stage heart failure is transplantation[2]. However, this remains an impractical approach for most patients due to the surgical complexity of heart transplantations and the limited availability of donors[3,4]. Thus, novel approaches for regenerating or repairing damaged heart tissue following injury would represent a radically improved outcome. Until recently, complete heart regeneration following injury has been observed only in non-mammalian vertebrates[5-8]. Recently we demonstrated that neonatal mice are capable of regenerating their hearts following myocardial infarction (MI) for a brief window of a few days after birth[9-11]. This finding leads to renewed hope that mechanisms already in place in mammals could be activated to stimulate adult heart regeneration.

During the transition from embryonic/neonatal to an adult state, cardiomyocytes undergo a metabolic switch in response to atmospheric oxygen[12]. Both embryonic and neonatal cardiomyocytes generate energy through glycolysis, whereas adult cardiomyocytes generate energy through oxidative phosphorylation via mitochondrial respiration[13,14]. One outcome of this metabolic switch is a significant increase in reactive oxygen species (ROS) production from the mitochondria. This increase in ROS levels causes DNA damage, contributes to the shutdown of cardiac developmental pathways that regulate cardiomyocyte formation, and results in inhibition of cardiomyocyte proliferation[15]. What regulates this metabolic switch, and whether intervention in this process can alter the dynamics of the cardiac regenerative response following injury has been relatively unexplored. Current evidence suggests that elevated ROS production in ischemic tissues occurs due to accumulation of the mitochondrial metabolite succinate[16]. Thus, we hypothesized that changes in oxygen levels following birth might trigger succinate accumulation and ROS production, which contributes to cardiomyocyte cell-cycle exit in the postnatal heart. Our results demonstrate that injection of succinate in the neonatal mouse heart results in inhibition of neonatal cardiomyocyte proliferation and regeneration. More importantly, inhibition of succinate dehydrogenase (SDH) by malonate treatment after birth extends the window of cardiomyocyte proliferation and regeneration in juvenile mice. Surprisingly, malonate treatment of the adult mouse heart results in complete restoration of cardiac structure and function following MI. Our results are the first to address the role of individual metabolites in regulating cardiomyocyte proliferation and cardiac regeneration, which lead to key mechanistic insights and novel therapies for adult heart disease as described herein. The invention provides the use of malonate and other succinate dehydrogenase inhibitors to metabolically reprogram the adult mammalian heart to a regenerative state. The invention provides a metabolic treatment for adult myocardial infarction. The invention provides a therapeutic use of malonate and other succinate dehydrogenase inhibitors in alleviating adult heart failure.

Cardiac Regeneration

Cardiovascular diseases remain the leading cause of death in the world[1,17]. Both vascular damage and myocardial damage arise from acute cardiovascular events such as myocardial infarction (MI). The limited capacity of the mammalian heart to repair itself represents a major barrier in cardiovascular medicine and often leads to heart failure. Current advances in therapy such as coronary revascularization has led to a reduction in the high rates of mortality. However, non-lethal cardiac injuries result in the increased numbers of cardiomyopathy[18]. Without rigorous risk management and medications, these cardiac injuries often result in reduced heart function and lead to the development of heart failure. Currently, there are no long-term treatments for this major health burden[2]. This underscores the enormous need for new approaches for treatment of adult heart disease. Identifying molecular mechanisms that can promote endogenous regeneration and restoration of cardiac contractile function is essential to identifying novel therapeutic targets for heart failure.

Recently we demonstrated that neonatal mice can regenerate approximately 15 percent of their hearts following injury, and that the newly formed cardiac tissue is derived primarily from the proliferation of the preexisting cardiomyocytes[9-11]. Interestingly, this robust regenerative response has been demonstrated to be mediated by activation of pathways necessary for cardiac development that regulate cardiomyocyte cell cycle activity1[9-24]. In addition, several studies using different animal models demonstrate that the endogenous cardiac regenerative response involves evolutionarily conserved mechanisms of regeneration across many species such as zebrafish, neonatal mice, and neonatal pigs[25-31]. It may be possible to reactivate heart renewal mechanisms in adult mammals in order to regenerate the injured heart, restore lost myocardial tissue and increase contractile heart function following adult cardiac injury. Thus, understanding the fundamental pathways of heart renewal and regeneration is critical for development of novel therapies for heart disease.

Mitochondria and Heart Regeneration

The heart is the most energy consuming tissue (per gram) in the human body[32], and energy production takes place in the mitochondria. The main function of the mitochondria is generating energy as adenosine triphosphate (ATP) and as a consequence mitochondria play an essential role during development, cellular proliferation, and tissue regeneration, which are energy demanding processes[33-35]. Zebrafish and neonatal mouse hearts have lower mitochondrial DNA copy number compared to postnatal and adult mice[15]. Exposure to atmospheric oxygen following birth results in a metabolic switch in energy utilization in cardiomyocytes[12]. Both embryonic and neonatal cardiomyocytes generate energy through glycolysis, while adult cardiomyocytes generate energy through oxidative phosphorylation via mitochondrial respiration[13,14]. Recent evidence suggests that exposure to high levels of atmospheric oxygen following birth and a subsequent metabolic switch results in increased levels of mitochondrial reactive oxygen species (ROS) production that causes cardiomyocyte DNA damage and contributes to the postnatal cardiomyocyte cell cycle arrest in mice (FIG. 1)[15]. Interestingly, fate mapping of cycling cardiomyocytes in the adult mammalian heart demonstrated that the few proliferative cardiomyocytes are hypoxic and exhibit low oxidative DNA damage[36]. More importantly, exposing adult mice to low oxygen levels in hypoxic chambers resulted in lower cardiomyocyte ROS production, increased cardiomyocyte cell cycle activity, and higher regenerative potential following injury[37]. Furthermore, a recent study demonstrated that activation of glycolysis regulates cardiomyocyte proliferation in the regenerating zebrafish heart[38]. Collectively, this reveals an important role for cardiomyocyte metabolism during heart regeneration. Thus, it is important to understand the metabolic state and the dynamics of cardiomyocyte ROS production in the mammalian heart following birth, which can lead to important insights towards restoring cardiomyocyte cell cycle activity and subsequent regenerative abilities following injury.

Mitochondria, ROS Production, and Succinate Metabolism

Figure 2:
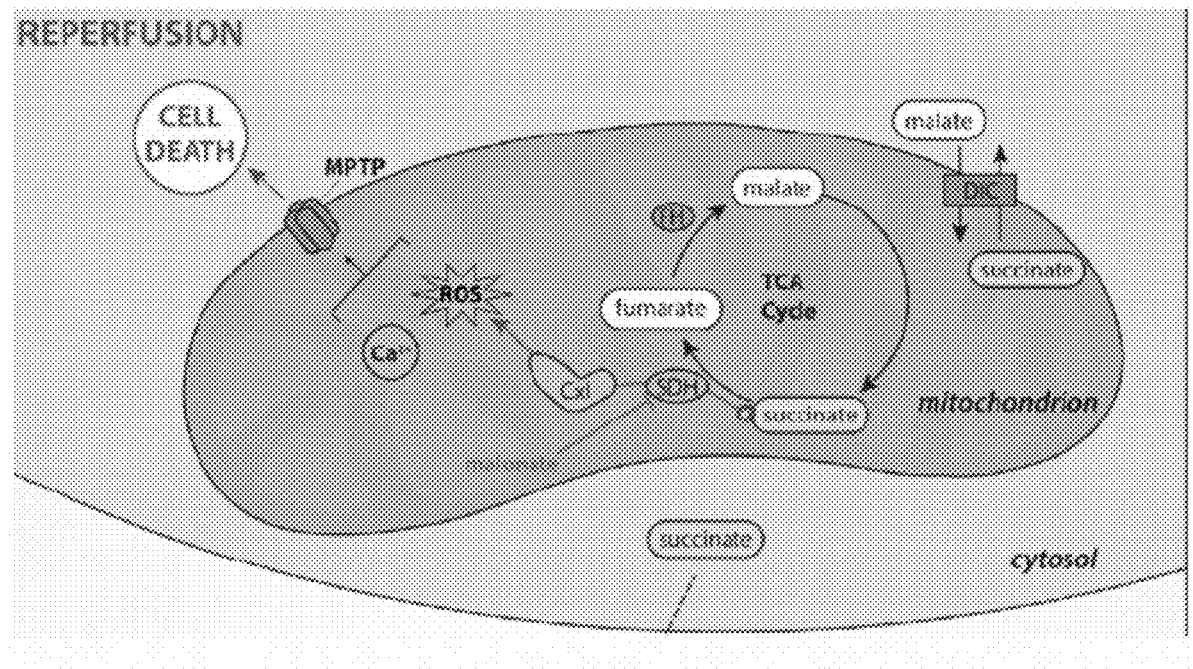
FIG. 2. Succinate metabolism drives ROS production ischemia/reperfusion (IR) injury. During reperfusion injury, the accumulated succinate is oxidized by SDH, which produces a highly reduced coenzyme Q pool. This results in a significant increase in ROS production through complex I (CxI). Modified from Kula-Alwar et al. 2019 (Duvaraka Kula-Alwar, Hiran A Prag, Thomas Krieg. Targeting succinate metabolism in ischemia/reperfusion injury. Circulation. 2019 Dec. 10; 140(24): 1968-1970).

Mitochondrial ROS are generated by the electron transport chain (ETC), which is composed of mitochondrial respiratory complexes I-IV[39-41]. ROS production is significantly increased following ischemic heart injury, which results from the blockade of coronary blood flow to the myocardium. Percutaneous coronary intervention or thrombolysis can lead to reperfusion of the ischemic region and prevent the development of infarction. However, the restoration of blood flow itself induces cardiomyocyte death. This event is known as ischemia/reperfusion (IR) injury[42]. The initial ischemic insult causes a cardiomyocyte metabolic shift to anaerobic glycolysis, and the subsequent re-oxygenation causes IR injury due to a large burst of mitochondrial ROS production[43,44]. Interestingly, recent studies have demonstrated that the metabolite succinate is accumulated during ischemic insults in multiple tissues, including the heart[16]. Subsequently, the high levels of succinate are then oxidized by the enzyme complex succinate dehydrogenase (SDH, also known as complex II), which results in a burst of ROS production by mitochondrial complex I that results in the IR injury (FIG. 2)[16,45]. Administration of the SDH competitive inhibitor malonate during reperfusion prevented the accumulation of succinate and reduced the extent of the IR injury[46, 47]. These results revealed that the competitive inhibition of SDH by malonate prevents succinate oxidation and blocks the production of high levels of ROS during IR injury. The dynamics of ROS production in postnatal cardiomyocytes, which contributes to cardiomyocyte cell cycle exit and loss of the cardiac regenerative ability remains poorly understood. This underscores the need for elucidating the role of mitochondrial metabolites in cardiomyocyte ROS production, which can have important therapeutic effects beyond IR injury.

We hypothesized that the switch from the low oxygen environment during development to the high levels of atmospheric oxygen at birth might trigger an increase in succinate buildup and subsequent oxidation, followed by a surge in ROS production that results in cardiomyocyte DNA damage and cell cycle exit. We wanted to determine whether succinate inhibits cardiomyocyte proliferation and regeneration in the early neonatal regenerative window, and whether the competitive inhibition of SDH by malonate can promote adult cardiomyocyte cell cycle activity.

Our results demonstrate that injection of succinate inhibits cardiomyocyte proliferation in the neonatal mouse heart following injury, which results in blockade of the neonatal cardiac regenerative response. Furthermore, our results demonstrate that inhibition of SDH by malonate after birth extends the neonatal cardiomyocyte proliferation window, which results in heart regeneration in juvenile 7-day-old mice following injury. Interestingly, mitochondrial ROS scavenging by MitoQ did not recapitulate the regenerative effect of malonate. Thus, we wanted to determine whether SDH inhibition by malonate can promote adult heart regeneration. To our surprise, SDH inhibition by malonate resulted in complete cardiac regeneration in the adult mouse heart following MI at the structural and functional level. These results reveal a novel role for SDH inhibitors in regulating cardiomyocyte proliferation and regeneration in the postnatal heart.

The present examples identify the mechanisms by which malonate regulates adult cardiomyocyte proliferation and heart regeneration using adult mouse models and human induced pluripotent stem cell derived cardiomyocytes (hiPSC-CMs). The results arising from the experiments show the underlying mechanisms by which malonate treatment provides a cure for heart failure patients.

Regenerating the adult mammalian heart is a significant goal in order to overcome the immense health and financial burden of cardiovascular disease in the world. Thus, there is an immense need for out of the box approaches to regenerate the adult heart following injury. We executed experiments showing that modulating metabolism can promote heart tissue regeneration following injury. We demonstrated for the first time that individual mitochondrial metabolites regulate cardiomyocyte cell cycle activity and adult heart regeneration. Our exciting finding that the metabolite malonate promotes cardiomyocyte cell cycle activity and adult heart regeneration following myocardial infarction is very innovative. The present examples show the mechanisms by which malonate metabolically reprograms the adult heart to a regenerative state and stimulates cardiomyocyte proliferation and heart regeneration of the injured heart. We perform comprehensive studies using adult mouse models of heart failure, metabolomics, as well as human induced pluripotent stem cell derived cardiomyocytes to identify how targeting metabolism promotes adult mammalian heart regeneration. The results establish the significance of metabolic regulation of cardiomyocytes as a therapeutic tool for regenerating the adult human heart in heart failure patients with reduced ejection fraction.

Figure 3:
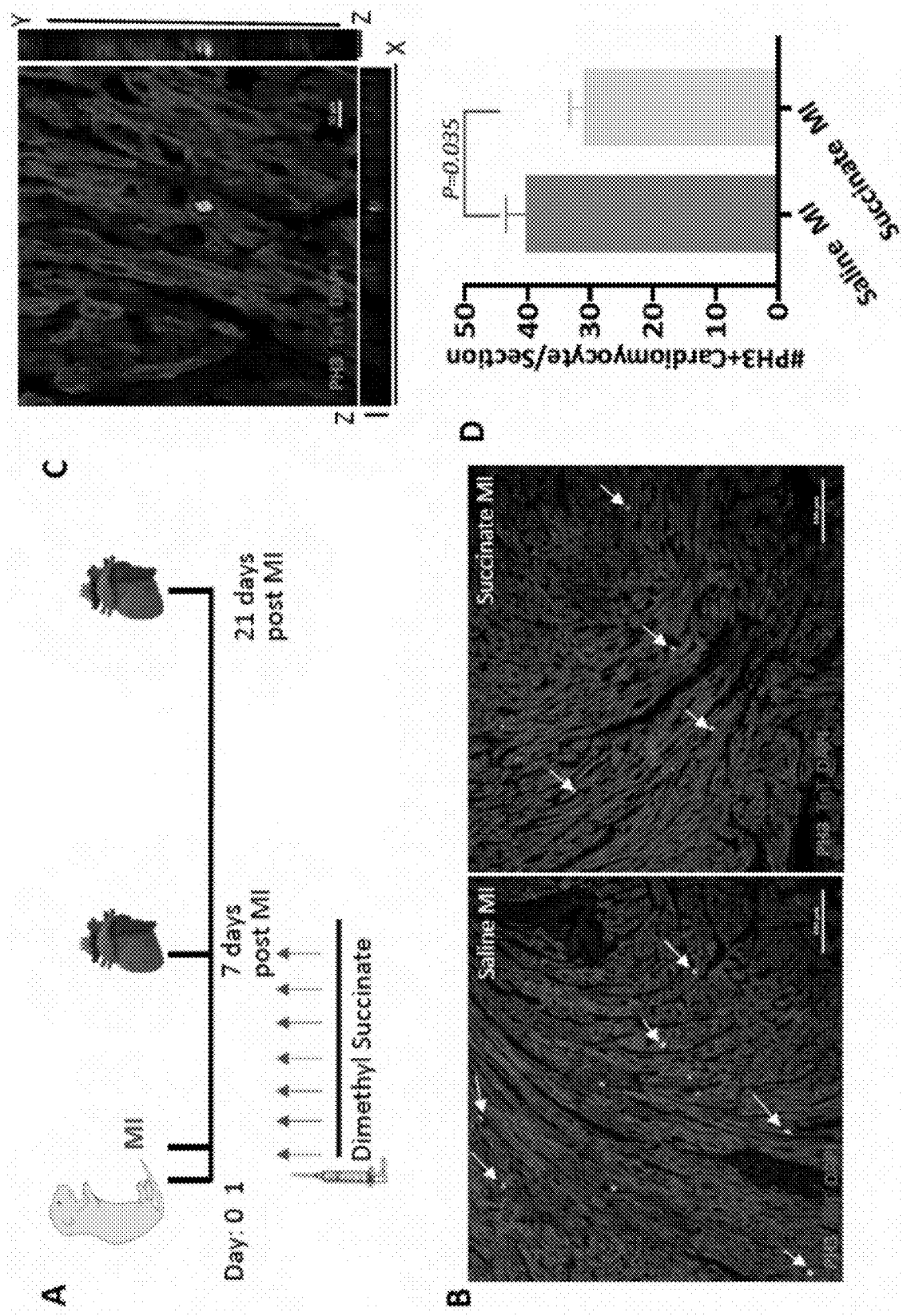
FIG. 3. Succinate reduces cardiomyocyte proliferation in neonatal mice following myocardial infarction (MI). (A) Schematic of injection period and myocardial infarction strategy in neonatal mice. (B) Immunostaining of pH3 and cTnnt showing a significant reduction in the number of mitotic myocytes in succinate-injected mice compared to control hearts at 7 days post-MI. (C) High magnification Z-stack image of a mitotic cardiomyocyte. (D) Quantification of the number of mitotic cardiomyocytes per section showing a significant decrease in cardiomyocyte mitosis following dimethyl succinate injection. (n=5-8 mice per group)
Figure 4:
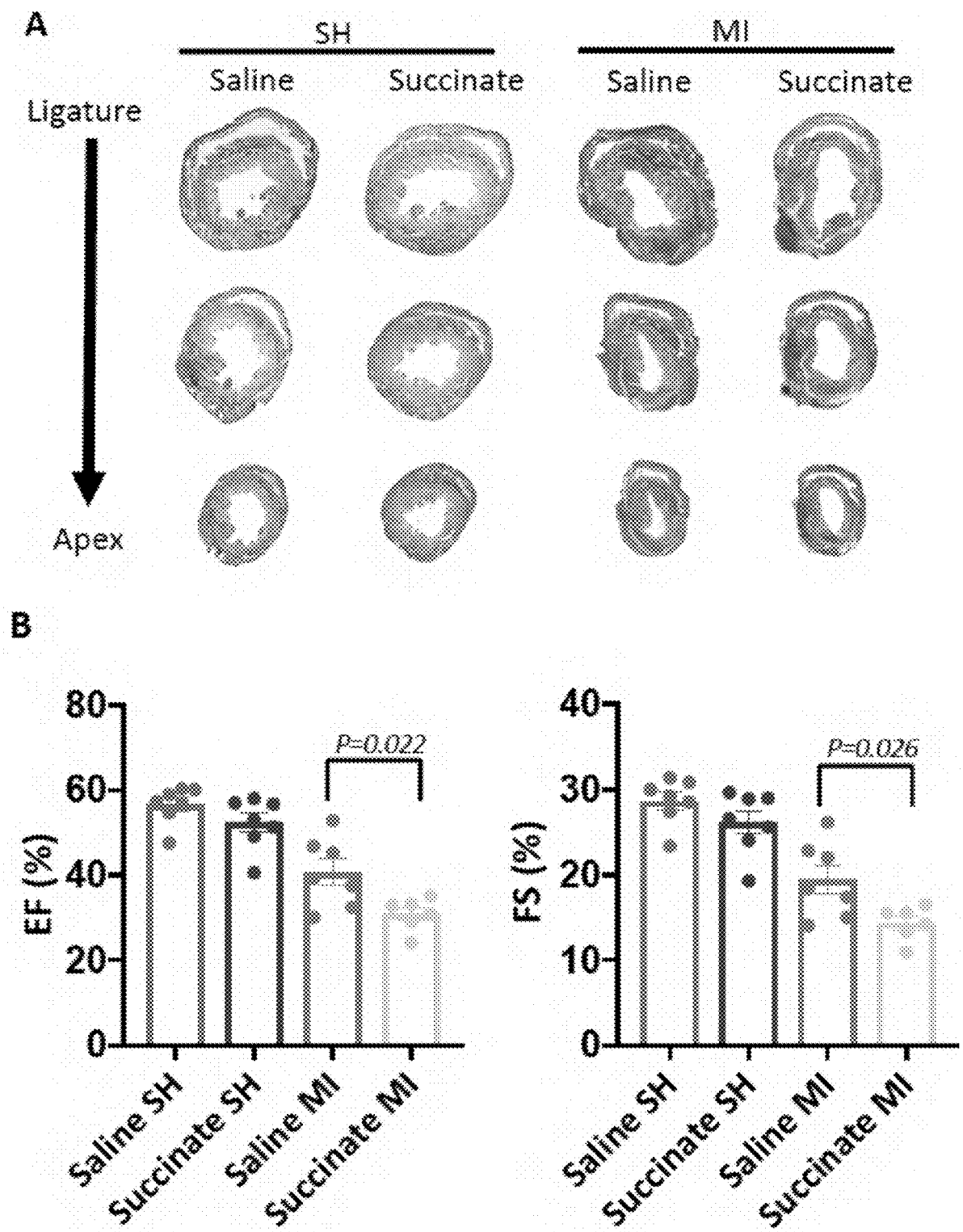
FIG. 4. Succinate blocks neonatal heart regeneration following MI. (A) Trichrome staining demonstrating persistence of the fibrotic scar following MI in the dimethyl succinate-injected mice compared to saline-injected controls. (B) Echocardiography at 21 days post-MI showing a significant reduction in the contractile function of dimethyl succinate-injected mice following MI compared to saline-injected controls as measured by ejection fraction (EF) and fractional shortening (FS). (n=6-7 mice per group)

Succinate Blocks Cardiomyocyte Proliferation and Heart Regeneration Following Myocardial Infarction in Neonatal Mice The neonatal mouse heart has the ability to regenerate following MI due to the proliferative potential of neonatal cardiomyocytes. Within a week after birth, the increase in ROS production in cardiomyocytes results in DNA damage and contributes to cardiomyocyte cell cycle exit. To determine whether an increase in succinate levels reduces cardiomyocyte cell cycle activity and blocks neonatal mouse heart regeneration, neonatal mice were injected intraperitoneally with dimethyl succinate (100 mg/kg) daily for 7 days following myocardial infarction (FIG. 3 (A)). To determine whether succinate reduces cardiomyocyte proliferation, we performed immunostaining of the mitosis marker pH3 at 7 days post-MI. Our results revealed a reduction in cardiomyocyte mitosis in succinate-injected MI hearts compared to controls (FIGS. 3 (B, C, and D)). We tried multiple doses (50, 100, 150 mg/kg) and found that 100 mg/kg was the minimum effective dose that reduces cardiomyocyte proliferation. Our results suggest that high levels of succinate can reduce the cardiomyocyte proliferative potential of neonatal mice, which is the main source of the newly formed cardiomyocytes during cardiac regeneration. To further establish the effects of succinate on neonatal heart regeneration, we performed trichrome staining at 21 days post-MI to assess regeneration and fibrosis in control and succinate-injected mice. As expected, saline-injected control mice demonstrated complete heart regeneration, in contrast to dimethyl succinate-injected mice which showed lack of regeneration and persistence of a fibrotic scar (FIG. 4 (A)). This lack of regeneration was evident in the significant reduction in the contractile function of the hearts of dimethyl succinate-injected mice compared to saline-injected controls as measured by echocardiography (FIG. 4 (B)). Together, these results reveal that succinate injection during the first week of life can results in premature cardiomyocyte cell cycle exit, which results in inhibition of the neonatal cardiac regenerative response.

Figure 5A:
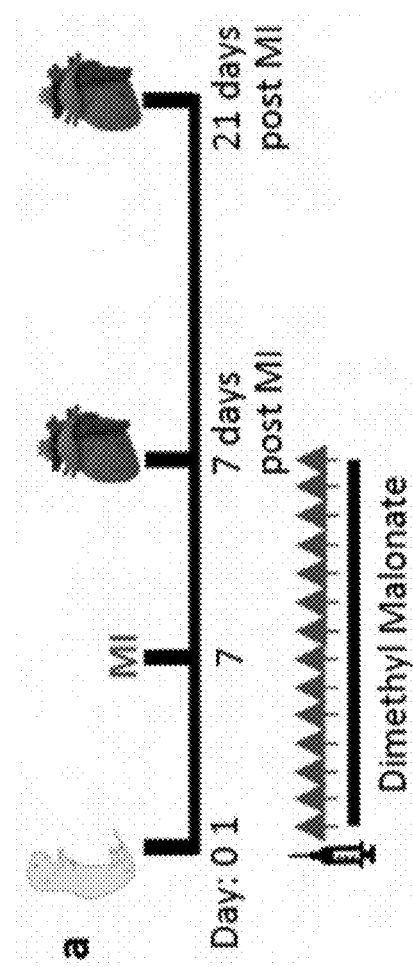
FIGS. 5A-5F. Malonate promotes cardiomyocyte proliferation in the post-natal heart following MI.
Figure 5B:
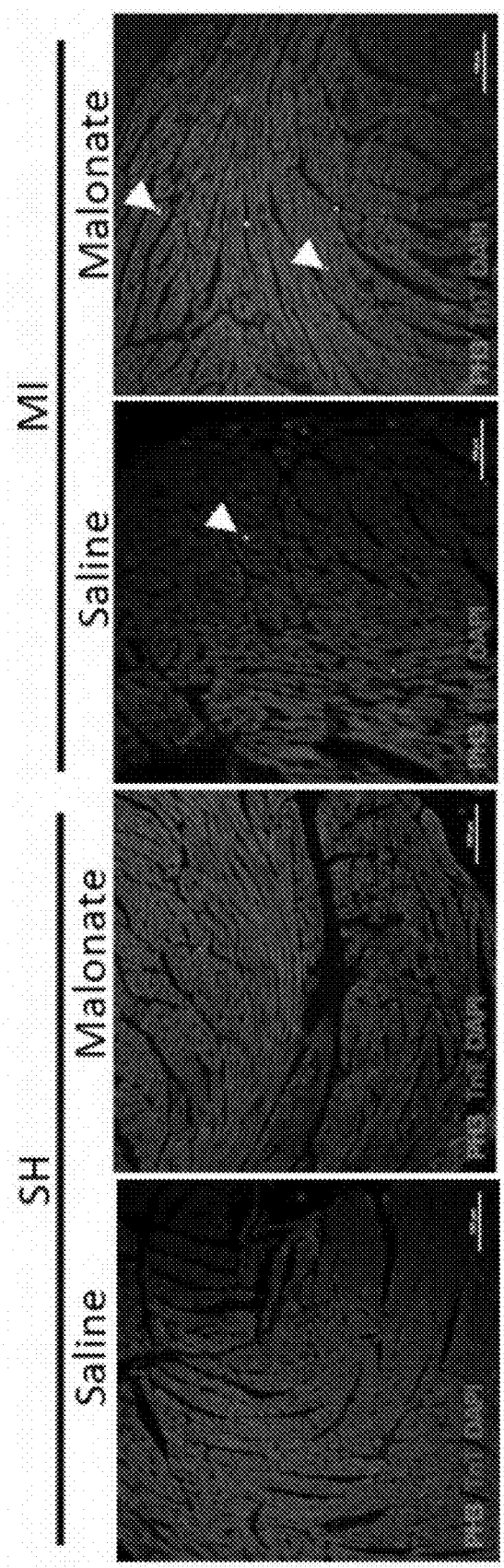
Figure 5C:
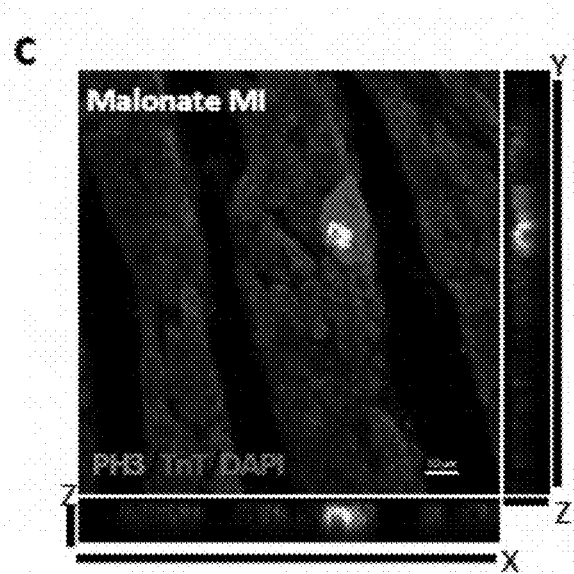
Figure 5D:
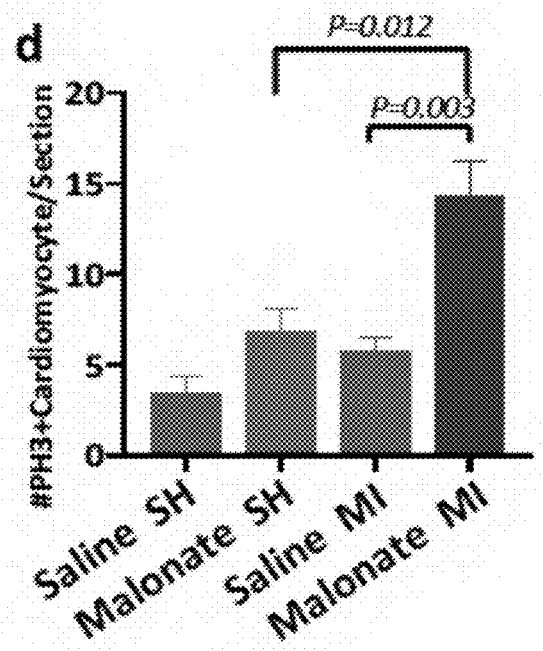
Figure 5E:
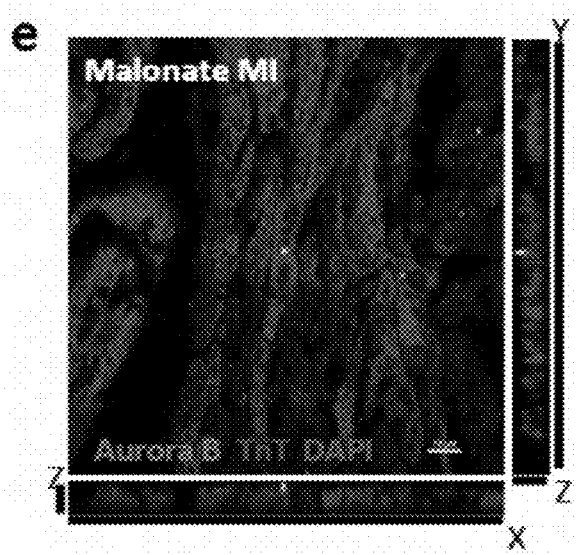
Figure 5F:
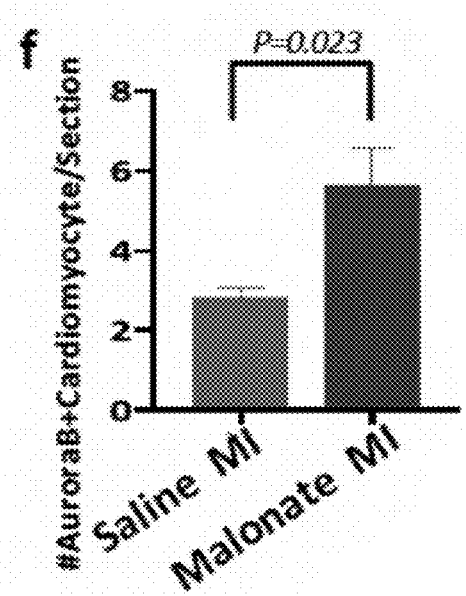
Figure 6:
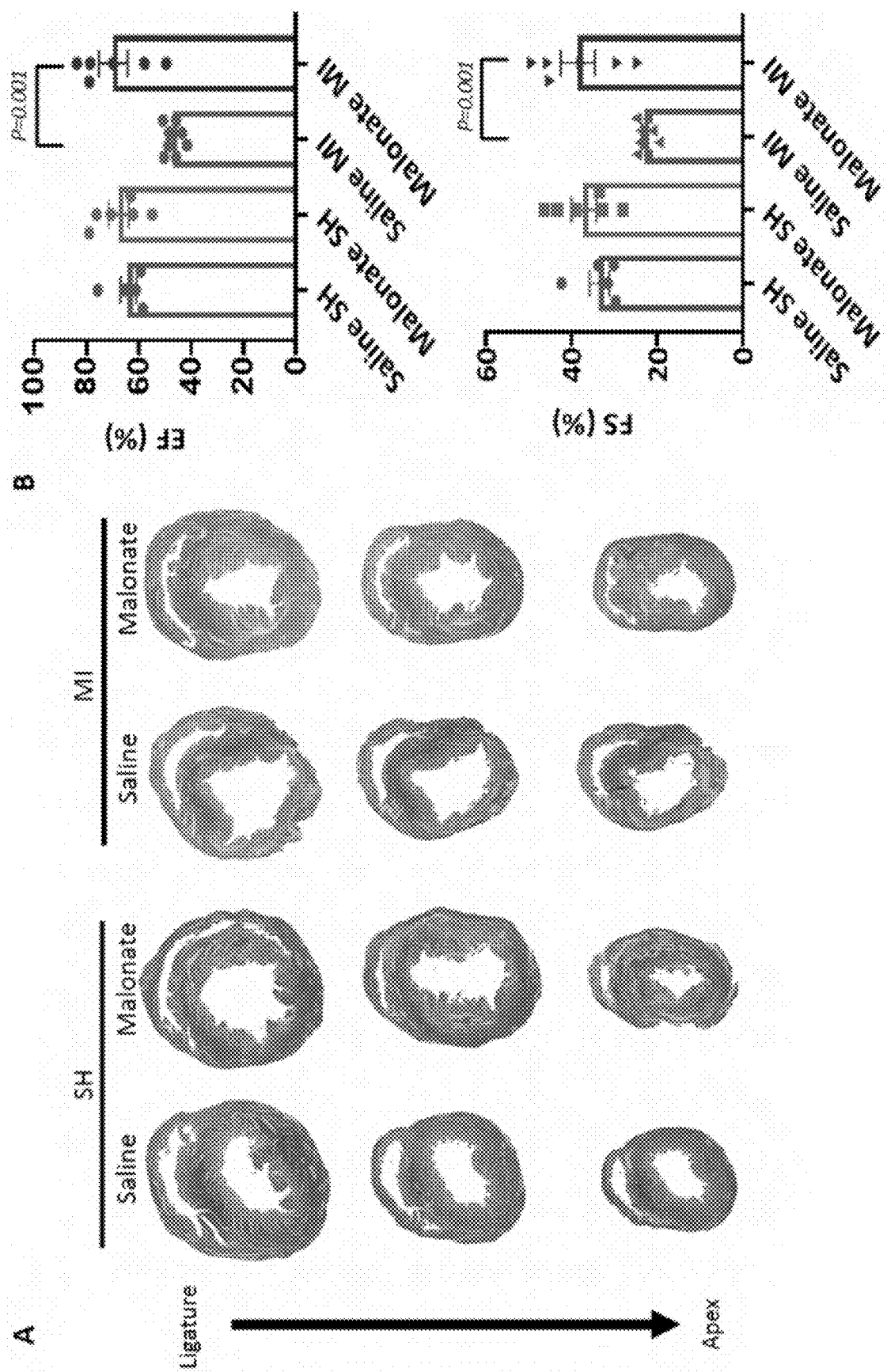
FIG. 6. Malonate promotes cardiomyocyte proliferation in the post-natal heart following MI. (A) Trichrome staining of malonate-injected hearts at 21 days post injury at p'7, showing complete regeneration in malonate-injected mice compared to control. (B) Left ventricular systolic function quantified by SF and EF 3 weeks after MI surgery showed more functional recovery in malonate-injected MI hearts compared to the control. (n=5-8 mice per group)

Malonate, the Succinate Dehydrogenase Competitive Inhibitor, Promotes Cardiomyocyte Proliferation and Regeneration Following Myocardial Infarction Although we demonstrated that exogenous administration of succinate can inhibit cardiomyocyte proliferation and regeneration, it remained unclear whether succinate accumulation in cardiomyocytes contribute to ROS production and cardiomyocyte cell cycle exit in the postnatal heart. To establish whether succinate accumulation plays a role in the loss of cardiomyocyte proliferative potential, we wanted to test whether the exemplary succinate dehydrogenase complex (SDH) competitive inhibitor malonate could extend the cardiomyocyte proliferative window and improve the cardiac regeneration capacity of the juvenile 7-day-old mice. We injected dimethyl malonate (100 mg/kg) intraperitoneally in neonatal mice daily for 2 weeks to prevent the accumulation of endogenous succinate levels postnatally by SDH inhibition. We then analyzed the hearts following injury to determine whether malonate results in prolongation of the neonatal regenerative window (FIG. 5A). To examine whether malonate stimulates cardiomyocyte proliferation, we performed MI in 7-day-old mice and analyzed their hearts at 7 days post-MI by immunostaining for markers of proliferation. We quantified a significant increase in the number of cardiomyocytes undergoing mitosis as evident by pH3 staining in the dimethyl malonate-injected mice compared to controls (FIGS. 5B, 5C, and 5D). Furthermore, we quantified a significant increase in the number of cardiomyocytes undergoing cytokinesis by Aurora B staining, suggesting that a significantly higher number of cardiomyocytes are undergoing complete cell division (FIGS. 5E and 5F). To determine whether this increase in cardiomyocyte proliferation results in improved regeneration in the non-regenerating P7-old mouse heart, we performed trichrome staining at 21 days post-MI to quantify structural regeneration and fibrosis in the dimethyl malonate-injected mice compared to controls. As expected, lack of myocardium regeneration and persistence of fibrotic scarring was detected below the ligature plane of the saline-injected controls. In contrast, mice that were injected with dimethyl malonate demonstrated complete heart regeneration (FIG. 6 (A)). More importantly, systolic function assessed by ejection fraction (EF) and fractional shortening (FS) in the dimethyl malonate-injected hearts was restored to normal levels compared to controls (FIG. 6 (B)). These data indicate that SDH inhibition by malonate can promote cardiomyocyte proliferation and extend the regenerative capacity of the neonatal mouse heart beyond 1 week after birth, resulting in a complete regenerative response following MI in 7-day-old juvenile mice.

Figure 7A:
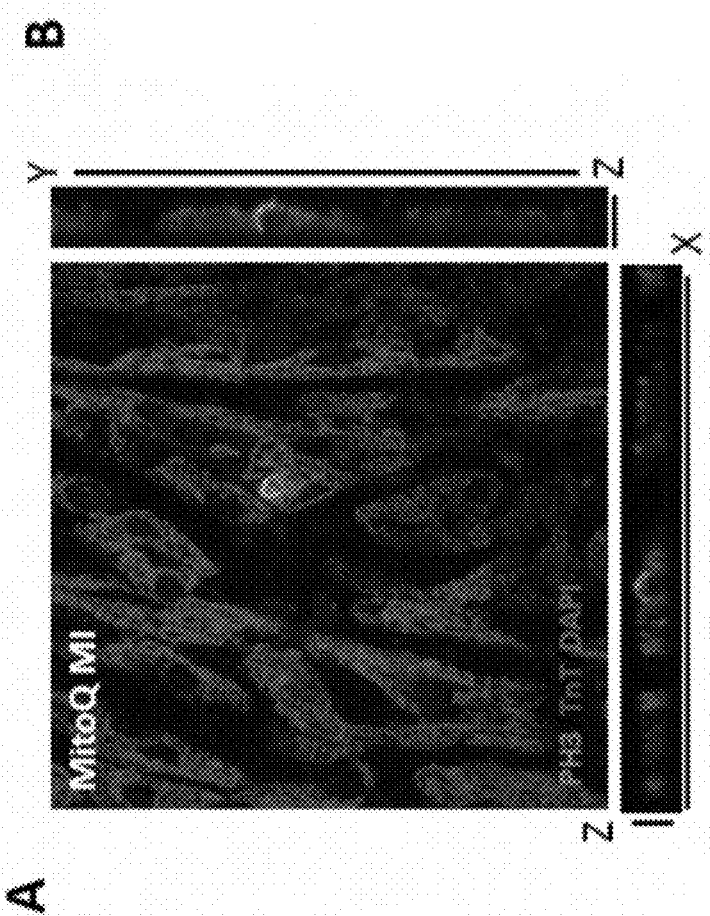
FIGS. 7A-7D. ROS Scavenging by MitoQ promotes cardiac repair but not regeneration.
Figure 7B:
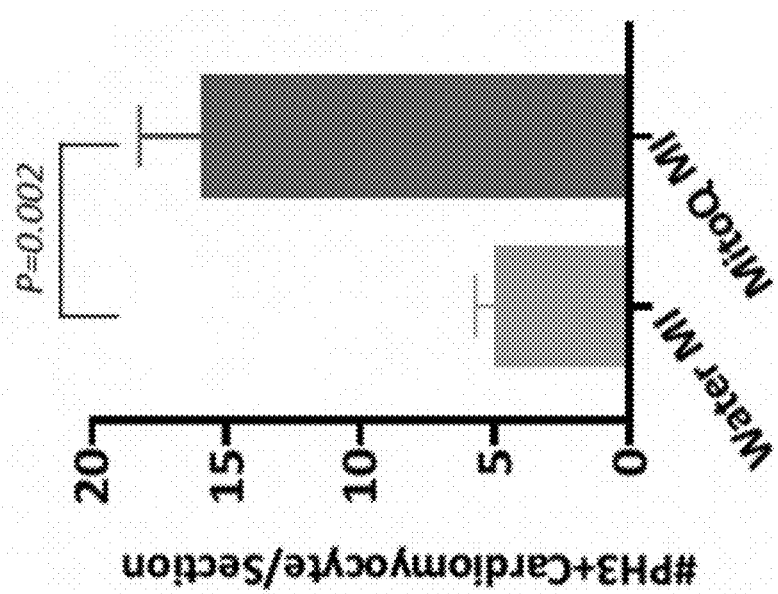
Figure 7D:
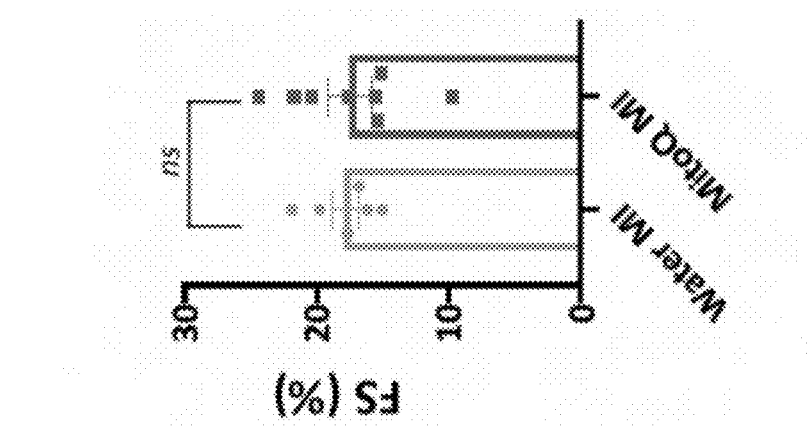
Figure 7D:
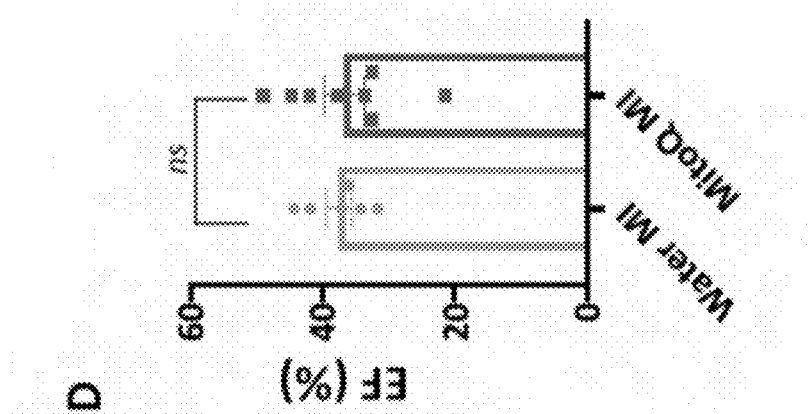
Figure 7C:
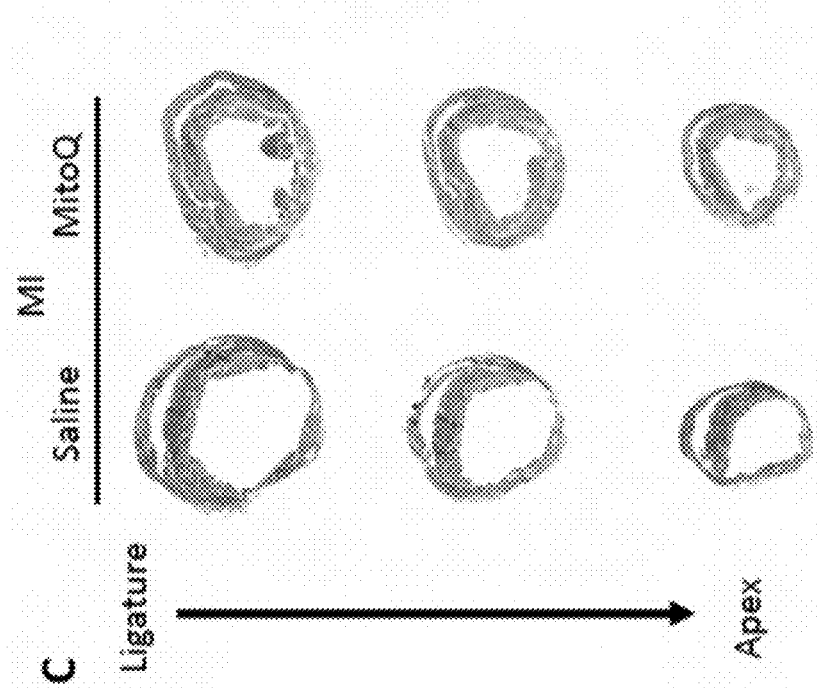

Mitochondrial ROS Scavenging Does Not Recapitulate the Regenerative Potential of Malonate To determine whether malonate extends the regenerative potential of the postnatal mouse heart by preventing succinate accumulation and subsequently reducing mitochondrial ROS production, we injected mice intraperitoneally (IP) with the mitochondria-targeted antioxidant MitoQ after birth. MitoQ can successfully localize to metabolically active cells such as cardiomyocytes and can deplete mitochondrial ROS in vivo[48,49]. This will allow us to determine whether depletion of mitochondrial ROS by MitoQ can mimic the regenerative effect of malonate. Similar to malonate, we injected MitoQ (10 mg/kg) intraperitoneally daily after birth for 2 weeks and performed MI in 7-day-old mice, the timepoint when cardiomyocyte proliferation and regeneration is lost in the postnatal heart. Mice injected with the mitochondrial ROS scavenger MitoQ showed a significant increase in cardiomyocyte mitosis at 7 days post-MI indicated by immunostaining for the mitotic marker pH3 compared to controls (FIGS. 7A-7B). These results confirm previous studies that demonstrate enhanced cardiomyocyte cell cycle activity by reducing ROS levels[15,37]. To further determine whether MitoQ can regenerate the 7-day-old mouse hearts similar to malonate, we performed trichrome staining at 21 days post-MI in both MitoQ-injected mice and controls. Although MitoQ resulted in a smaller scar size, there was no complete myocardium regeneration and the fibrotic scar was still present (FIG. 7C). In addition, echocardiographic measurements demonstrated that there was no improvement in cardiac function of the MitoQ-injected mice compared to controls as measured by EF and FS (FIG. 7D). These results reveal that although mitochondrial specific ROS scavenging by MitoQ can stimulate cardiomyocyte proliferation and promote cardiac repair, MitoQ does not result in complete regeneration or improvement in function similar to malonate. This suggests that malonate stimulates regeneration of the postnatal heart through additional mechanisms than reducing mitochondrial ROS levels alone.

Malonate Promotes Adult Heart Regeneration Following Myocardial Infarction

Figure 8A:
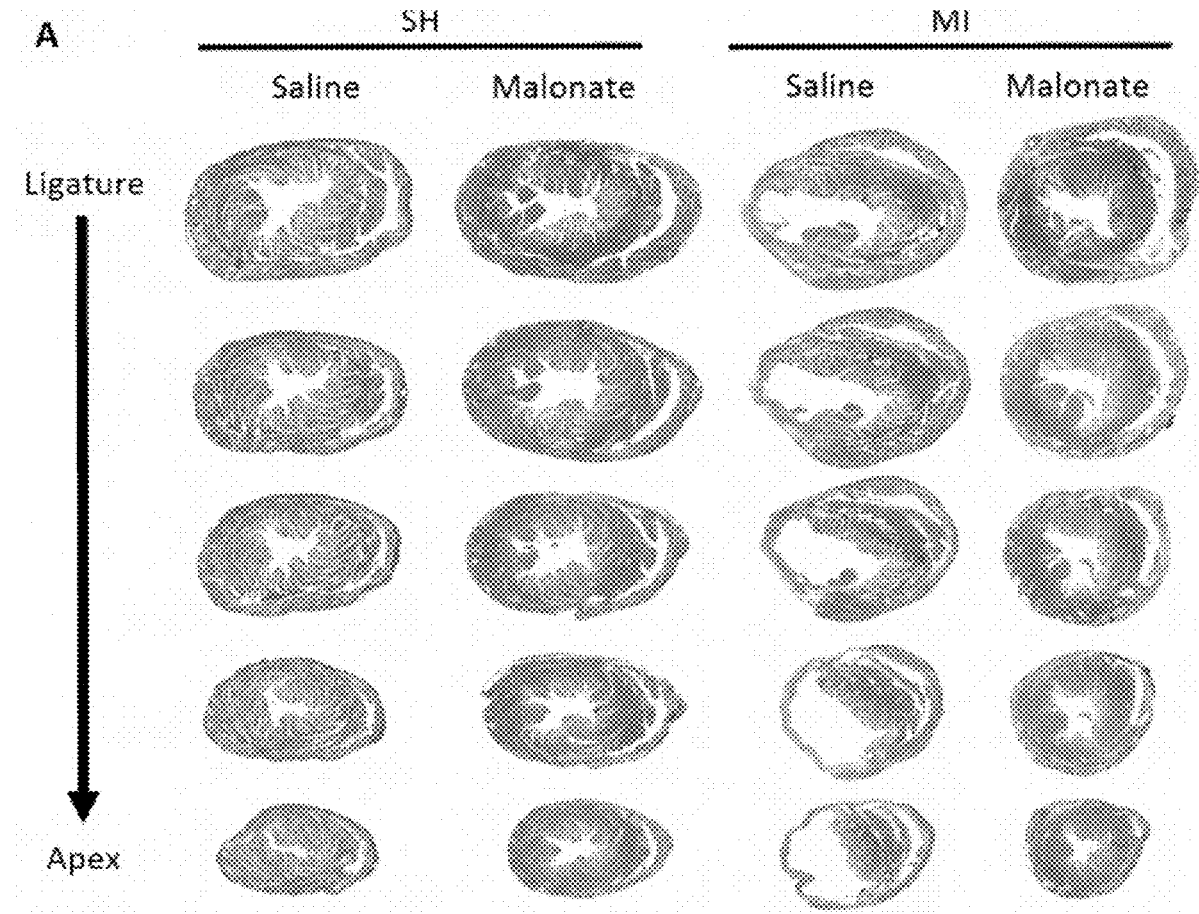
FIGS. 8A-8C. Malonate promotes adult heart regeneration following MI.
Figure 8B:
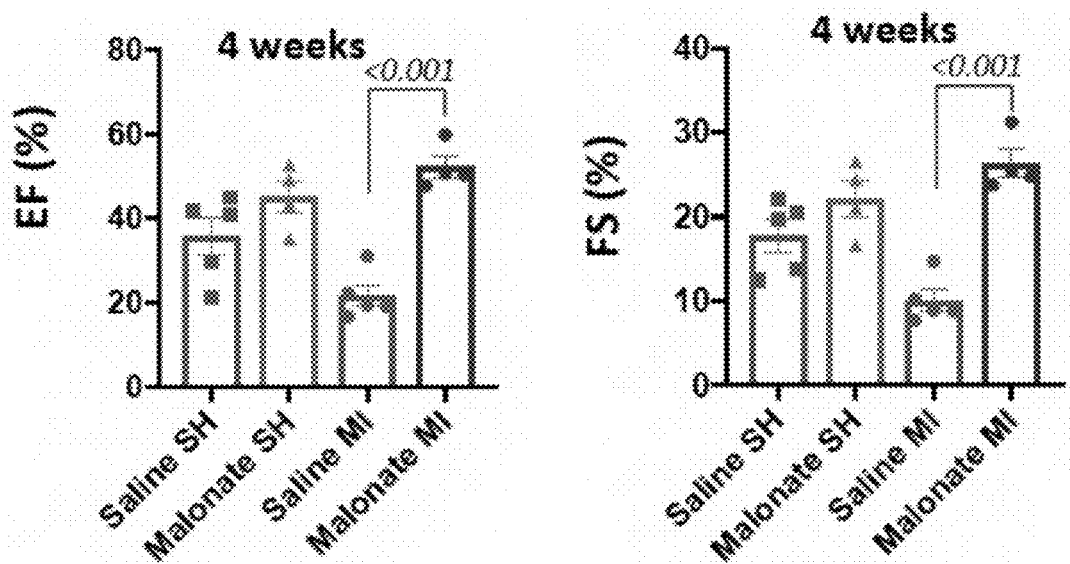
Figure 8C:
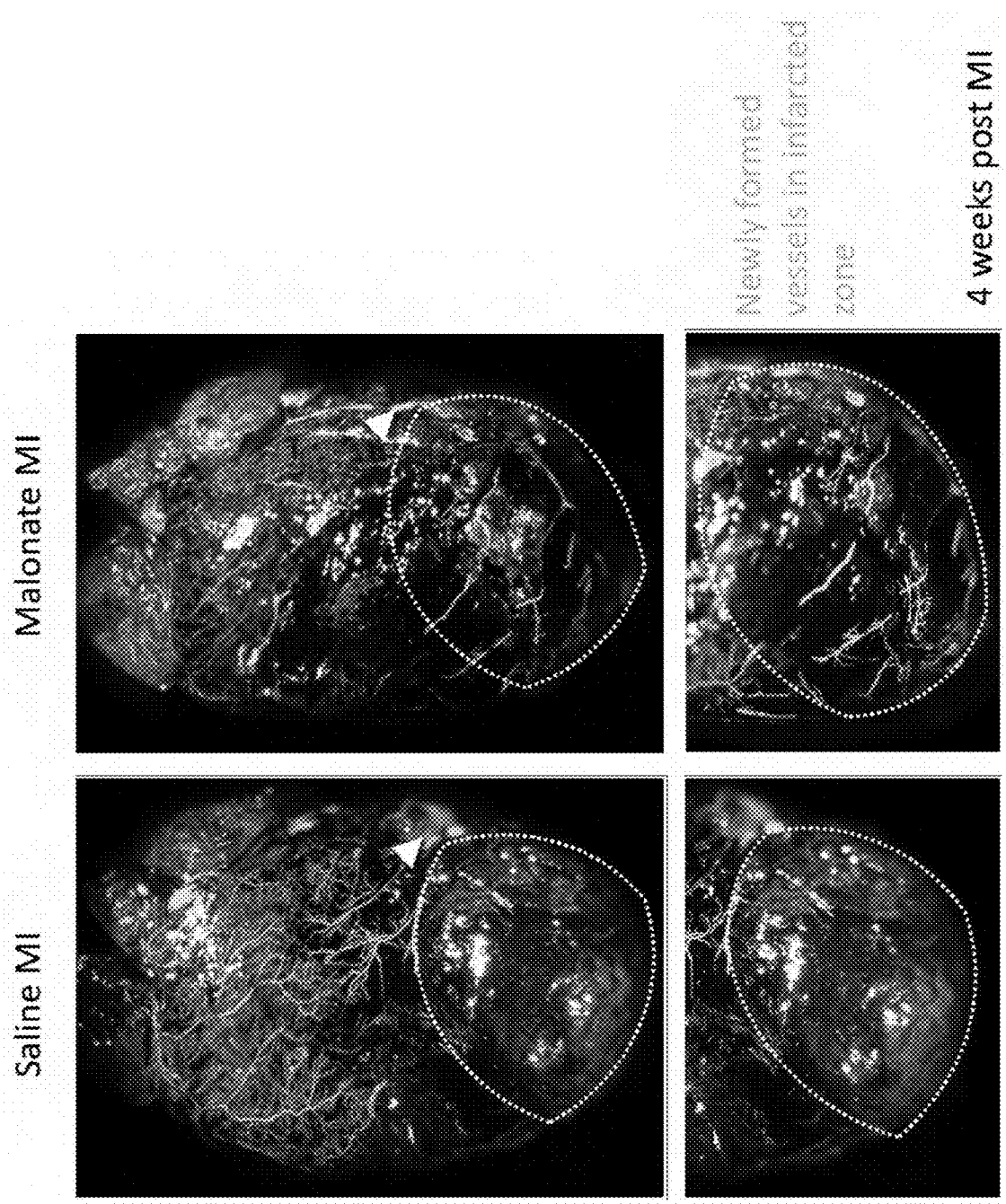

Our results show a robust effect for malonate in promoting cardiomyocyte proliferation and heart regeneration beyond the 1-week postnatal regenerative window in mice. These results are very promising, but it is important to determine whether malonate can promote this regenerative response in the adult mammalian heart. To address this question, we performed MI in 8-10-week-old mice and started injecting saline or dimethyl malonate (100 mg/kg) intraperitoneally post-MI for two weeks. We then collected the hearts of both saline and malonate-injected mice at 28 days post-MI. Interestingly, gross morphology of the malonate-injected hearts showed a more muscularized ventricle compared to controls. To quantify structural regeneration, we performed trichrome staining of both dimethyl malonate and saline-injected hearts. Surprisingly, trichrome staining of paraffin sections below the ligature plane from the dimethyl malonate-injected hearts showed complete restoration of the myocardium with minimal fibrosis compared to the saline-injected controls, the latter of which showed ventricle dilation and significant fibrotic scarring as expected from an adult MI (FIG. 8A). More importantly, echocardiographic measurements showed complete restoration of cardiac function in dimethyl malonate-injected mice compared to the control saline-injected mice as measured by EF and FS (FIG. 8B). Re-vascularization in the infarcted zone was also induced (FIG. 8C). Our surprising results reveal that malonate is capable of restoring cardiac structure and function following adult MI. This cardiac regenerative potential following malonate treatment has enormous implications towards regenerating the adult human heart following injury.

SUMMARY

Cardiomyocyte metabolism plays an essential role in regulating heart function, homeostasis, and regeneration. The current dissection of the cellular and molecular role of cardiomyocyte metabolites in modulating cardiomyocyte proliferation and regeneration has profound implications for enhancing cardiac function in multiple cardiomyopathies.

The experiments provided herein show for the first time the role of malonate in treating adult heart disease and stimulating regeneration.

The experiments provided herein unravel the cellular and molecular role of malonate and succinate during cardiac disease and regeneration.

Example 1 References

1. Writing Group M, Mozaffarian D, Benjamin E J, Go A S, Arnett D K, Blaha M J, Cushman M, Das S R, de Ferranti S, Despres J P, Fullerton H J, Howard V J, Huffman M D, Isasi C R, Jimenez M C, Judd S E, Kissela B M, Lichtman J H, Lisabeth L D, Liu S, Mackey R H, Magid D J, McGuire D K, Mohler E R, 3rd, Moy C S, Muntner P, Mussolino M E, Nasir K, Neumar R W, Nichol G, Palaniappan L, Pandey D K, Reeves M J, Rodriguez C J, Rosamond W, Sorlie P D, Stein J, Towfighi A, Turan T N, Virani S S, Woo D, Yeh R W, Turner M B, American Heart Association Statistics C and Stroke Statistics S. Heart Disease and Stroke Statistics-2016 Update: A Report From the American Heart Association. *Circulation.* 2016; 133: e38-360.
2. Hashimoto H, Olson E N and Bassel-Duby R. Therapeutic approaches for cardiac regeneration and repair. *Nat Rev Cardiol.* 2018; 15:585-600.
3. Dhital K K, Iyer A, Connellan M, Chew H C, Gao L, Doyle A, Hicks M, Kumarasinghe G, Soto C, Dinale A, Cartwright B, Nair P, Granger E, Jansz P, Jabbour A, Kotlyar E, Keogh A, Hayward C, Graham R, Spratt P and Macdonald P. Adult heart transplantation with distant procurement and ex-vivo preservation of donor hearts after circulatory death: a case series. *Lancet.* 2015; 385: 2585-91.
4. Yacoub M. Cardiac donation after circulatory death: a time to reflect. *Lancet.* 2015; 385:2554-6.
5. Becker R O, Chapin S and Sherry R. Regeneration of the ventricular myocardium in amphibians. *Nature.* 1974; 248:145-7.
6. Flink I L. Cell cycle reentry of ventricular and atrial cardiomyocytes and cells within the epicardium following amputation of the ventricular apex in the axolotl, *Amblystoma mexicanum*: confocal microscopic immunofluorescent image analysis of bromodeoxyuridine-labeled nuclei. *Anat Embryol (Berl).* 2002; 205:23544.
7. Oberpriller J O and Oberpriller J C. Response of the adult newt ventricle to injury. *J Exp Zool.* 1974; 187:249-53.
8. Poss K D, Wilson L G and Keating M T. Heart regeneration in zebrafish. *Science.* 2002; 298:2188-2190.
9. Porrello E R, Mahmoud A I, Simpson E, Hill J A, Richardson J A, Olson E N and Sadek H A. Transient regenerative potential of the neonatal mouse heart. *Science.* 2011; 331:1078-80.
10. Porrello E R, Mahmoud A I, Simpson E, Johnson B A, Grinsfelder D, Canseco D, Mammen P P, Rothermel B A, Olson E N and Sadek H A. Regulation of neonatal and adult mammalian heart regeneration by the miR-15 family. *Proceedings of the National Academy of Sciences of the United States of America.* 2013; 110:187-92.
11. Mahmoud A I, Porrello E R, Kimura W, Olson E N and Sadek H A. Surgical models for cardiac regeneration in neonatal mice. *Nature protocols.* 2014; 9:305-11.

12. Webster W S and Abela D. The effect of hypoxia in development. *Birth Defects Res C Embryo Today.* 2007; 81:215-28.
13. Gertz E W, Wisneski J A, Stanley W C and Neese R A. Myocardial substrate utilization during exercise in humans. Dual carbon-labeled carbohydrate isotope experiments. *J Clin Invest.* 1988; 82:2017-25.
14. Lopaschuk G D, Collins-Nakai R L and Itoi T. Developmental changes in energy substrate use by the heart. *Cardiovasc Res.* 1992; 26:1172-80.
15. Puente B N, Kimura W, Muralidhar S A, Moon J, Amatruda J F, Phelps K L, Grinsfelder D, Rothermel B A, Chen R, Garcia J A, Santos C X, Thet S, Mori E, Kinter M T, Rindler P M, Zacchigna S, Mukherjee S, Chen D J, Mahmoud A I, Giacca M, Rabinovitch P S, Aroumougame A, Shah A M, Szweda L I and Sadek H A. The oxygen-rich postnatal environment induces cardiomyocyte cell-cycle arrest through DNA damage response. *Cell.* 2014; 157:565-79.
16. Chouchani E T, Pell V R, Gaude E, Aksentijevic D, Sundier S Y, Robb E L, Logan A, Nadtochiy S M, Ord E N J, Smith A C, Eyassu F, Shirley R, Hu C H, Dare A J, James A M, Rogatti S, Hartley R C, Eaton S, Costa A S H, Brookes P S, Davidson S M, Duchen M R, Saeb-Parsy K, Shattock M J, Robinson A J, Work L M, Frezza C, Krieg T and Murphy M P. Ischaemic accumulation of succinate controls reperfusion injury through mitochondrial ROS. *Nature.* 2014; 515:431-435.
17. Jessup M and Brozena S. Heart failure. *The New England journal of medicine.* 2003; 348:2007-18.
18. Khera R, Pandey A, Ayers C R, Agusala V, Pruitt S L, Halm E A, Drazner M H, Das S R, de Lemos J A and Berry J D. Contemporary Epidemiology of Heart Failure in Fee-For-Service Medicare Beneficiaries Across Healthcare Settings. *Circ Heart Fail.* 2017; 10.
19. Bassat E, Mutlak Y E, Genzelinakh A, Shadrin I Y, Baruch Umansky K, Yifa O, Kain D, Rajchman D, Leach J, Riabov Bassat D, Udi Y, Sarig R, Sagi I, Martin J F, Bursac N, Cohen S and Tzahor E. The extracellular matrix protein agrin promotes heart regeneration in mice. *Nature.* 2017; 547:179-184.
20. Hirose K, Payumo A Y, Cutie S, Hoang A, Zhang H, Guyot R, Lunn D, Bigley R B, Yu H, Wang J, Smith M, Gillett E, Muroy S E, Schmid T, Wilson E, Field K A, Reeder D M, Maden M, Yartsev M M, Wolfgang M J, Grutzner F, Scanlan T S, Szweda L I, Buffenstein R, Hu G, Flamant F, Olgin J E and Huang G N. Evidence for hormonal control of heart regenerative capacity during endothermy acquisition. *Science.* 2019; 364:184-188.
21. Mahmoud A I, Kocabas F, Muralidhar S A, Kimura W, Koura A S, Thet S, Porrello E R and Sadek H A. Meis1 regulates postnatal cardiomyocyte cell cycle arrest. *Nature.* 2013; 497:249-253.
22. Monroe T O, Hill M C, Morikawa Y, Leach J P, Heallen T, Cao S, Krijger P H L, de Laat W, Wehrens X H T, Rodney G G and Martin J F. YAP Partially Reprograms Chromatin Accessibility to Directly Induce Adult Cardiogenesis In Vivo. *Dev Cell.* 2019; 48:765-779 e7.
23. Morikawa Y, Heallen T, Leach J, Xiao Y and Martin J F. Dystrophin-glycoprotein complex sequesters Yap to inhibit cardiomyocyte proliferation. *Nature.* 2017; 547: 227-231.
24. Quaife-Ryan G A, Sim C B, Ziemann M, Kaspi A, Rafehi H, Ramialison M, El-Osta A, Hudson J E and Porrello E R. Multicellular Transcriptional Analysis of Mammalian Heart Regeneration. *Circulation.* 2017; 136: 1123-1139.
25. Das S, Goldstone A B, Wang H, Farry J, D'Amato G, Paulsen M J, Eskandari A, Hironaka C E, Phansalkar R, Sharma B, Rhee S, Shamskhou E A, Agalliu D, de Jesus Perez V, Woo Y J and Red-Horse K. A Unique Collateral Artery Development Program Promotes Neonatal Heart Regeneration. *Cell.* 2019; 176:11281142 e18.
26. Jopling C, Sleep E, Raya M, Marti M, Raya A and Belmonte J C I. Zebrafish heart regeneration occurs by cardiomyocyte dedifferentiation and proliferation. *Nature.* 2010; 464:606-U168.
27. Kikuchi K, Holdway J E, Werdich A A, Anderson R M, Fang Y, Egnaczyk G F, Evans T, MacRae C A, Stainier D Y R and Poss K D. Primary contribution to zebrafish heart regeneration by gata4(+) cardiomyocytes. *Nature.* 2010; 464:601-U162.
28. Mahmoud A I, O'Meara C C, Gemberling M, Zhao L, Bryant D M, Zheng R, Gannon J B, Cai L, Choi W Y, Egnaczyk G F, Burns C E, Burns C G, MacRae C A, Poss K D and Lee R T. Nerves Regulate Cardiomyocyte Proliferation and Heart Regeneration. *Dev Cell.* 2015; 34:387-99.
29. Mahmoud A I and Porrello E R. Turning back the cardiac regenerative clock: lessons from the neonate. *Trends Cardiovasc Med.* 2012; 22:128-33.
30. Ye L, D'Agostino G, Loo S J, Wang C X, Su L P, Tan S H, Tee G Z, Pua C J, Pena E M, Cheng R B, Chen W C, Abdurrachim D, Lalic J, Tan R S, Lee T H, Zhang J and Cook S A. Early Regenerative Capacity in the Porcine Heart. *Circulation.* 2018; 138:2798-2808.
31. Zhu W, Zhang E, Zhao M, Chong Z, Fan C, Tang Y, Hunter J D, Borovjagin A V, Walcott G P, Chen J Y, Qin G and Zhang J. Regenerative Potential of Neonatal Porcine Hearts. *Circulation.* 2018; 138:2809-2816.
32. Wang Z, Ying Z, Bosy-Westphal A, Zhang J, Schautz B, Later W, Heymsfield S B and Muller M J. Specific metabolic rates of major organs and tissues across adulthood: evaluation by mechanistic model of resting energy expenditure. *Am J Clin Nutr.* 2010; 92:1369-77.
33. Fathollahipour S, Patil P S and Leipzig N D. Oxygen Regulation in Development: Lessons from Embryogenesis towards Tissue Engineering. *Cells Tissues Organs.* 2018; 205:350-371.
34. Son G and Han J. Roles of mitochondria in neuronal development. *BMB Rep.* 2018; 51:549-556.
35. Antico Arciuch V G, Elguero M E, Poderoso J J and Carreras M C. Mitochondrial regulation of cell cycle and proliferation. *Antioxid Redox Signal.* 2012; 16:1150-80.
37. Kimura W, Xiao F, Canseco D C, Muralidhar S, Thet S, Zhang H M, Abderrahman Y, Chen R, Garcia J A, Shelton J M, Richardson J A, Ashour A M, Asaithamby A, Liang H, Xing C, Lu Z, Zhang C C and Sadek H A. Hypoxia fate mapping identifies cycling cardiomyocytes in the adult heart. *Nature.* 2015; 523:226-30.
38. Nakada Y, Canseco D C, Thet S, Abdisalaam S, Asaithamby A, Santos C X, Shah A M, Zhang H, Faber J E, Kinter M T, Szweda L I, Xing C, Hu Z, Deberardinis R J, Schiattarella G, Hill J A, Oz O, Lu Z, Zhang C C, Kimura W and Sadek H A. Hypoxia induces heart regeneration in adult mice. *Nature.* 2017; 541:222-227.
39. Honkoop H, de Bakker D E, Aharonov A, Kruse F, Shakked A, Nguyen P D, de Heus C, Garric L, Muraro M J, Shoffner A, Tessadori F, Peterson J C, Noort W, Bertozzi A, Weidinger G, Posthuma G, Grun D, van der Laarse W J, Klumperman J, Jaspers R T, Poss K D, van Oudenaarden A, Tzahor E and Bakkers J. Single-cell analysis uncovers that metabolic reprogramming by ErbB2 signaling is essential for cardiomyocyte proliferation in the regenerating heart. *Elife.* 2019; 8.
40. Chen Q, Vazquez E J, Moghaddas S, Hoppel C L and Lesnefsky E J. Production of reactive oxygen species by mitochondria: central role of complex III. *J Biol Chem.* 2003; 278:36027-31.
41. Scialo F, Fernandez-Ayala D J and Sanz A. Role of Mitochondrial Reverse Electron Transport in ROS Signaling: Potential Roles in Health and Disease. *Front Physiol.* 2017; 8:428.
42. Murphy M P. How mitochondria produce reactive oxygen species. *Biochem J.* 2009; 417:1-13.
43. Hausenloy D J and Yellon D M. Myocardial ischemia-reperfusion injury: a neglected therapeutic target. *J Clin Invest.* 2013; 123:92-100.
44. Pisarenko O, Studneva I, Khlopkov V, Solomatina E and Ruuge E. An assessment of anaerobic metabolism during ischemia and reperfusion in isolated guinea pig heart. *Biochim Biophys Acta.* 1988; 934:5563.
45. Zweier J L, Flaherty J T and Weisfeldt M L. Direct measurement of free radical generation following reperfusion of ischemic myocardium. *Proceedings of the National Academy of Sciences of the United States of America.* 1987; 84:1404-7.
46. Kula-Alwar D, Prag H A and Krieg T. Targeting Succinate Metabolism in Ischemia/Reperfusion Injury. *Circulation.* 2019; 140:1968-1970.
47. Valls-Lacalle L, Barba I, Miro-Casas E, Alburquerque-Bejar J J, Ruiz-Meana M, Fuertes-Agudo M, Rodriguez-Sinovas A and Garcia-Dorado D. Succinate dehydrogenase inhibition with malonate during reperfusion reduces infarct size by preventing mitochondrial permeability transition. *Cardiovasc Res.* 2016; 109:374-84.
48. Valls-Lacalle L, Barba I, Miro-Casas E, Ruiz-Meana M, Rodriguez-Sinovas A and Garcia-Dorado D. Selective Inhibition of Succinate Dehydrogenase in Reperfused Myocardium with Intracoronary Malonate Reduces Infarct Size. *Sci Rep.* 2018; 8:2442.
49. Rodriguez-Cuenca S, Cocheme H M, Logan A, Abakumova I, Prime T A, Rose C, Vidal-Puig A, Smith A C, Rubinsztein D C, Fearnley I M, Jones B A, Pope S, Heales S J, Lam B Y, Neogi S G, McFarlane I, James A M, Smith R A and Murphy M P. Consequences of long-term oral administration of the mitochondria-targeted antioxidant MitoQ to wild-type mice. *Free Radic Biol Med.* 2010; 48:161-72.
50. Smith R A and Murphy M P. Animal and human studies with the mitochondria-targeted antioxidant MitoQ. *Ann N Y Acad Sci.* 2010; 1201:96-103.
51. Gonzalez-Rosa J M, Sharpe M, Field D, Soonpaa M R, Field L J, Burns C E and Burns C G. Myocardial Polyploidization Creates a Barrier to Heart Regeneration in Zebrafish. *Dev Cell.* 2018; 44:433-446 e7.
52. Patterson M, Barske L, Van Handel B, Rau C D, Gan P, Sharma A, Parikh S, Denholtz M, Huang Y, Yamaguchi Y, Shen H, Allayee H, Crump J G, Force T I, Lien C L, Makita T, Lusis A J, Kumar S R and Sucov H M. Frequency of mononuclear diploid cardiomyocytes underlies natural variation in heart regeneration. *Nat Genet.* 2017; 49:1346-1353.
53. Seim G L, Britt E C, John S V, Yeo F J, Johnson A R, Eisenstein R S, Pagliarini D J and Fan J. Two-stage metabolic remodelling in macrophages in response to lipopolysaccharide and interferon-γ stimulation. *Nature Metabolism.* 2019; 1:731-742.
54. Chouchani E T, Methner C, Nadtochiy S M, Logan A, Pell V R, Ding S, James A M, Cocheme H M, Reinhold J, Lilley K S, Partridge L, Fearnley I M, Robinson A J, Hartley R C, Smith R A, Krieg T, Brookes P S and Murphy M P. Cardioprotection by S-nitrosation of a cysteine switch on mitochondrial complex I. *Nat Med.* 2013; 19:753-9.
55. Letouze E, Martinelli C, Loriot C, Burnichon N, Abermil N, Ottolenghi C, Janin M, Menara M, Nguyen A T, Benit P, Buffet A, Marcaillou C, Bertherat J, Amar L, Rustin P, De Reynies A, Gimenez-Roqueplo A P and Favier J. SDH mutations establish a hypermethylator phenotype in paraganglioma. *Cancer Cell.* 2013; 23:73952.
55. Leach J P, Heallen T, Zhang M, Rahmani M, Morikawa Y, Hill M C, Segura A, Willerson J T and Martin J F. Hippo pathway deficiency reverses systolic heart failure after infarction. *Nature.* 2017; 550:260-264.
56. Mills E L, Kelly B, Logan A, Costa A S H, Varma M, Bryant C E, Tourlomousis P, Dabritz J H M, Gottlieb E, Latorre I, Corr S C, McManus G, Ryan D, Jacobs H T, Szibor M, Xavier R J, Braun T, Frezza C, Murphy M P and O'Neill L A. Succinate Dehydrogenase Supports Metabolic Repurposing of Mitochondria to Drive Inflammatory Macrophages. *Cell.* 2016; 167:457-470 e13.
57. Aurora A B, Porrello E R, Tan W, Mahmoud A I, Hill J A, Bassel-Duby R, Sadek H A and Olson E N. Macrophages are required for neonatal heart regeneration. *J Clin Invest.* 2014; 124:1382-92.
58. Bajpai G, Bredemeyer A, Li W, Zaitsev K, Koenig A L, Lokshina I, Mohan J, Ivey B, Hsiao H M, Weinheimer C, Kovacs A, Epelman S, Artyomov M, Kreisel D and Lavine K J. Tissue Resident CCR2− and CCR2+Cardiac Macrophages Differentially Orchestrate Monocyte Recruitment and Fate Specification Following Myocardial Injury. *Circ Res.* 2019; 124:263-278.
59. Lavine K J, Epelman S, Uchida K, Weber K J, Nichols C G, Schilling J D, Ornitz D M, Randolph G J and Mann D L. Distinct macrophage lineages contribute to disparate patterns of cardiac recovery and remodeling in the neonatal and adult heart. *Proceedings of the National Academy of Sciences of the United States of America.* 2014; 111:16029-34.
60. Vagnozzi R J, Maillet M, Sargent M A, Khalil H, Johansen A K Z, Schwanekamp J A, York A J, Huang V, Nahrendorf M, Sadayappan S and Molkentin J D. An acute immune response underlies the benefit of cardiac stem cell therapy. *Nature.* 2020; 577:405-409.
61. Yu J, Hu K, Smuga-Otto K, Tian S, Stewart R, Slukvin, I I and Thomson J A. Human induced pluripotent stem cells free of vector and transgene sequences. *Science.* 2009; 324:797-801.
62. Lian X, Hsiao C, Wilson G, Zhu K, Hazeltine L B, Azarin S M, Raval K K, Zhang J, Kamp T J and Palecek S P. Robust cardiomyocyte differentiation from human pluripotent stem cells via temporal modulation of canonical Wnt signaling. *Proceedings of the National Academy of Sciences of the United States of America.* 2012; 109: E1848-57.
63. Lian X, Zhang J, Azarin S M, Zhu K, Hazeltine L B, Bao X, Hsiao C, Kamp T J and Palecek S P. Directed cardiomyocyte differentiation from human pluripotent stem cells by modulating Wnt/beta-catenin signaling under fully defined conditions. *Nature protocols.* 2013; 8:162-75.
64. Lian X, Bao X, Zilberter M, Westman M, Fisahn A, Hsiao C, Hazeltine L B, Dunn K K, Kamp T J and Palecek S P. Chemically defined, albumin-free human cardiomyocyte generation. *Nat Methods.* 2015; 12:595-6.

65. Cai W, Zhang J, de Lange W J, Gregorich Z R, Karp H, Farrell E T, Mitchell S D, Tucholski T, Lin Z, Biermann M, McIlwain S J, Ralphe J C, Kamp T J and Ge Y. An Unbiased Proteomics Method to Assess the Maturation of Human Pluripotent Stem Cell-Derived Cardiomyocytes. *Circ Res.* 2019; 125:936-953.
66. Dikalov S I and Harrison D G. Methods for detection of mitochondrial and cellular reactive oxygen species. *Antioxid Redox Signal.* 2014; 20:372-82.
67. Hu D, Linders A, Yamak A, Correia C, Kijlstra J D, Garakani A, Xiao L, Milan D J, van der Meer P, Serra M, Alves P M and Domian I J. Metabolic Maturation of Human Pluripotent Stem Cell-Derived Cardiomyocytes by Inhibition of HIF1alpha and LDHA. *Circ Res.* 2018; 123:1066-1079.
68. Parikh S S, Blackwell D J, Gomez-Hurtado N, Frisk M, Wang L, Kim K, Dahl C P, Fiane A, Tonnessen T, Kryshtal D O, Louch W E and Knollmann B C. Thyroid and Glucocorticoid Hormones Promote Functional T-Tubule Development in Human-Induced Pluripotent Stem Cell-Derived Cardiomyocytes. *Circ Res.* 2017; 121:1323-1330.

Example 2

Summary

Neonatal mouse cardiomyocytes undergo a metabolic switch from glycolysis to oxidative phosphorylation, which results in a significant increase in reactive oxygen species (ROS) production that induces DNA damage. These cellular changes contribute to cardiomyocyte cell cycle exit and loss of the capacity for cardiac regeneration. The mechanisms that regulate this metabolic switch and the increase in ROS production have been relatively unexplored. Current evidence suggests that elevated ROS production in ischemic tissues occurs due to accumulation of the mitochondrial metabolite succinate during ischemia via succinate dehydrogenase (SDH), and this succinate is rapidly oxidized at reperfusion. Interestingly, mutations in SDH in familial cancer syndromes have been demonstrated to promote a metabolic shift into glycolytic metabolism, suggesting a potential role for SDH in regulating cellular metabolism. Whether succinate and SDH regulate cardiomyocyte cell cycle activity and the cardiac metabolic state has remained unclear.

In the present example, we show the role of succinate and succinate dehydrogenase (SDH) inhibition in regulating postnatal cardiomyocyte cell cycle activity and heart regeneration.

Our results demonstrate that injection of succinate in neonatal mice results in inhibition of cardiomyocyte proliferation and regeneration. Our evidence also shows that inhibition of SDH through treatment with SDH inhibitors such as malonate and Atpenin A5 after birth extends the window of cardiomyocyte proliferation and regeneration in juvenile mice. Remarkably, extending SDH inhibitor treatment to the adult mouse heart following myocardial infarction injury results in a robust regenerative response within 4 weeks following injury by promoting adult cardiomyocyte proliferation and revascularization. Our metabolite analysis following SDH inhibition indicates a dynamic switch of adult cardiac metabolism from oxidative phosphorylation to glycolysis.

Inhibition of SDH with malonate or other SDH inhibitors promotes adult cardiomyocyte proliferation, revascularization, and heart regeneration via metabolic reprogramming. These findings support an important new therapeutic approach for human heart failure.

We show that competitive inhibitors of succinate dehydrogenase (SDH) promote adult cardiomyocyte proliferation, revascularization of the infarct zone, and myocardial regeneration following infarction. We also found that SDH inhibition induces a metabolic shift from oxidative phosphorylation to glucose metabolism in the adult heart.

Transient inhibition of SDH represents an important metabolic target to promote adult heart regeneration following infarction.

Introduction

Cardiovascular disease remains the leading cause of death in the world[1]. Both vascular and myocardial damage arise from acute cardiovascular events such as myocardial infarction (MI). The limited capacity of the adult heart to repair itself represents a major barrier in cardiovascular medicine and often leads to heart failure. In contrast, the neonatal mouse heart has the ability to regenerate following MI, with the newly formed cardiac tissue being derived primarily from the proliferation of the pre-existing cardiomyocytes[2-4]. During postnatal development, exposure to high levels of atmospheric oxygen following birth results in a metabolic switch in energy utilization from glycolysis to oxidative phosphorylation[5]. This metabolic switch results in increased mitochondrial reactive oxygen species (ROS) production, causing cardiomyocyte DNA damage and contributing to the postnatal cardiomyocyte cell cycle arrest in mice[6]. Thus, understanding the metabolic state of the mammalian heart following birth can lead to important insights towards restoring adult cardiomyocyte cell cycle activity and subsequent regenerative abilities following injury.

Recent studies have demonstrated that the metabolite succinate accumulates during ischemia, which is a conserved phenomenon across vertebrates[7-9]. Different models suggest that succinate accumulation occurs either through reverse activity of the enzyme complex succinate dehydrogenase (SDH, also known as complex II), or via canonical tricarboxylic acid (TCA) cycle[7,9]. SDH activity plays a central role in succinate accumulation in the proposed models owing to its involvement in both the TCA cycle and the electron transport chain (ETC)[10]. Subsequently upon reperfusion, the high levels of accumulated succinate are rapidly metabolized into fumarate, which results in a burst of ROS production via reverse activity of mitochondrial complex I[7,11]. More importantly, administration of the SDH competitive inhibitor, malonate, prevents the accumulation of succinate and the subsequent metabolization that increases ROS levels during ischemia/reperfusion injury, emphasizing the link between SDH and ROS production[7,11,12].

SDH plays an important role in metabolism and cell cycle activity, as it is the first mitochondrial protein to be identified as a tumor suppressor[13]. Mutations in SDH in familial cancer syndromes promote a metabolic shift into glycolysis that drives cell division[13-15]. Interestingly, metabolic reprogramming to glycolysis is essential during zebrafish heart regeneration, which is concomitant with a significant reduction in SDH activity as well[16]. However, whether succinate and SDH activity directly contribute to the limited regenerative capability of the heart after injury is unknown. In this study, we aim to determine the role of succinate and SDH in regulation of postnatal cardiomyocyte cell cycle activity and heart regeneration.

Methods

Animals

CD-1 mice were obtained from Charles River Laboratories. All animal experimental procedures were approved by the Institutional Animal Care and Use Committee of the University of Wisconsin-Madison. All experiments were performed on age and sex matched mice, with an equal ratio of male to female mice for neonatal experiments and only male mice for adult experiments.

Neonatal Myocardial Infarction

Neonatal mice at postnatal day 1 (P1) or day 7 (P7) were used for myocardial infarction (MI) surgery. Neonatal mice were subjected to MI surgeries as previously described. Briefly, neonates were anesthetized by hypothermia on ice. Lateral thoracotomy at the fourth intercostal space was performed by blunt dissection of the intercostal muscles after skin incision. A C-1 tapered needle attached to a 6-0 prolene suture (Ethicon Inc., Bridgewater, N.J.) was passed through the mid-ventricle below the left anterior descending coronary artery (LAD) and tied off to induce MI. The prolene suture was used to suture the ribs together and seal the chest wall incisions, and the skin was closed using adhesive glue (3M). The mice then were warmed on a heating pad until recovery. Sham-operated mice underwent the same procedure including hypothermic anesthesia, but not LAD ligation.

Adult Myocardial Infarction

Adult male mice (8-week-old) were subjected to MI by ligation of the proximal aspect of the LAD coronary artery. In brief, mice were anaesthetized using 3% isoflurane, then mice were intubated with PE50 tubing and placed on a mouse ventilator at 120-130 breaths per minute with a stroke volume of 150 microliters and maintained on 2% isoflurane. A left lateral incision through the fourth intercostal space was made to expose the heart. After visualizing the left coronary artery, 7-0 suture was placed through the myocardium in the anterolateral wall and secured as previously describer[17,18]. Coronary artery entrapment was confirmed by observing blanching of the distal circulation (ventricular apex). ECG was used to confirm MI by noting ST segment changes. The lungs were over inflated, and the ribs and muscle layers were closed by absorbable sutures. The skin is closed by additional suturing using 6-0 nylon. The mouse was recovered from the anesthesia and extubated.

Drug Administration

Neonatal mice were weighed and injected daily with either saline, 100 mg/kg dimethyl succinate (Sigma), 100 mg/kg dimethyl malonate (Sigma), or 100 µg/kg Atpenin A5 (Enzo Life Sciences). Dimethyl succinate and dimethyl malonate were dissolved in saline. Stock solution of Atpenin A5 at 0.1 mg/ml was initially prepared by dissolving in DMSO (Sigma) and then further diluted with saline before injection. Saline was used as a vehicle control for all experiments. Neonatal mice were given intravenous injections for the first 5 days after birth, followed by intraperitoneal injections until completion of the injection time course. Adult mice were injected intraperitoneally daily with either saline or 100 mg/kg dimethyl malonate post-MI for 2 or 4 weeks. To track cardiomyocyte proliferation, we added 0.25 mg/ml 5-bromodeoxyuridine (BrdU, Sigma) to the drinking water for 2 weeks post-MI. Fresh BrdU-containing water was changed every 2 days.

Histology

Hearts were harvested and fixed in 4% paraformaldehyde (PFA) in PBS solution overnight at 4° C., processed for paraffin embedding, and sectioned at intervals. Masson's trichrome staining was performed according to the manufacture's protocol (Newcomer Supply, Middleton, WI). Scar size measurements were quantified from at least 3 sections of the heart from ligature to apex. ImageJ was used to quantify the fibrotic scar, and the average scar area for each heart was plotted.

Metabolite Analysis

To analyze intracellular metabolites, metabolites were extracted with cold liquid chromatography-mass spectrometry (LC-MS) grade 3/1 butanol/methanol (v/v). The methanol layer was transferred to a new vial and samples were dried under nitrogen flow and subsequently dissolved in LC-MS grade water for LC-MS analysis methods. Protein pellets were removed by centrifugation. Samples were analyzed using a Thermo Q-Exactive mass spectrometer coupled to a Vanquish Horizon Ultra-High Performance Liquid Chromatograph (UHPLC). Metabolites were separated on a C18 (details below) at a 0.2 ml per min flow rate and 30° C. column temperature. Data was collected on full scan mode at a resolution of 70 K. Samples were loaded in water and separated on a 2.1×100 mm, 1.7 µM Acquity UPLC BEH C18 Column (Waters) with a gradient of solvent A (97/3 H2O/methanol, 10 mM TBA, 9 mM acetate, pH 8.2) and solvent B (100% methanol). The gradient was: 0 min, 5% B; 2.5 min, 5% B; 17 min, 95% B; 21 min, 95% B; 21.5 min, 5% B. Data were collected on a full scan negative mode. Settings for the ion source were: 10 aux gas flow rate, 35 sheath gas flow rate, 2 sweep gas flow rate, 3.2 kV spray voltage, 320° C. capillary temperature and 300° C. heater temperature. The identification of metabolites reported was based on exact m/z and retention times, which were determined with chemical standards. Data were analyzed with Maven. Relative metabolite levels were normalized to internal standard Tryptophan ($^{13}C11$) and expressed relative to levels measured in the control group.

Echocardiography

Transthoracic echocardiography was performed by using a Visual Sonics 770 ultrasonograph with a 25-MHz transducer (Visual Sonics, Toronto) as described previously[19]. Mice were lightly anesthetized with 1% isoflurane and maintained on a heated platform. Two-dimensionally guided M-mode images from a parasternal long axis (PLAX) of the left ventricle (LV) were acquired at the tip of the papillary muscles. Wall thickness and chamber diameters were measured in both diastole and systole. Fractional shortening was calculated as (LVDd−LVDs)/LVDd×100, where LVDd is LV diameter in diastole and LVDs is LV diameter in systole. Ejection fraction was calculated as $[(7.0/(2.4+LVDd)(LVDd)^3 - (7.0/(2.4+LVDs)(LVDs)^3/(7.0/(2.4+LVDd)(LVDd)^3] \times 100$ and LV mass was calculated by using the formula $[1.05 \times ((Posterior Wall_{diastole} + Anterior Wall_{diastole} + LVDd)^3 - (LVDd)^3)]$. All parameters were measured over at least three consecutive cycles.

Statistical Analysis

All graphs are presented as means±SE. Statistical analysis was performed using Prism 9 (GraphPad Software). Two-tailed Student's t-test was performed to determine the difference between the treatment group and control group. One-way ANOVA was performed by Tukey's multiple comparison test to determine the differences of group mean among treatment groups. The level of significance was set at $P<0.05$.

Results

Figure 9A:
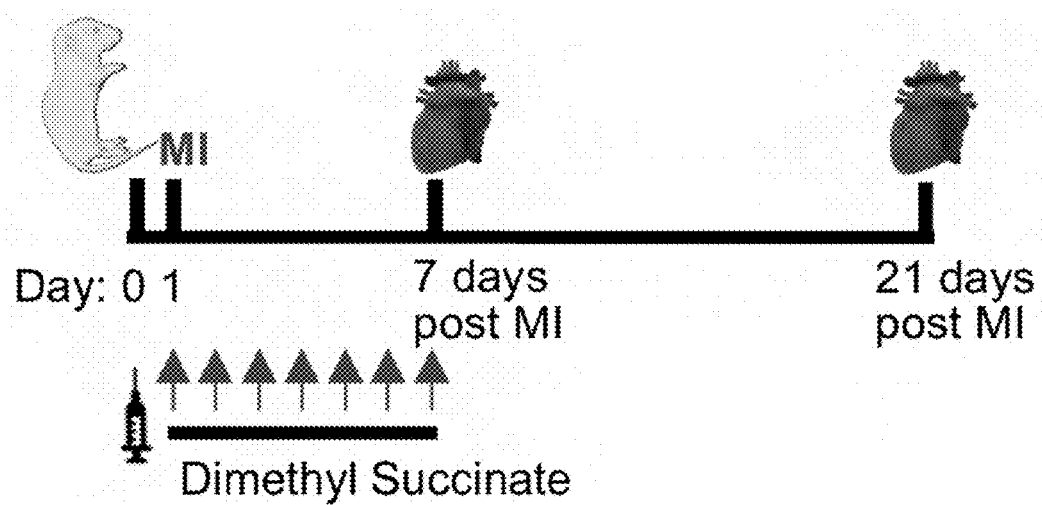
FIGS. 9A-9G. Succinate reduces cardiomyocyte proliferation and blocks heart regeneration in neonatal mice following myocardial infarction (MI).
Figure 9F:
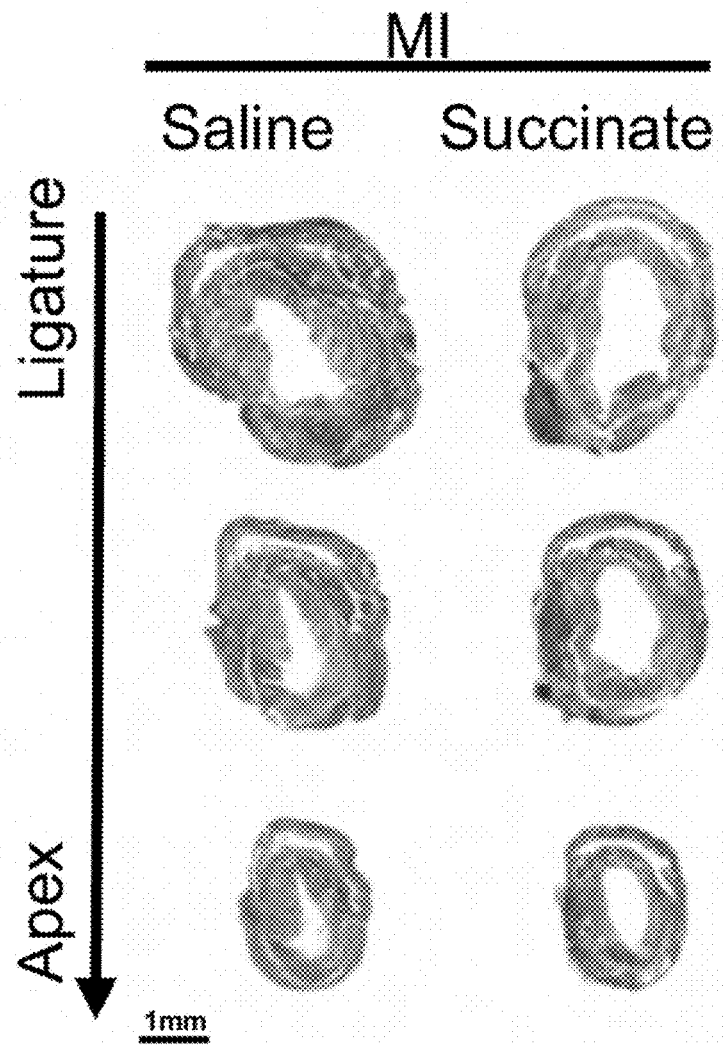
Figure 9B:
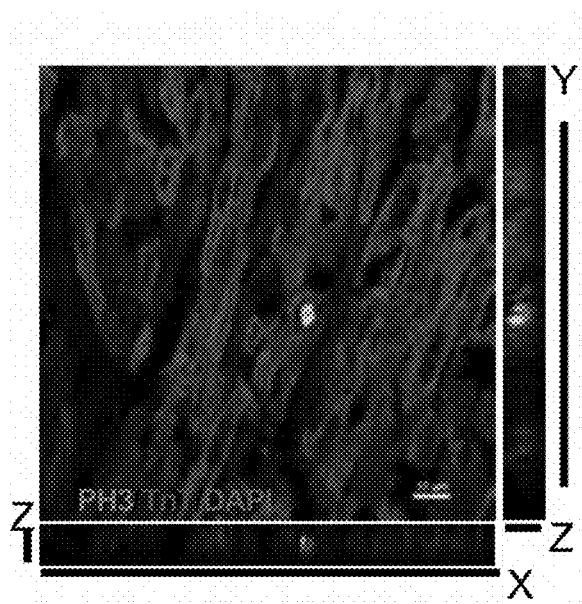
Figure 9C:
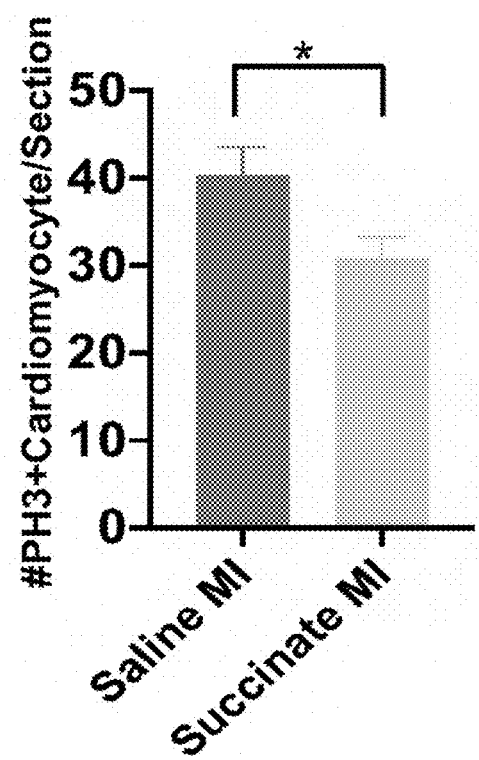
Figure 9D:
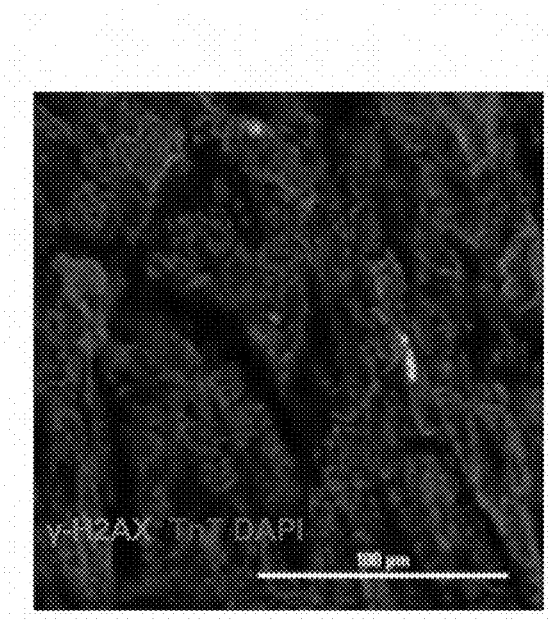
Figure 9E:
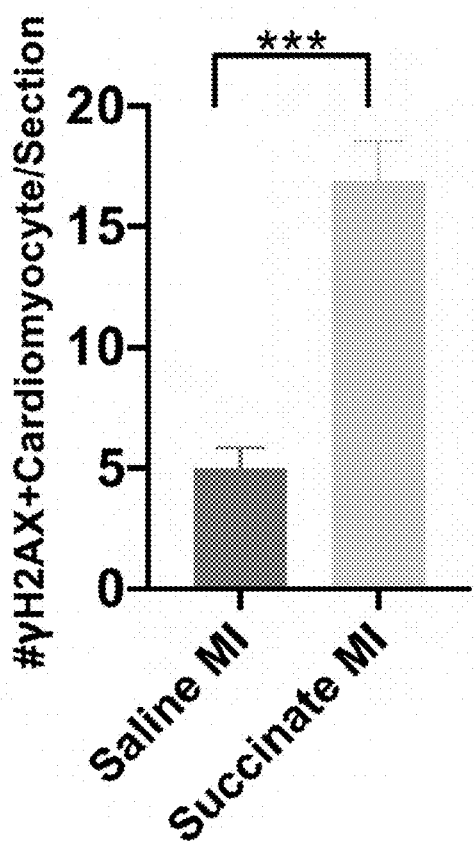
Figure 9G:
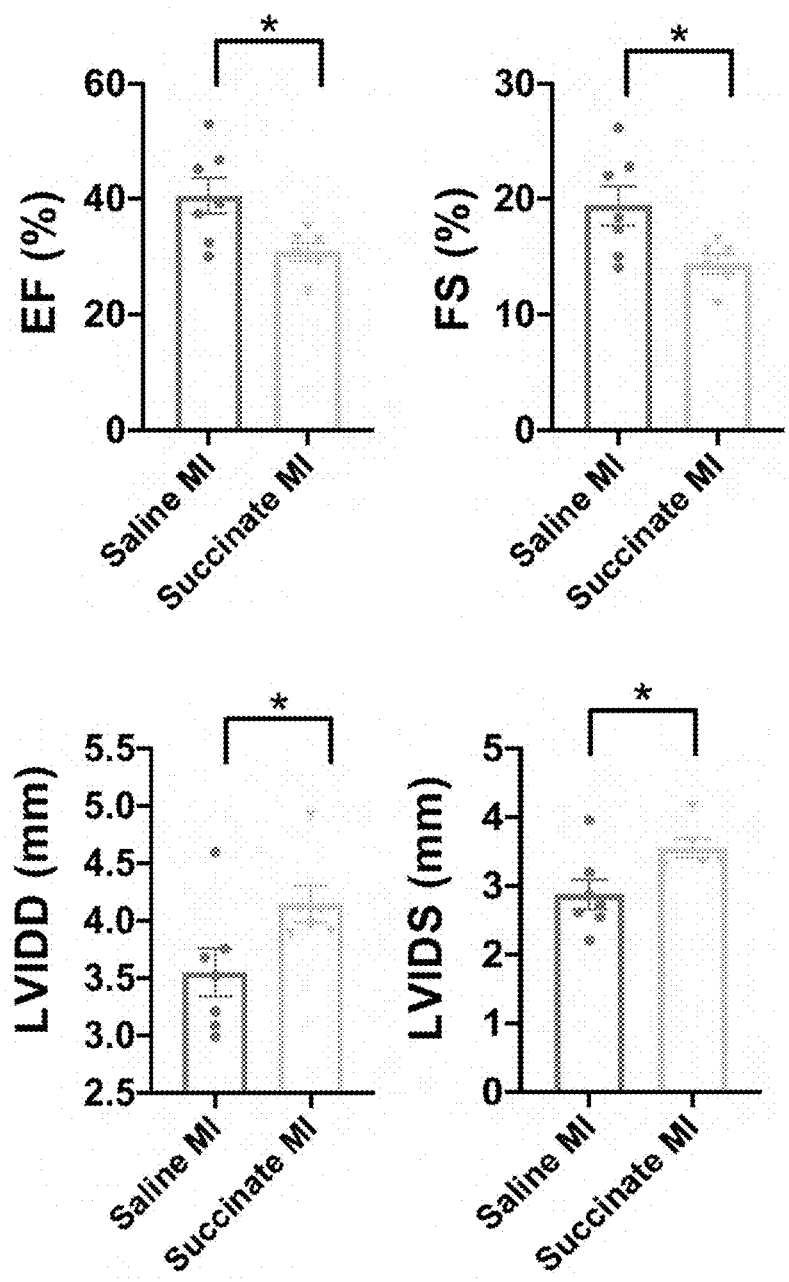

Succinate Reduces Cardiomyocyte Proliferation and Heart Regeneration in Neonatal Mice To determine whether an increase in succinate levels impacts cardiomyocyte cell cycle activity and neonatal mouse heart regeneration, neonatal mice were injected with dimethyl succinate (100 mg/kg) daily for 7 days following myocardial infarction at postnatal day1 (P1) (FIG. 9A). We tested multiple doses (50, 100, 150 mg/kg) and we found that 100 mg/kg was the minimum effective dose that reduces cardiomyocyte proliferation (data not shown). To determine whether succinate reduces cardiomyocyte proliferation, we performed immunostaining of the mitosis marker pH3 at 7 days post-MI. Our results revealed a reduction in cardiomyocyte mitosis in succinate-injected MI hearts compared to controls (FIGS. 9B and 9C).

showed lack of regeneration with persistence of a fibrotic scar (FIG. 9F). This lack of regeneration was also evident in the significant reduction in cardiac function of dimethyl succinate-injected mice compared to saline-injected controls, as measured by ejection fraction (EF), fractional shortening (FS), left ventricle internal diameter diastole (LVIDD), and left ventricle internal diameter systole (LVIDS) (FIG. 9G and Table 1). Together, these results reveal that succinate injection during the first week of life can result in premature cardiomyocyte cell cycle exit, which inhibits the neonatal cardiac regenerative response.

TABLE 1

The fundamental measured and calculated echocardiography parameters of saline- and succinate-injected hearts (P1D21).

|  | Saline | | Succinate | |
| --- | --- | --- | --- | --- |
|  | SH (n = 7) | MI (n = 7) | SH (n = 7) | MI (n = 6) |
| Measurement |  |  |  |  |
| LVIDD (mm) | 3.144 ± 0.145 | 3.550 ± 0.207 | 3.347 ± 0.067 | 4.148 ± 0.159 |
| LVPWD (mm) | 0.670 ± 0.022 | 0.619 ± 0.016 | 0.643 ± 0.017 | 0.600 ± 0.030 |
| LVIDS (mm) | 2.246 ± 0.122 | 2.876 ± 0.214 | 2.470 ± 0.084 | 3.552 ± 0.131 |
| LVPWS (mm) | 0.799 ± 0.017 | 0.749 ± 0.015 | 0.774 ± 0.013 | 0.718 ± 0.043 |
| LVAWD (mm) | 0.666 ± 0.017 | 0.621 ± 0.015 | 0.634 ± 0.016 | 0.583 ± 0.030 |
| LVAWS (mm) | 0.791 ± 0.013 | 0.750 ± 0.017 | 0.784 ± 0.014 | 0.717 ± 0.046 |
| Calculation |  |  |  |  |
| LV Vol; d (μL) | 40.124 ± 4.525 | 54.424 ± 8.083 | 45.859 ± 2.235 | 77.264 ± 7.538 |
| LV Vol; s (μL) | 17.604 ± 2.466 | 33.293 ± 6.481 | 21.983 ± 1.904 | 53.328 ± 4.968 |
| % EF | 56.596 ± 1.682 | 40.594 ± 3.090 | 52.308 ± 2.319 | 30.832 ± 1.597 |
| % FS | 28.697 ± 1.025 | 19.413 ± 1.671 | 26.161 ± 1.387 | 14.355 ± 0.826 |
| LV Mass (mg) | 62.313 ± 4.196 | 70.120 ± 8.004 | 64.802 ± 2.640 | 85.704 ± 9.647 |
| HR (BPM) | 353.571 ± 10.417 | 309.429 ± 16.579 | 415.000 ± 21.077 | 390.800 ± 32.818 |

Notes.
SH = Sham.
MI = Myocardial Infarction.
LVIDD = Left Ventricle Internal Diameter Diastole.
LVPWD = Left Ventricle Posterior Wall Thickness Diastole.
LVIDS = Left Ventricle Internal Diameter Systole.
LVPWS = Left Ventricle Posterior Wall Thickness Systole.
LVAWD = Left Ventricle Anterior Wall Thickness Diastole.
LVAWS = Left Ventricle Anterior Wall Thickness Systole.
LV Vol; d = Left Ventricular Volume; diastole.
LV Vol; s = Left Ventricular Volume; systole.
% EF = Ejection Fraction.
% FS = Fractional Shortening.
LV Mass = Left Ventricular Mass (Anatomical Weight).
HR = Heart Rate.
Data are expressed as mean ± SE.

Loss of cardiomyocyte cell cycle activity occurs due to increase in cardiomyocyte DNA damage as a consequence of the metabolic switch to oxidative phosphorylation and the subsequent rise in ROS levels. To determine whether succinate induces cardiomyocyte DNA damage, we performed immunostaining of γH2AX, which is a marker for DNA double-strand breaks. We quantified a significant increase in cardiomyocytes with γH2AX foci in succinate-treated mice (FIGS. 9D and 9E). Our results demonstrate that in neonatal mice high levels of succinate can induce cardiomyocyte DNA damage and reduce the proliferative potential of pre-existing cardiomyocytes, which is the main source of the newly formed cardiomyocytes during cardiac regeneration[3,20].

Figure 10D:
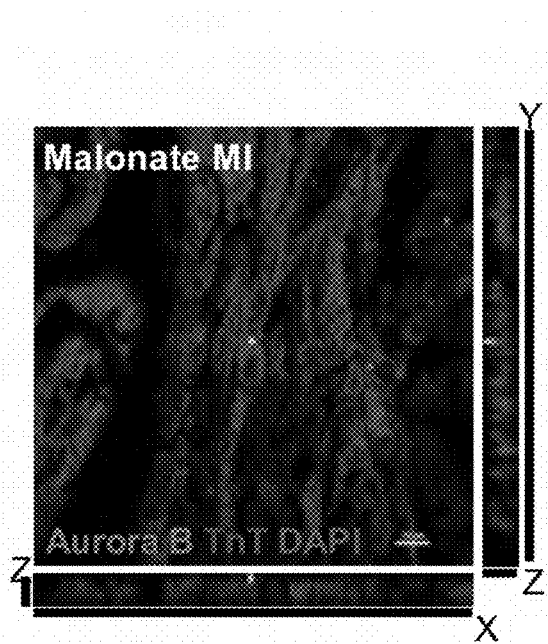
Figure 10E:
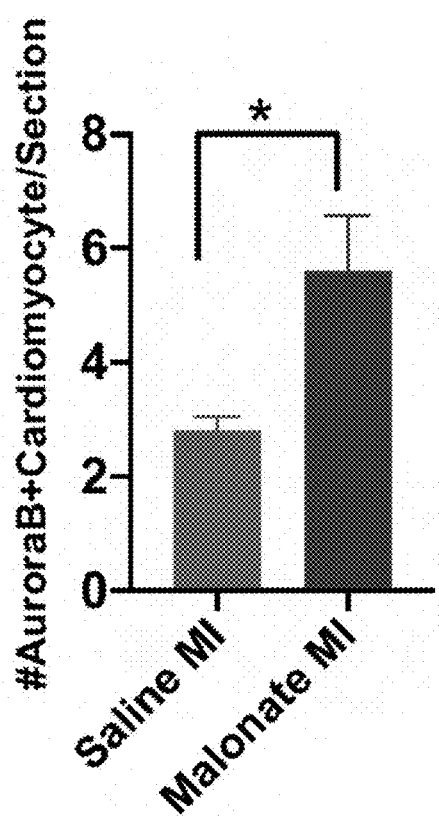
Figure 10F:
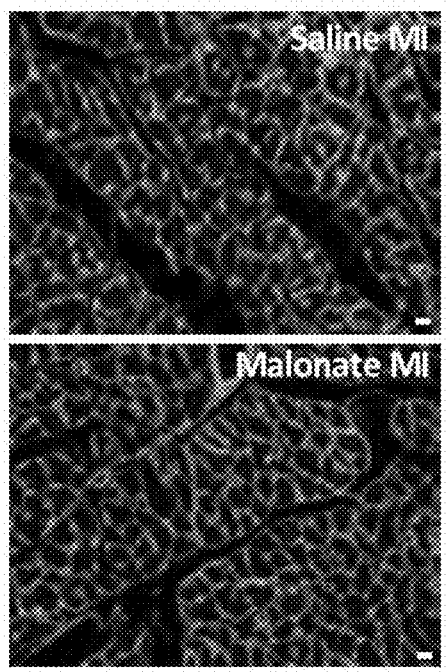
Figure 10G:
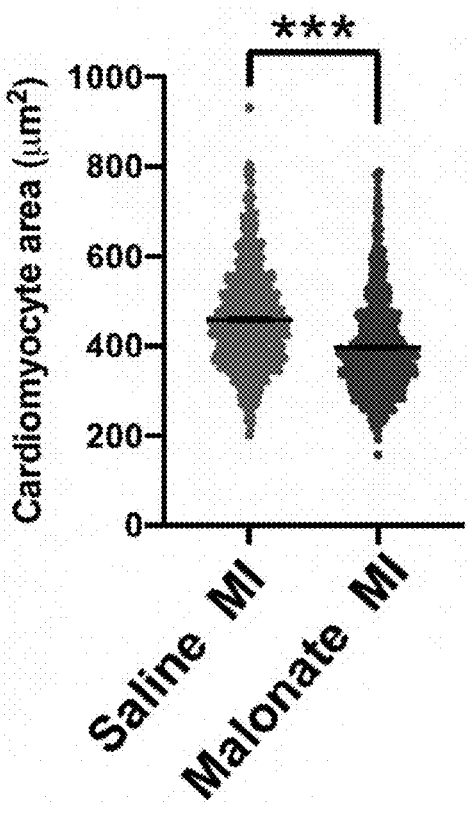
Figure 10H:
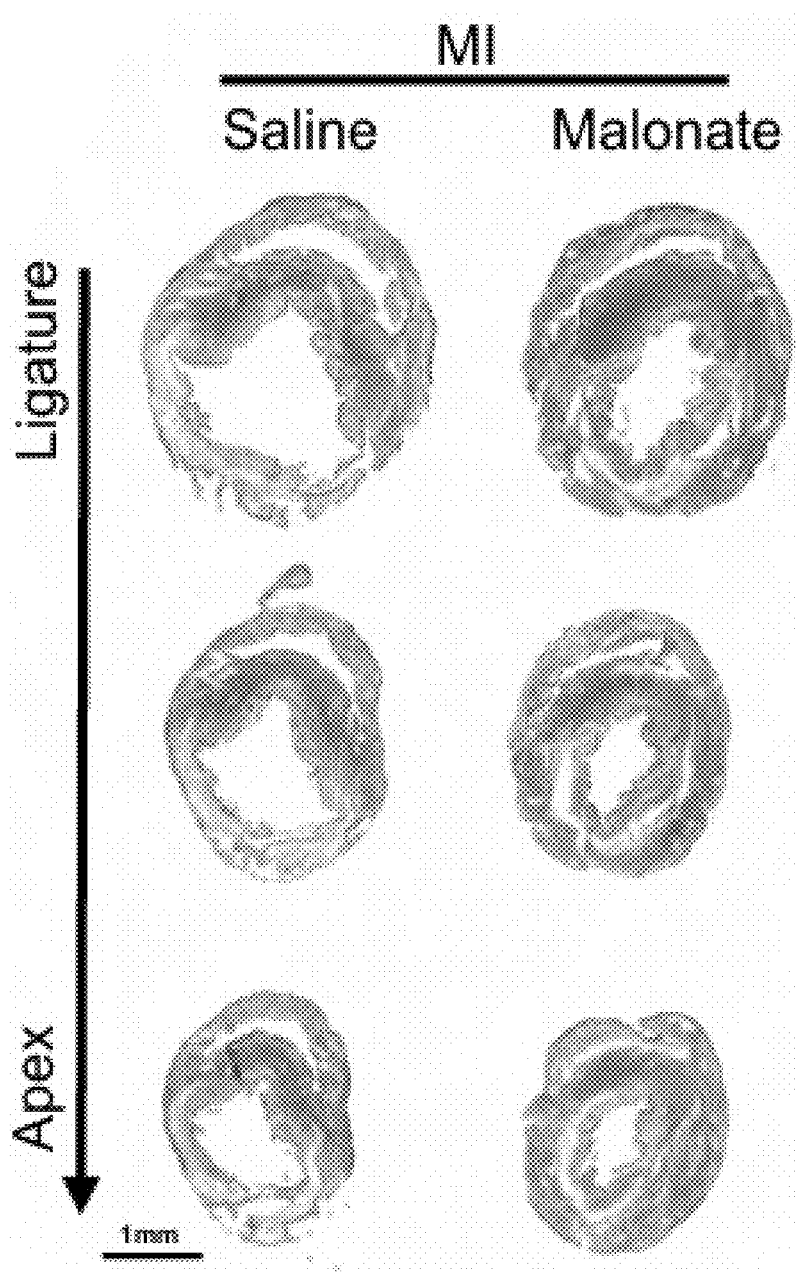
Figure 10I:
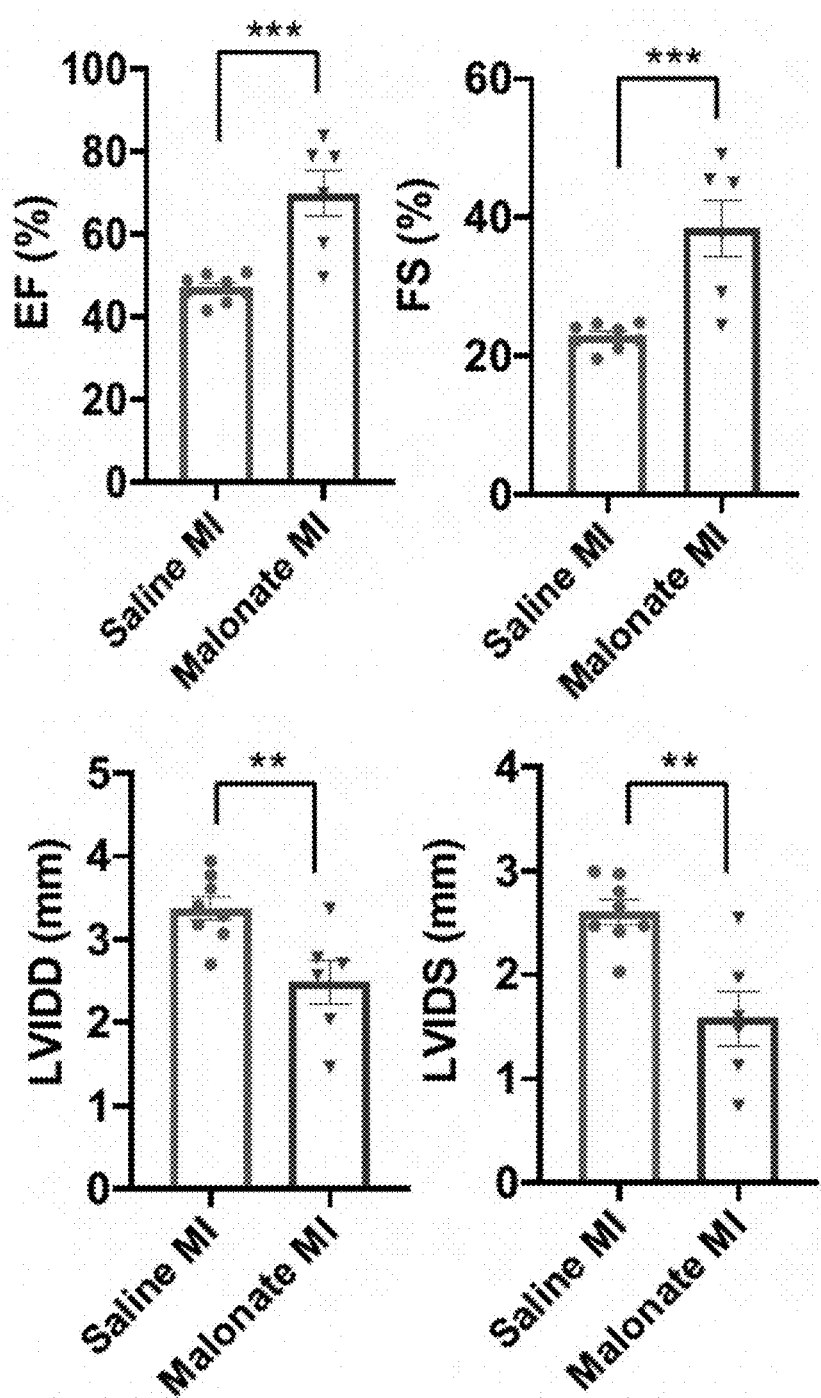
Figure 11:
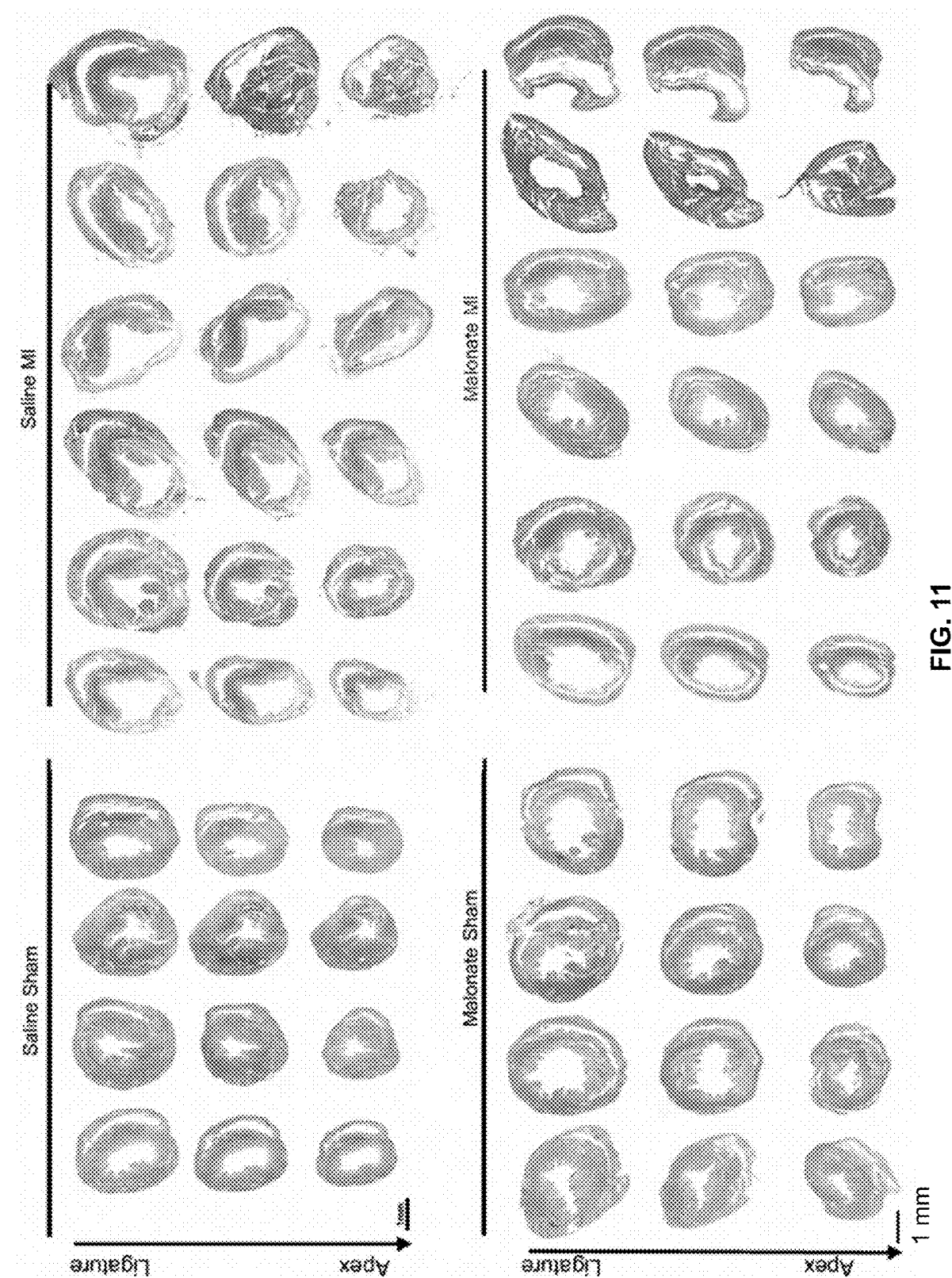
FIG. 11. Masson's trichrome-stained heart sections of saline or malonate-injected mice at 21 days post sham or MI surgery performed at P7. Serial sections were cut from the site of the ligature to the apex. All hearts are shown.

To further establish the effects of succinate on neonatal heart regeneration, we performed trichrome staining at 21 days post-MI to assess regeneration and fibrosis in control and dimethyl succinate-injected mice. As expected, saline-injected control mice demonstrated complete heart regeneration. In contrast, dimethyl succinate-injected mice Malonate Extends the Cardiac Regenerative Window in Postnatal Hearts Although our results demonstrate that exogenous administration of succinate can inhibit cardiomyocyte proliferation and regeneration, it remains unclear whether succinate dehydrogenase (SDH) activity contributes to cardiomyocyte cell cycle exit in the postnatal heart. Thus, we wanted to determine whether the SDH complex competitive inhibitor, malonate, could extend the cardiomyocyte proliferative window and improve the cardiac regeneration capacity of the juvenile, normally non-regenerative 7-day-old mice. We injected dimethyl malonate (100 mg/kg, daily) in neonatal mice directly after birth for 2 weeks with an MI performed once the mice reached P7. We then analyzed the hearts following injury to determine whether malonate results in prolongation of the neonatal regenerative window (FIG. 10A). To examine whether malonate stimulates cardiomyocyte proliferation, we performed MI in 7-day-old mice and analyzed their hearts at 7 days post-MI (14-day-old) by immunostaining for markers of proliferation. We measured a significant increase in the number of cardiomyocytes undergoing mitosis as evident by pH3 staining in the dimethyl malonate-injected mice compared to saline-injected controls (FIGS. 10B and 10C). We also quantified a significant increase in the number of cardiomyocytes undergoing cytokinesis by Aurora B staining, suggesting that a significantly higher number of cardiomyocytes are undergoing complete cell division (FIGS. 10D and 10E). Furthermore, there was a significant reduction in cardiomyocyte cell size at 21 days post-MI in the dimethyl malonate-injected mice as quantified by wheat germ agglutinin staining (WGA), suggestive of newly formed cardiomyocytes and a reduction in cardiomyocyte hypertrophy (FIGS. 10F and 10G). To determine whether this increase in cardiomyocyte proliferation results in improved regeneration in the P7 mouse heart, we performed trichrome staining at 21 days post-MI to quantify structural regeneration and fibrosis. As expected, lack of myocardium regeneration and persistence of fibrotic scarring was detected below the ligature plane of the saline-injected controls. In contrast, mice that were injected with dimethyl malonate demonstrated complete heart regeneration (FIGS. 10H and 11). More importantly, cardiac function assessed by EF, FS, LVIDD, and LVIDS in the dimethyl malonate-injected hearts was restored to normal levels (FIG. 10I and Table 2). These data indicate that SDH inhibition by malonate can promote cardiomyocyte proliferation and extend the regenerative capacity of the neonatal mouse heart beyond 1 week after birth, resulting in a complete regenerative response following MI in P7 juvenile mice.

SDH Inhibition by Atpenin A5 Recapitulates the Regenerative Effect of Malonate

Figure 12A:
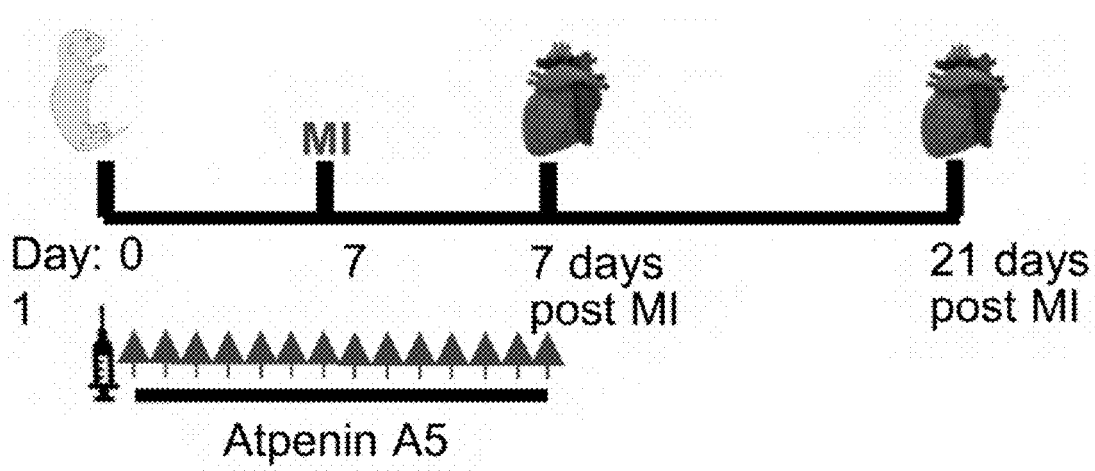
FIGS. 12A-12H. SDH inhibition by Atpenin A5 promotes cardiomyocyte mitosis and regeneration in the postnatal heart following MI.
Figure 12B:
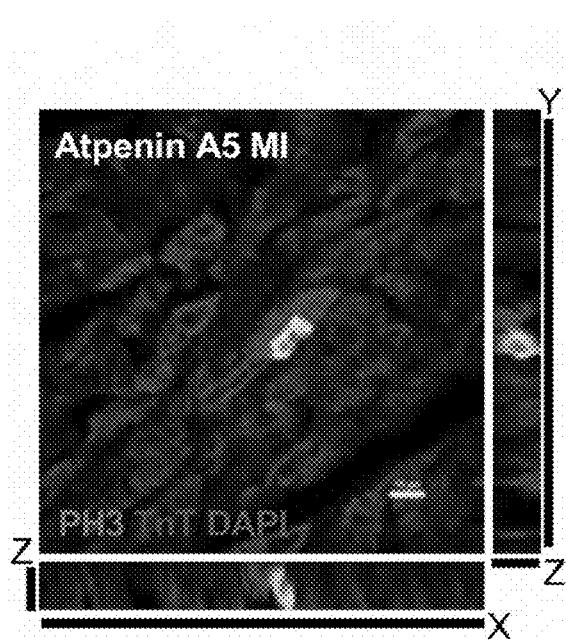
Figure 12C:
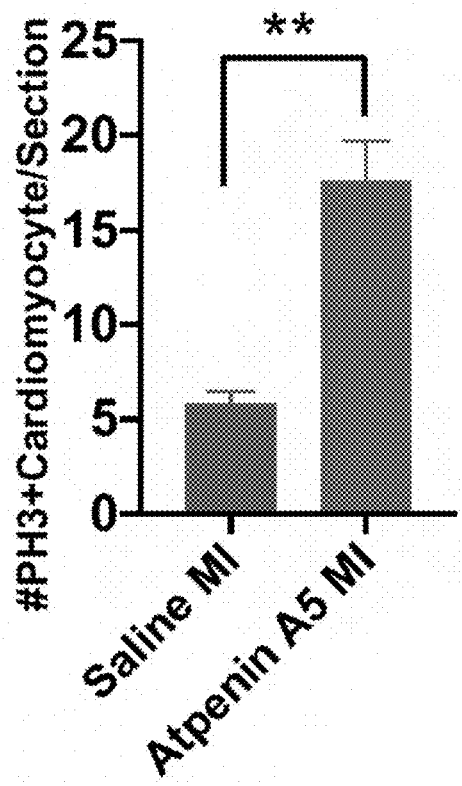
Figure 12D:
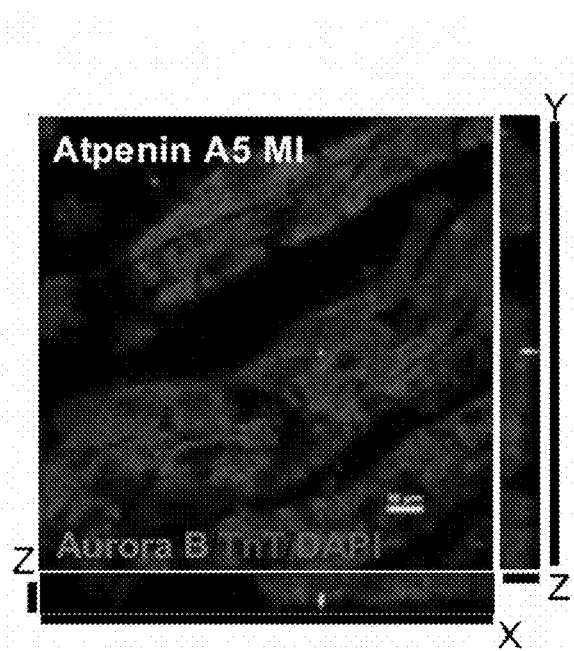
Figure 12E:
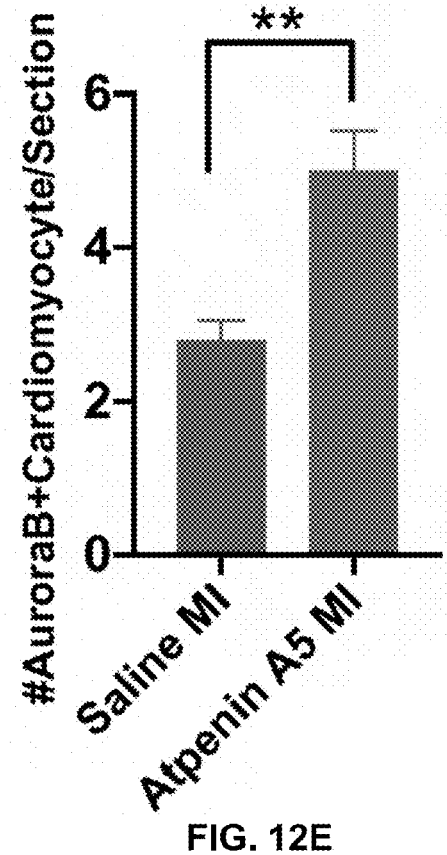
Figure 12G:
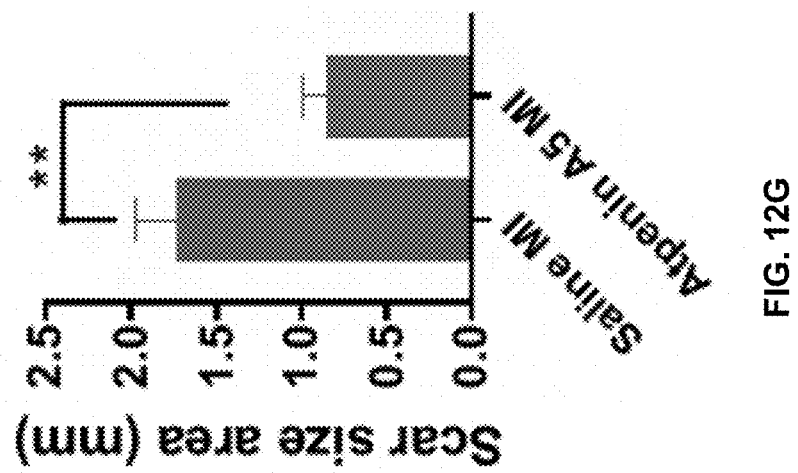
Figure 12F:
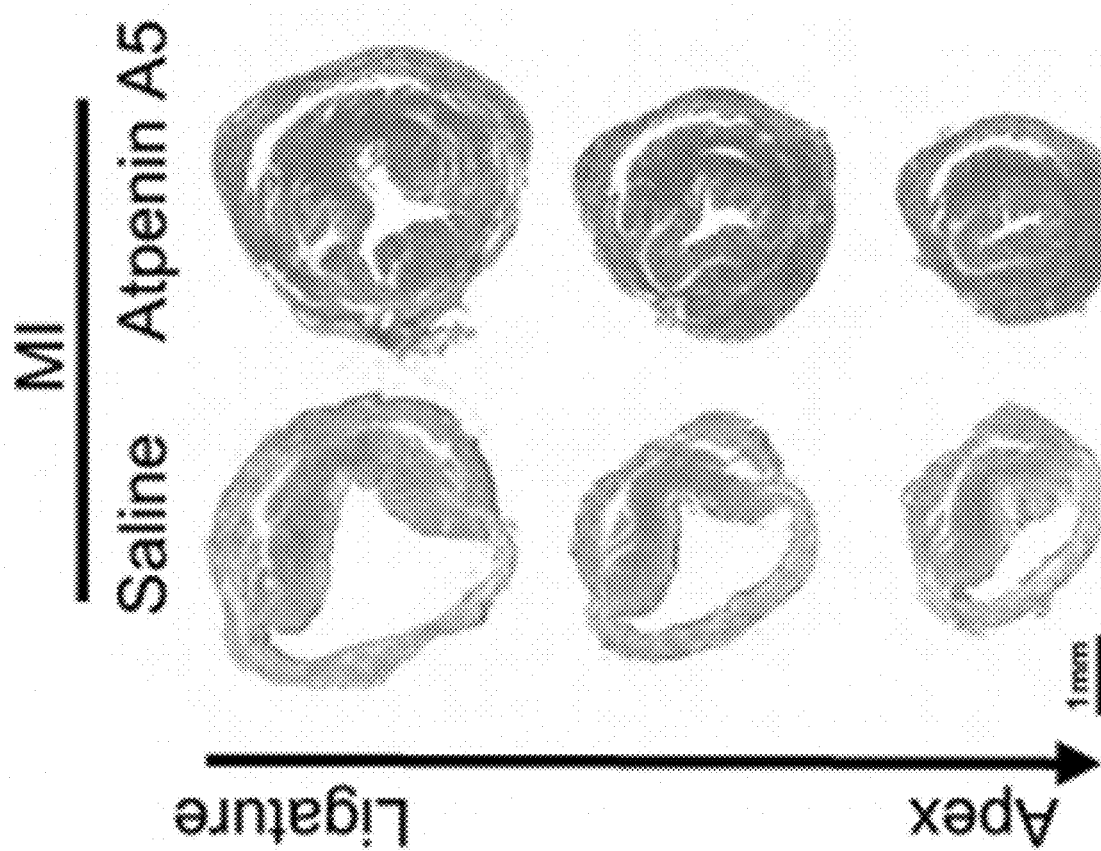
Figure 12H:
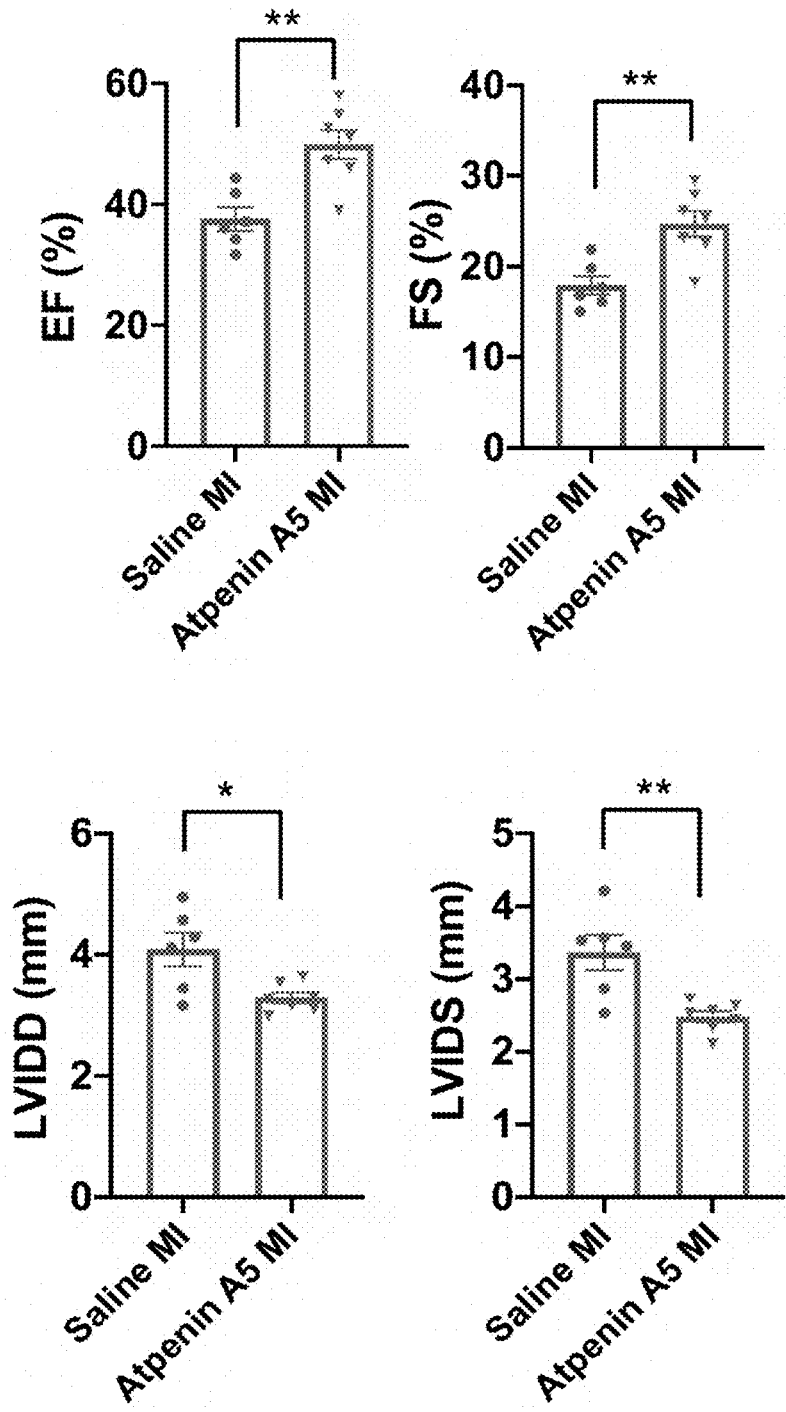

To establish that malonate promotes cardiomyocyte proliferation and heart regeneration via SDH inhibition, we used a similar treatment strategy using Atpenin A5, which is a potent inhibitor of SDH (FIG. 12A)[21]. To determine whether Atpenin A5 treatment can stimulate cardiomyocyte proliferation in the non-regenerative heart, we performed MI in P7 mice and analyzed their hearts at 7 days post-MI for markers of proliferation. We quantified a significant increase in the percentage of cardiomyocytes undergoing mitosis and cytokinesis as evident by pH3 and Aurora B staining, respectively, in the Atpenin A5-injected mice compared to controls (FIGS. 12B-12E). To determine whether SDH inhibition by Atpenin A5 regenerates the non-regenerating P7 mouse heart similar to malonate, we performed trichrome staining at 21 days post-MI to quantify fibrosis and myocardial regeneration. Atpenin A5-injected mice demonstrated myocardial thickness at the infarct zone and a significant reduction in scar size compared to controls (FIGS. 12F and 12G). This was concomitant with restoration of cardiac function in Atpenin A5-injected mice (FIG. 12H and Table 3). Our results demonstrate that Atpenin A5 restores cardiac structure and function similar to malonate, suggesting that SDH inhibition is a central mechanism by which malonate promotes heart regeneration.

TABLE 2

The fundamental measured and calculated echocardiography parameters of saline- and malonate-injected hearts (P7D21).

|  | Saline | | Malonate | |
| --- | --- | --- | --- | --- |
|  | SH (n = 5) | MI (n = 8) | SH (n = 6) | MI (n = 6) |
| Measurement |  |  |  |  |
| LVIDD (mm) | 2.565 ± 0.133 | 3.370 ± 0.142 | 3.240 ± 0.185 | 2.490 ± 0.269 |
| LVPWD (mm) | 0.629 ± 0.013 | 0.680 ± 0.019 | 0.643 ± 0.026 | 0.684 ± 0.037 |
| LVIDS (mm) | 1.715 ± 0.135 | 2.601 ± 0.114 | 2.058 ± 0.204 | 1.578 ± 0.259 |
| LVPWS (mm) | 0.722 ± 0.017 | 0.792 ± 0.015 | 0.818 ± 0.032 | 0.823 ± 0.022 |
| LVAWD (mm) | 0.635 ± 0.018 | 0.680 ± 0.017 | 0.650 ± 0.025 | 0.702 ± 0.029 |
| LVAWS (mm) | 0.749 ± 0.017 | 0.794 ± 0.014 | 0.820 ± 0.033 | 0.814 ± 0.023 |
| Calculation |  |  |  |  |
| LV Vol; d (µL) | 24.258 ± 3.073 | 47.325 ± 4.672 | 43.309 ± 5.883 | 24.289 ± 5.739 |
| LV Vol; s (µL) | 9.020 ± 1.674 | 25.215 ± 2.609 | 14.962 ± 3.612 | 8.741 ± 3.350 |
| % EF | 63.978 ± 3.151 | 46.890 ± 1.165 | 67.727 ± 3.762 | 69.751 ± 5.496 |
| % FS | 33.439 ± 2.328 | 22.802 ± 0.657 | 37.135 ± 2.848 | 38.443 ± 4.043 |
| LV Mass (mg) | 41.500 ± 2.617 | 71.870 ± 5.442 | 62.439 ± 4.833 | 48.029 ± 9.293 |
| HR (BPM) | 386.400 ± 34.086 | 423.500 ± 25.944 | 401.000 ± 28.109 | 435.667 ± 24.313 |

Notes.
SH = Sham.
MI = Myocardial Infarction.
LVIDD = Left Ventricle Internal Diameter Diastole.
LVPWD = Left Ventricle Posterior Wall Thickness Diastole.
LVIDS = Left Ventricle Internal Diameter Systole.
LVPWS = Left Ventricle Posterior Wall Thickness Systole.
LVAWD = Left Ventricle Anterior Wall Thickness Diastole.
LVAWS = Left Ventricle Anterior Wall Thickness Systole.
LV Vol; d = Left Ventricular Volume; diastole.
LV Vol; s = Left Ventricular Volume; systole.
% EF = Ejection Fraction.
% FS = Fractional Shortening.
LV Mass = Left Ventricular Mass (Anatomical Weight).
HR = Heart Rate.
Data are expressed as mean ± SE.

TABLE 3

The fundamental measured and calculated echocardiography parameters of saline- and Atpenin A5-injected hearts (P7D21).

| | Saline | | Atpenin A5 | |
| --- | --- | --- | --- | --- |
| | SH (n = 6) | MI (n = 6) | SH (n = 6) | MI (n = 8) |
| Measurement | | | | |
| LVIDD (mm) | 3.590 ± 0.181 | 4.090 ± 0.276 | 3.100 ± 0.229 | 3.438 ± 0.167 |
| LVPWD (mm) | 0.647 ± 0.011 | 0.652 ± 0.012 | 0.536 ± 0.027 | 0.521 ± 0.025 |
| LVIDS (mm) | 2.665 ± 0.186 | 3.360 ± 0.240 | 2.319 ± 0.221 | 2.592 ± 0.132 |
| LVPWS (mm) | 0.802 ± 0.012 | 0.780 ± 0.018 | 0.648 ± 0.030 | 0.643 ± 0.027 |
| LVAWD (mm) | 0.650 ± 0.009 | 0.652 ± 0.015 | 0.493 ± 0.042 | 0.525 ± 0.023 |
| LVAWS (mm) | 0.793 ± 0.016 | 0.773 ± 0.011 | 0.615 ± 0.041 | 0.644 ± 0.032 |
| Calculation | | | | |
| LV Vol; d (µL) | 55.167 ± 6.529 | 76.347 ± 11.574 | 39.614 ± 7.039 | 50.033 ± 6.416 |
| LV Vol; s (µL) | 27.221 ± 4.753 | 48.016 ± 7.944 | 19.979 ± 4.374 | 25.290 ± 3.427 |
| % EF | 51.964 ± 3.085 | 37.574 ± 1.930 | 51.652 ± 3.984 | 49.676 ± 2.072 |
| % FS | 26.109 ± 1.760 | 17.903 ± 1.032 | 25.773 ± 2.586 | 24.642 ± 1.227 |
| LV Mass (mg) | 74.382 ± 5.083 | 94.979 ± 11.087 | 42.822 ± 4.210 | 54.203 ± 7.978 |
| HR (BPM) | 404.333 ± 9.319 | 398.000 ± 28.112 | 426.833 ± 19.170 | 387.000 ± 22.475 |

Notes.
SH = Sham.
MI = Myocardial Infarction.
LVIDD = Left Ventricle Internal Diameter Diastole.
LVPWD = Left Ventricle Posterior Wall Thickness Diastole.
LVIDS = Left Ventricle Internal Diameter Systole.
LVPWS = Left Ventricle Posterior Wall Thickness Systole.
LVAWD = Left Ventricle Anterior Wall Thickness Diastole.
LVAWS = Left Ventricle Anterior Wall Thickness Systole.
LV Vol; d = Left Ventricular Volume; diastole.
LV Vol; s = Left Ventricular Volume; systole.
% EF = Ejection Fraction.
% FS = Fractional Shortening.
LV Mass = Left Ventricular Mass (Anatomical Weight).
HR = Heart Rate.
Data are expressed as mean ± SE.

Figure 13A:
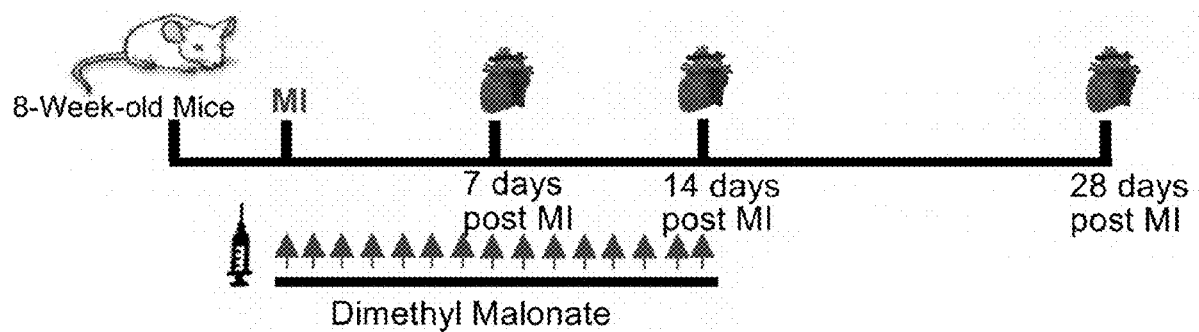
FIGS. 13A-13I. Malonate promotes adult cardiomyocyte proliferation following MI.
Figure 13B:
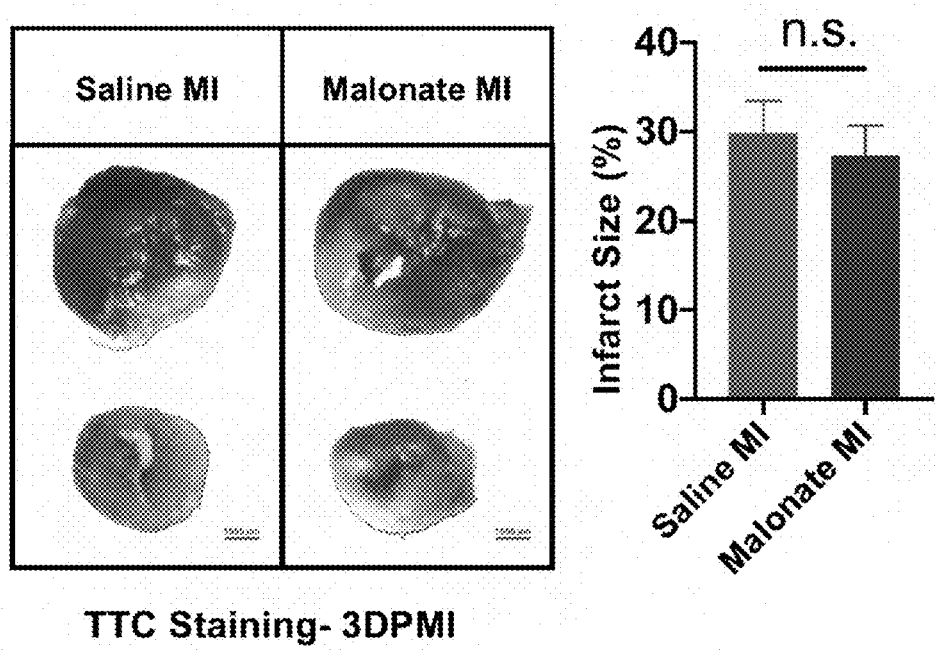
Figure 13C:
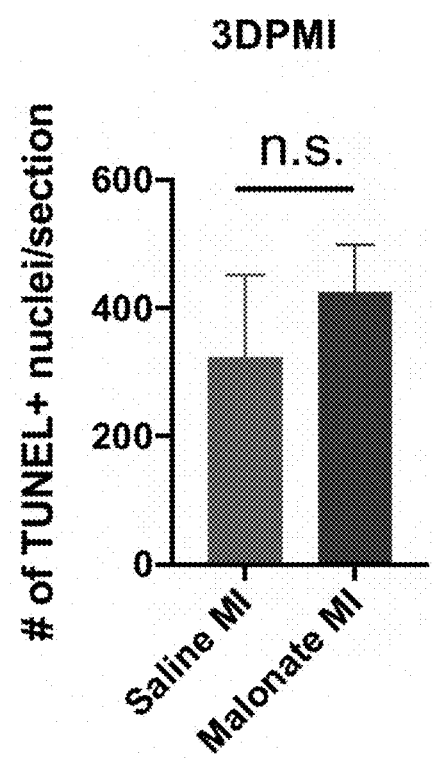
Figure 14:
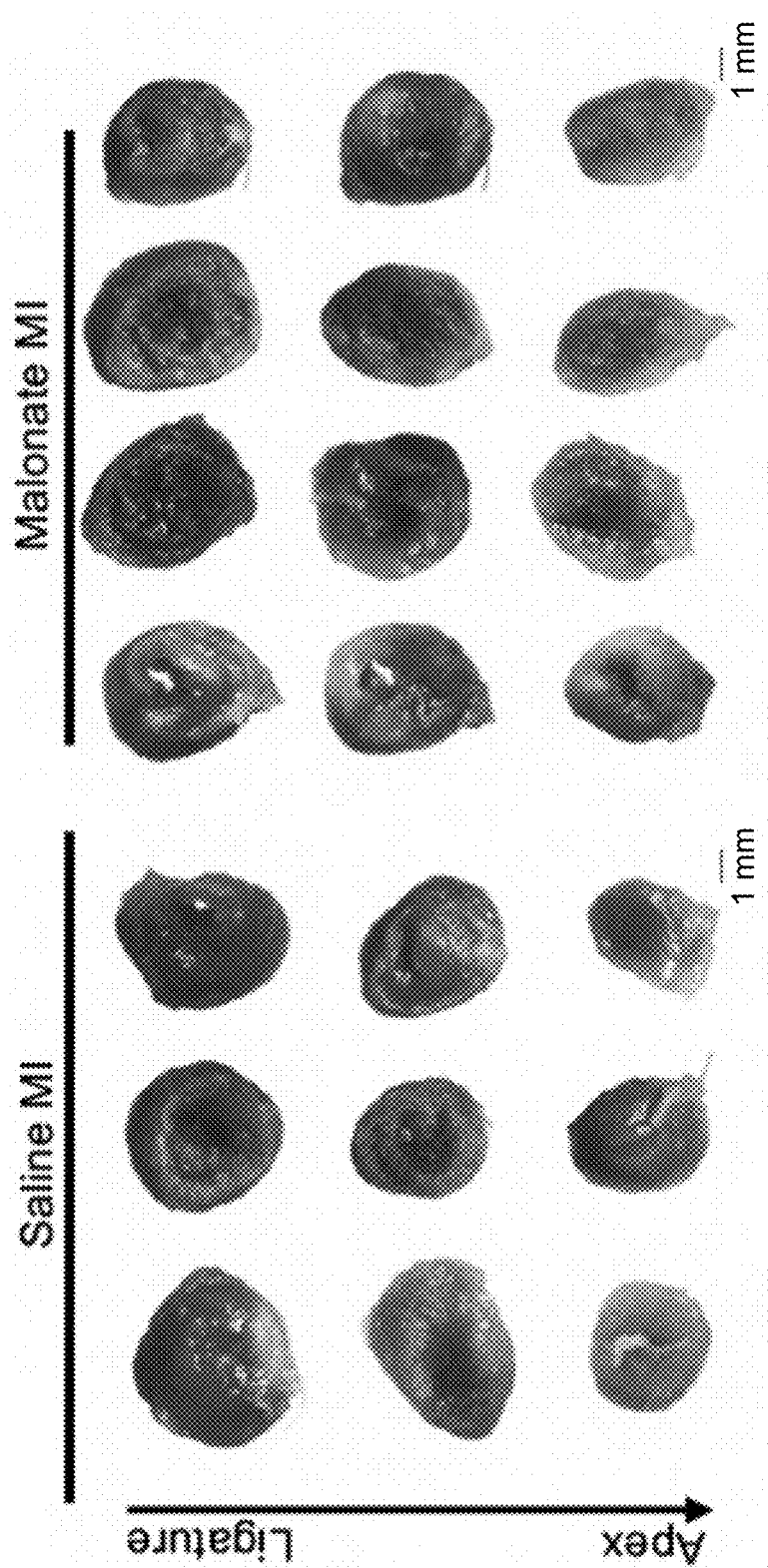
FIG. 14. Triphenyl tetrazolium chloride (TTC) of fresh hearts from saline or malonate-injected adult mice at 3 days post MI. All hearts are shown.
Figure 15:
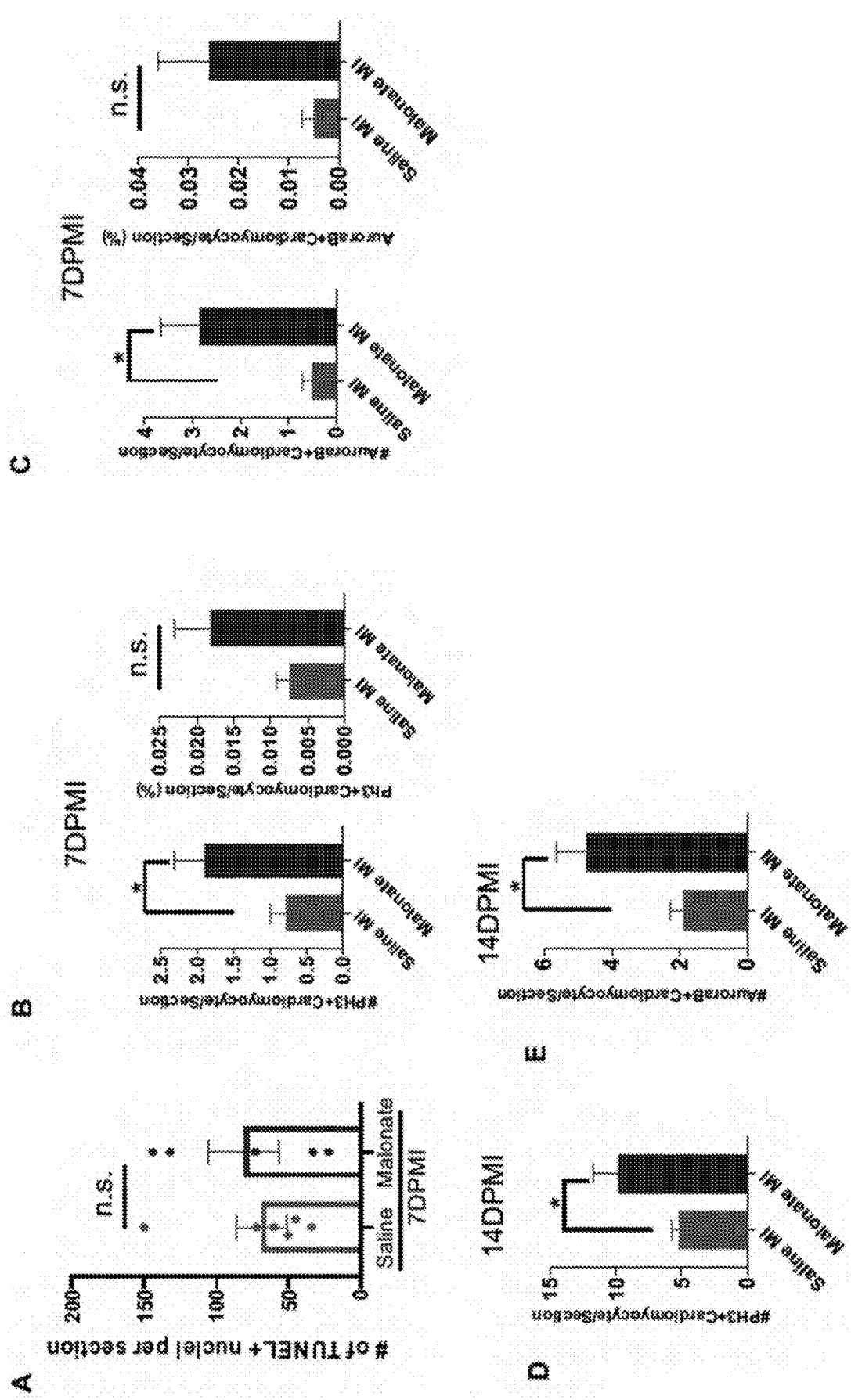
FIG. 15. Quantification of immunostaining of paraffin heart sections from saline and malonate-injected mice at 7 and 14 days post adult MI. Quantification of (A) TUNEL positive nuclei, (B) PH3 positive cardiomyocytes, (C) Aurora B positive cardiomyocytes, at 7 days post MI. Quantification of number of (D) PH3 and (E) Aurora B positive cardiomyocytes at 14 days post MI per section.

SDH Inhibitors Promotes Cardiomyocyte Proliferation and Heart Regeneration in Adult Mice Following Myocardial Infarction The ability of SDH inhibitors to promote cardiomyocyte proliferation and heart regeneration beyond the 1-week postnatal regenerative window in mice raises the question of whether SDH inhibitors can metabolically reprogram the adult heart to a regenerative state following injury. To address this question, we performed MI in 8-week-old mice and injected either saline or dimethyl malonate (100 mg/kg) within an hour following MI and continued this treatment daily for two weeks (FIG. 13A). Although SDH inhibition by malonate results in cardioprotection from reperfusion injury, whether SDH inhibitors can protect the myocardium following infarction remains undetermined. To determine whether SDH inhibitors protect against infarction similar to reperfusion injury, we performed a viability stain using triphenyltetrazolium chloride (TTC) at 3 days post-MI. Quantification of the non-viable myocardium (white) in heart sections below the ligature showed no significant difference in both saline and malonate-injected mice, suggesting that malonate did not protect against myocardial necrosis following infarction (FIGS. 13B and 14). In addition, there was no difference in the number of apoptotic cardiomyocytes at 3- or 7-days post-MI in saline- and dimethyl malonate-injected hearts as quantified by TdT-mediated dUTP nick-end labelling (TUNEL) staining (FIGS. 13C and 15 (A)). These results demonstrate that malonate did not protect against infarction and cardiomyocyte death following adult MI.

Figure 13D:
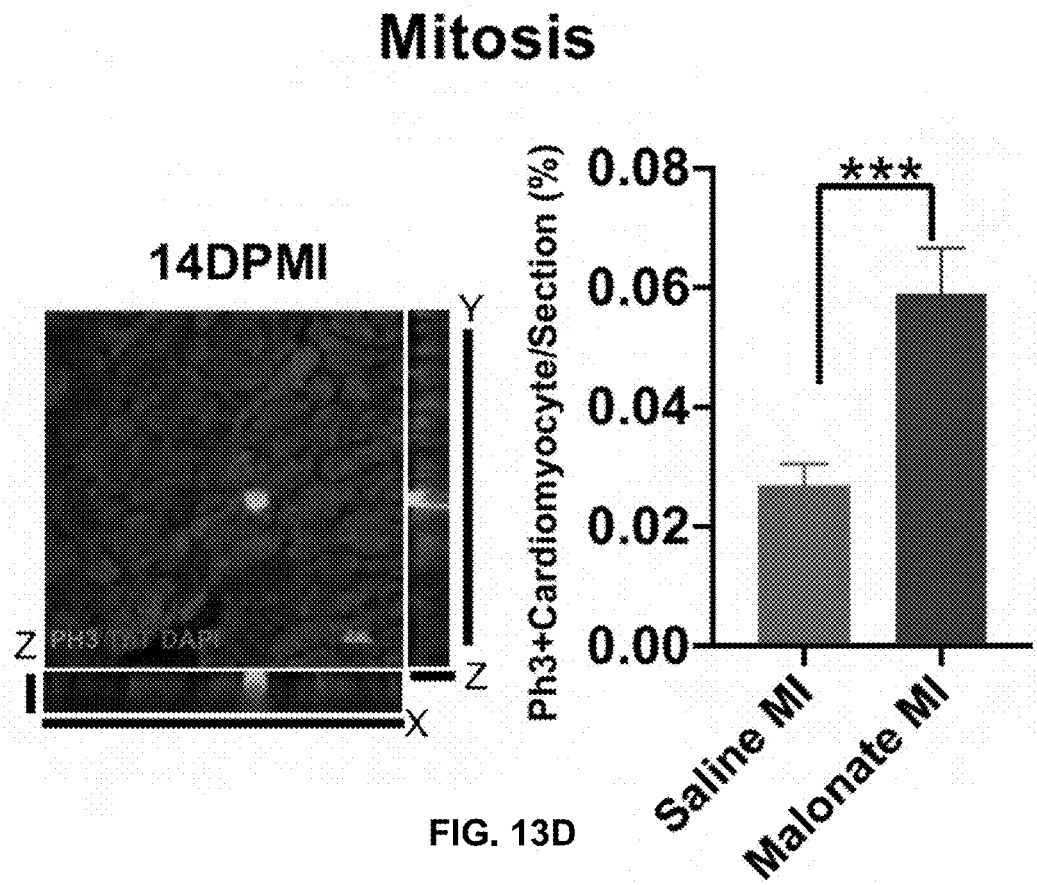
Figure 13E:
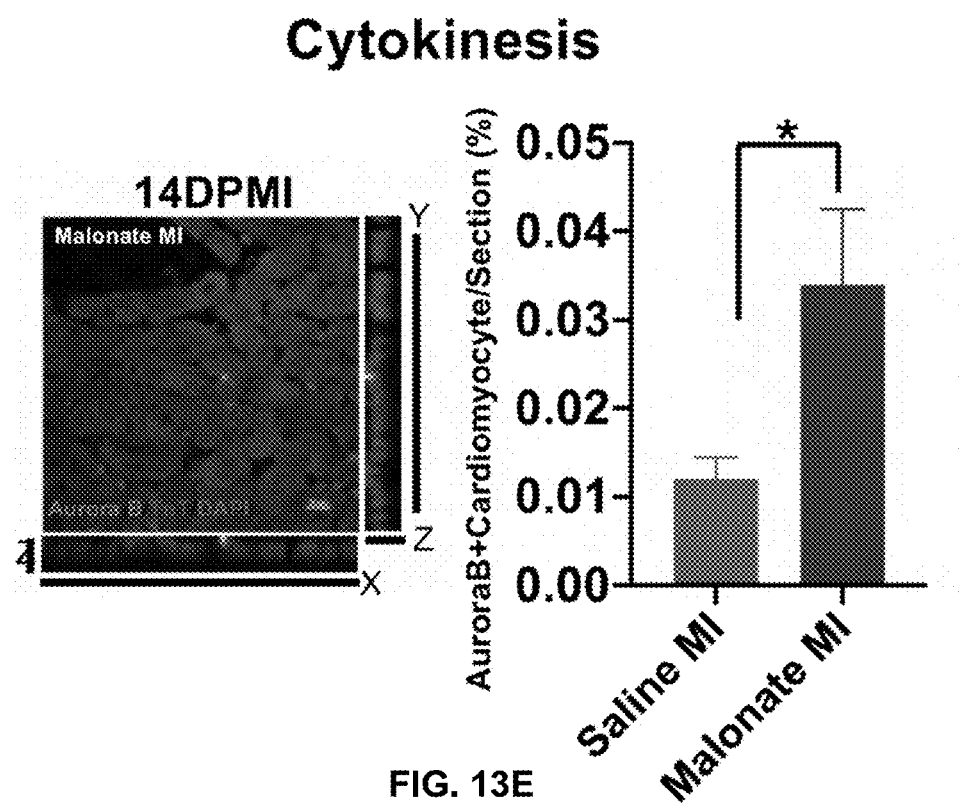
Figure 13F:
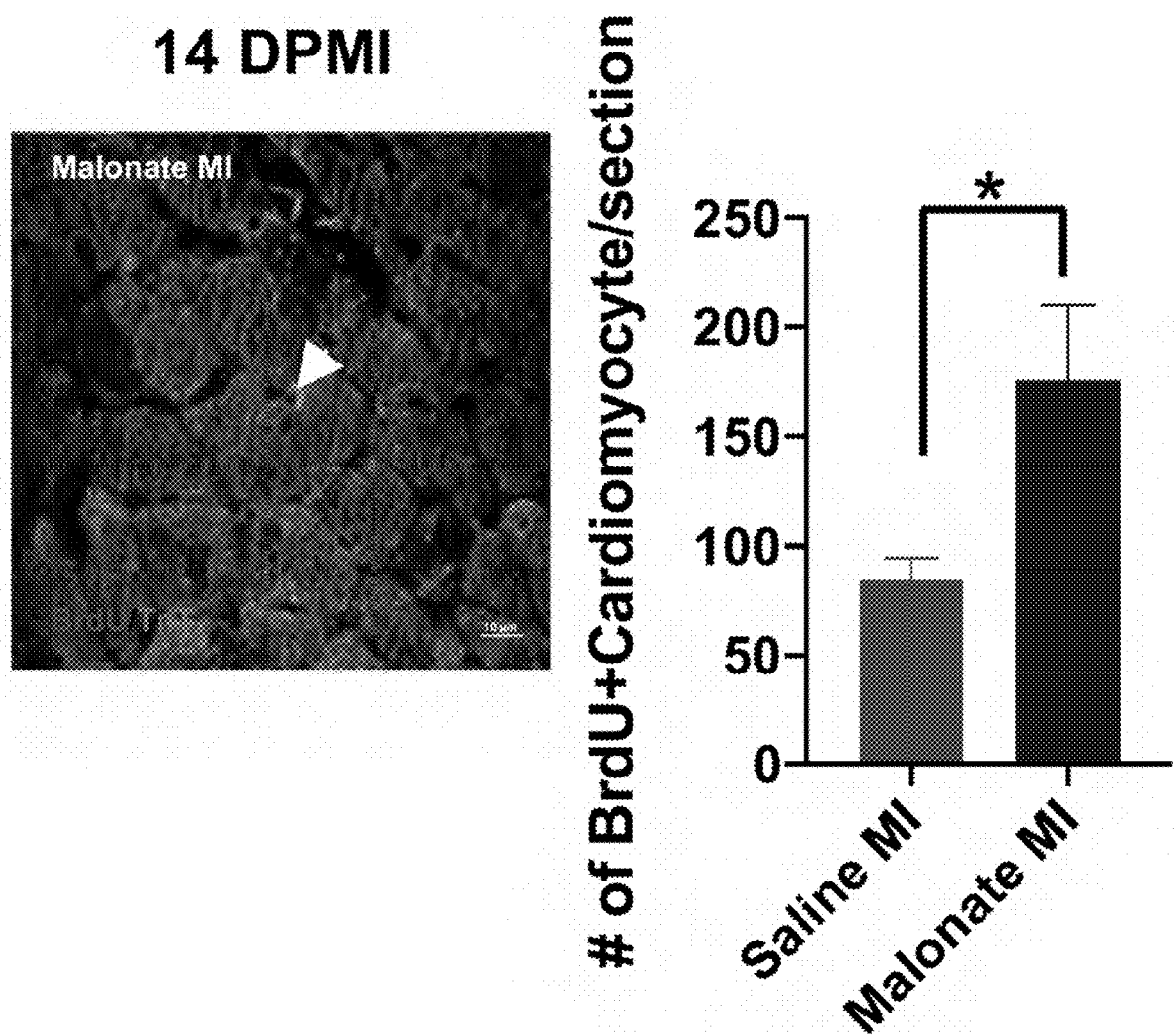
Figure 13G:
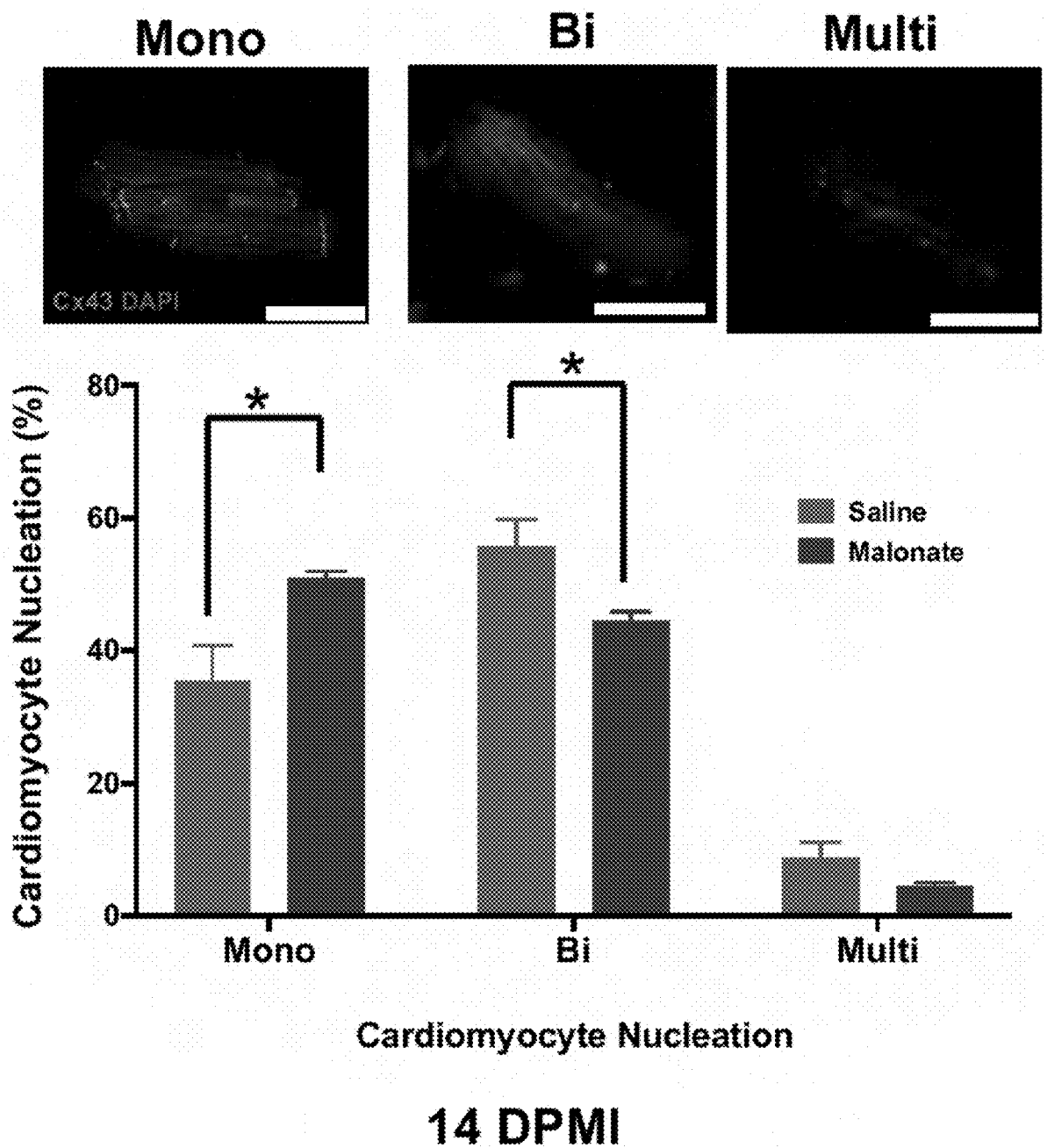
Figure 13H:
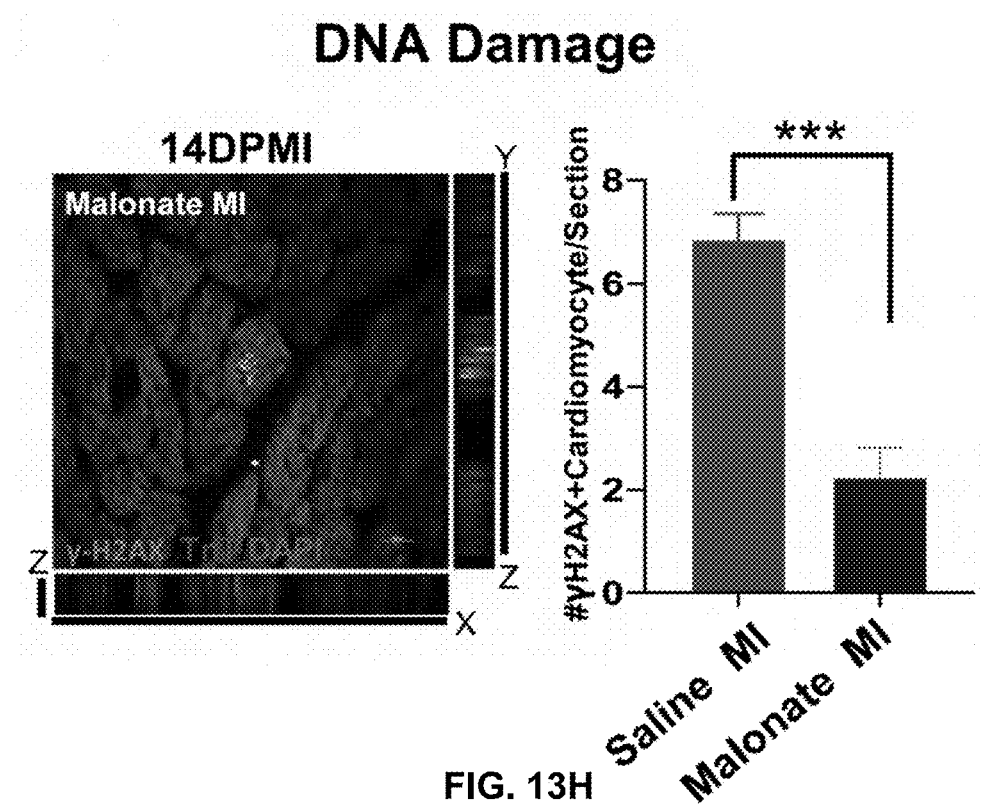

To determine whether malonate stimulates adult cardiomyocyte proliferation, we performed immunostaining for the mitosis marker pH3 at 7- and 14 days post-MI. We quantified a significant increase in the number of cardiomyocytes undergoing mitosis in dimethyl malonate-injected hearts compared to saline-injected controls at both 7- and 14-days post-MI (FIGS. 13D and 15 (B and D)). In addition, there was a significant increase in the number of cardiomyocytes undergoing cytokinesis in dimethyl malonate-injected hearts as demonstrated by Aurora B staining at 7- and 14 days post-MI (FIGS. 13E and 15 (C and E)). Furthermore, there was a significant increase in 5-bromodeoxyuridine (BrdU) incorporation in cardiomyocytes in malonate-treated mice at 14 days post-MI (FIG. 13F). This was concomitant with a remarkable increase in the number of mononucleated cardiomyocytes and a significant decrease in the number of binucleated cardiomyocytes in the malonate-treated mice (FIG. 13G). Additionally, we quantified a significant decrease in the number of cardiomyocytes with γH2AX foci in malonate-treated mice indicating a significant reduction in cardiomyocyte DNA damage (FIG. 13H). These results suggest that malonate can promote adult cardiomyocyte cell cycle activity following MI.

Figure 13I:
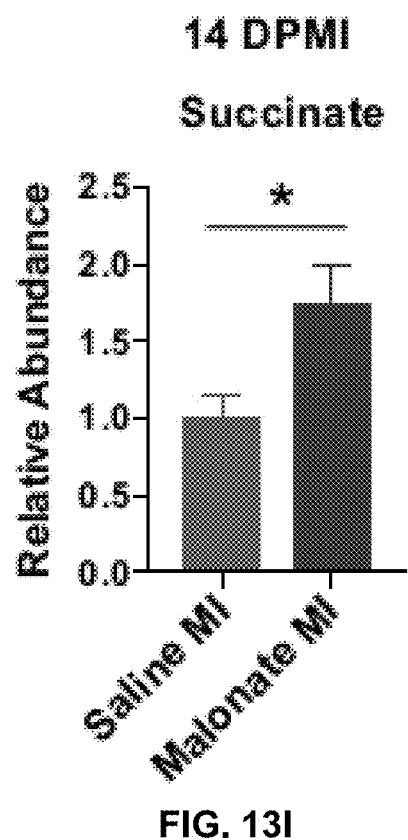

To determine whether SDH inhibition regulates cardiomyocyte cell cycle activity by modulating succinate levels, we measured the levels of intracellular succinate by liquid chromatography-mass spectrometry (LC-MS). Interestingly, there was a significant increase in succinate levels in the hearts of malonate-treated mice at 14 days post-MI (FIG. 13I). This is in line with multiple studies showing that SDH inhibition and subsequent blockade of oxidative phosphorylation is accompanied by an increase in succinate levels, which promotes metabolic reprogramming to aerobic glycolysis in cancer[22-24]. This is distinct from the cardioprotective role of malonate in reperfusion injury, which confers cardioprotection by inhibiting reverse activity of SDH that prevents succinate accumulation[7]. This suggests that malonate might promote cardiomyocyte cell cycle activity via metabolic reprogramming, rather than preventing succinate accumulation.

Figure 16A:
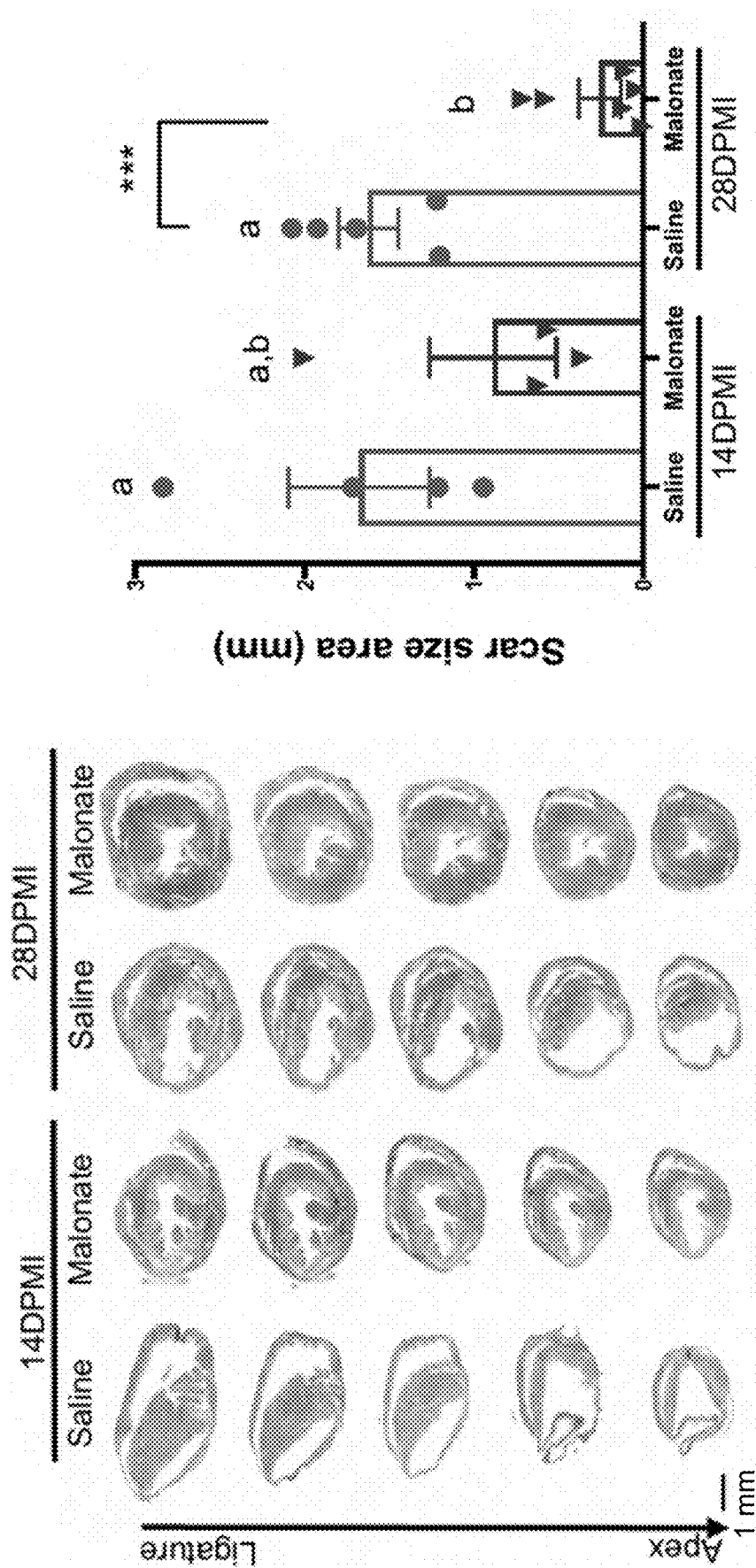
FIGS. 16A-16D. Malonate restores cardiac structure and function following adult MI.
Figure 17:
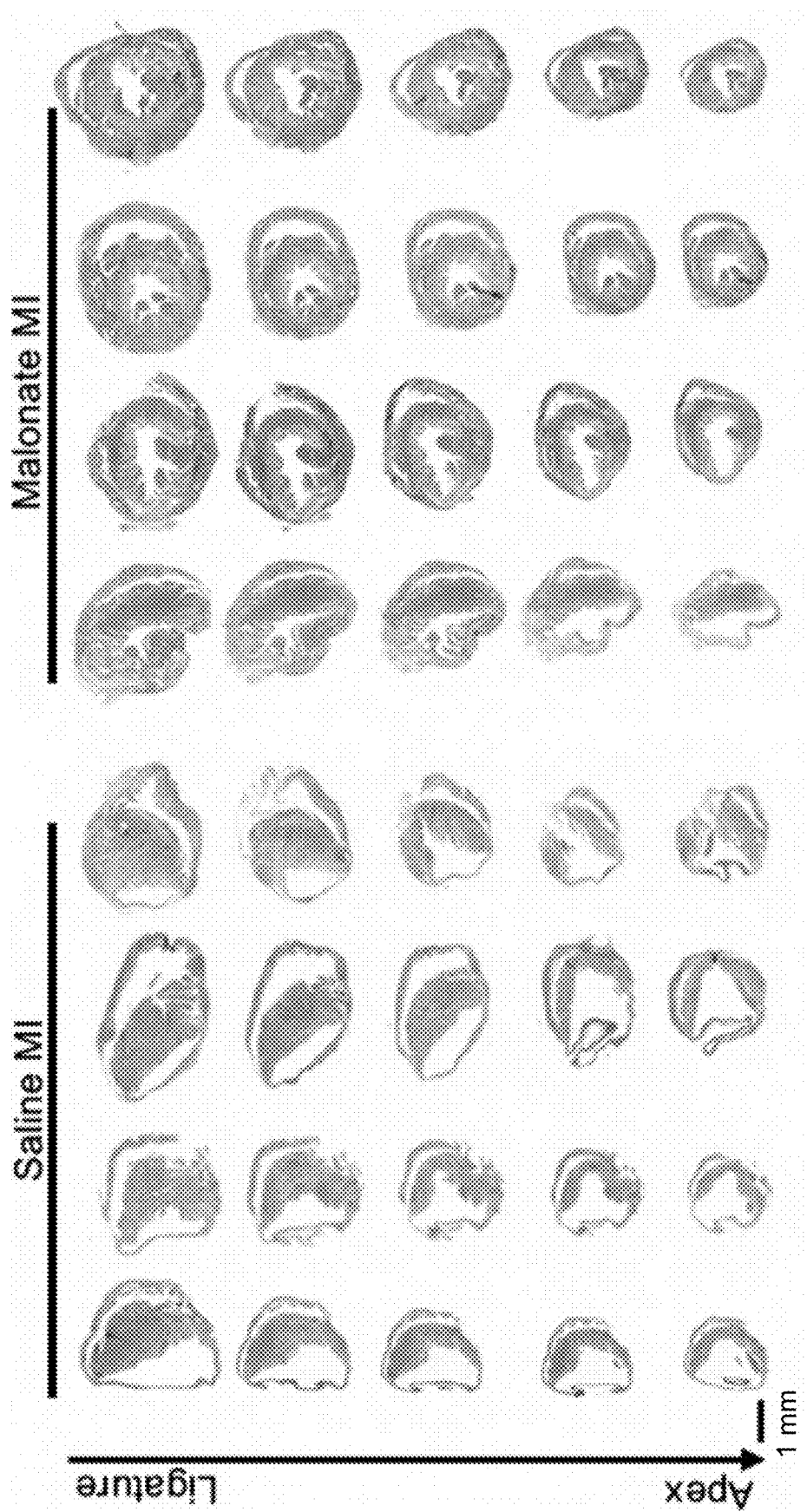
FIG. 17. Masson's trichrome-stained heart sections of saline or malonate-injected mice at 14 days post MI performed at 8 weeks old. Serial sections were cut from the site of the ligature to the apex. All hearts are shown.
Figure 18A:
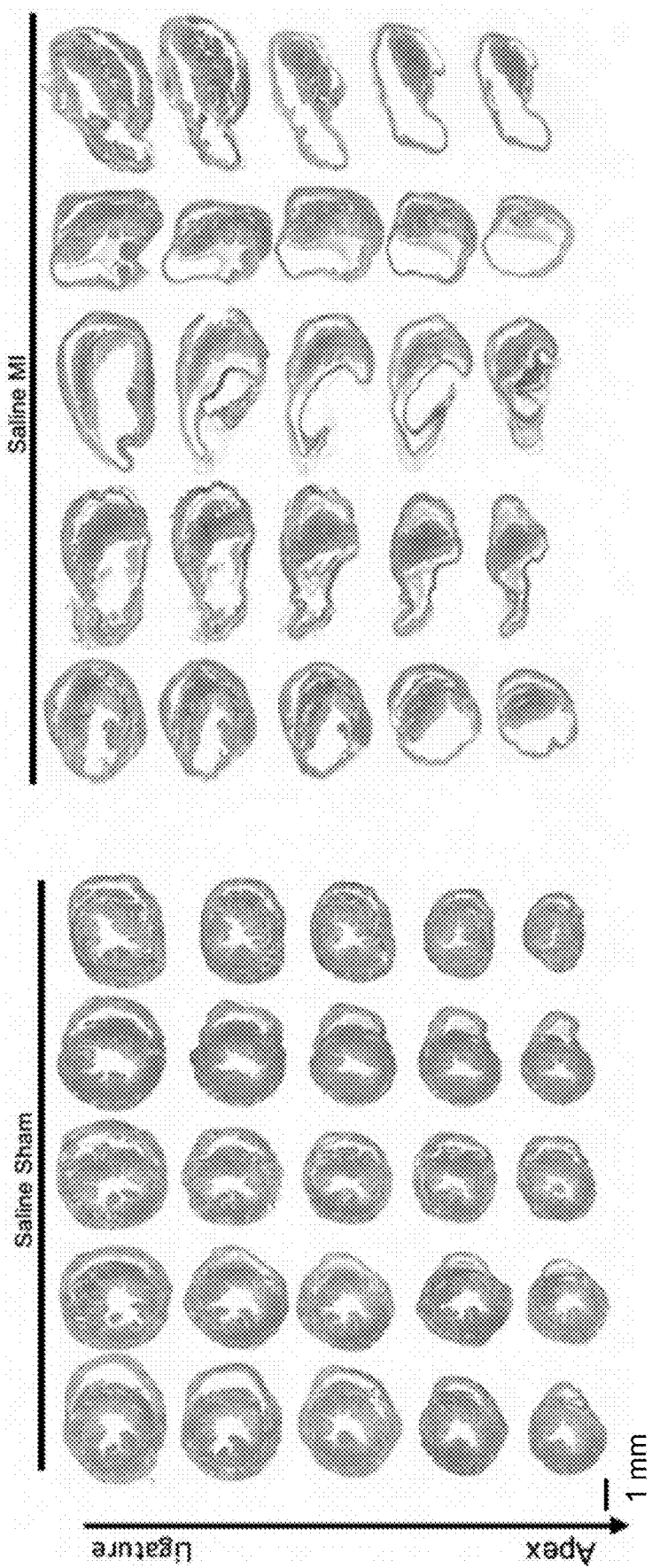
FIGS. 18A and 18B. Masson's trichrome-stained heart sections of saline-injected (FIG. 18A) or malonate-injected (FIG. 18B) mice for 14 days post-MI, harvested at 28 days post MI. Serial sections were cut from the site of the ligature to the apex. All hearts are shown.
Figure 18B:
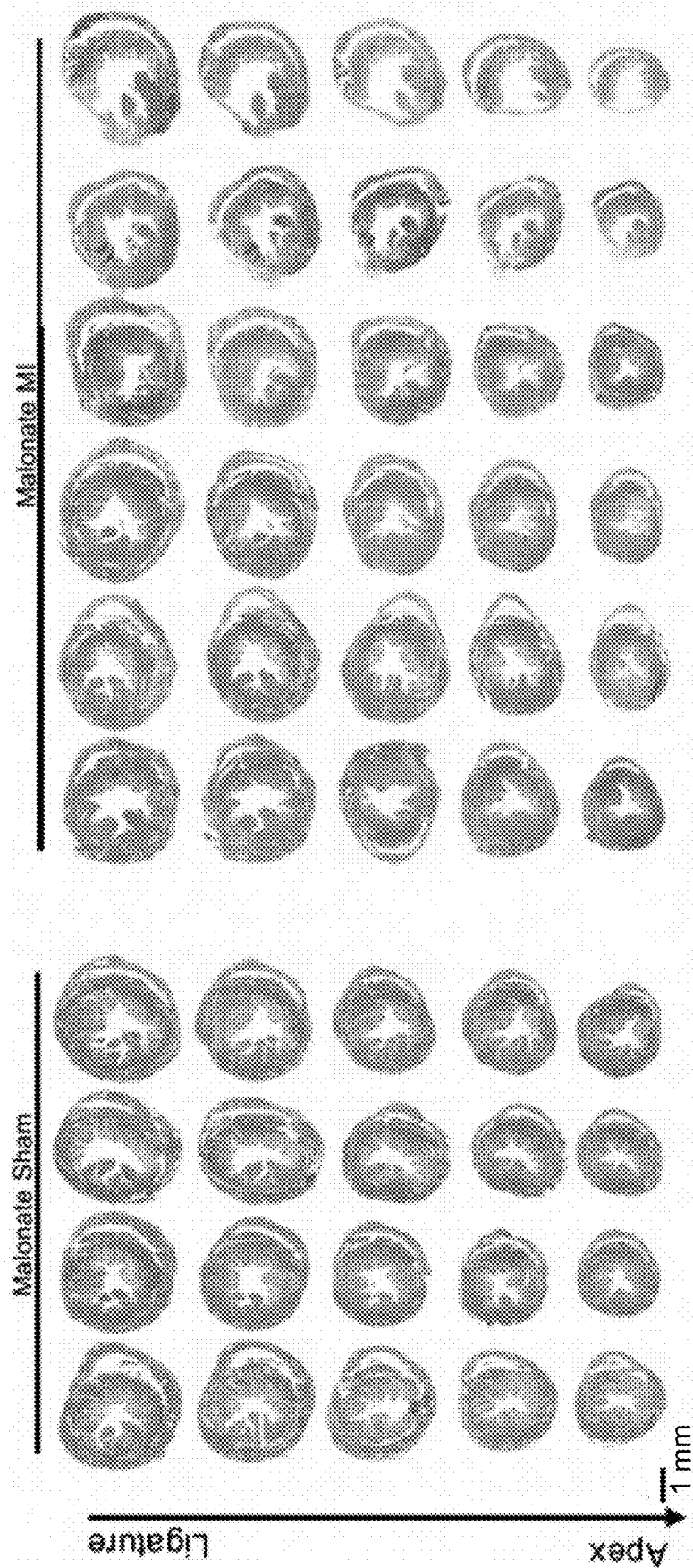

We then collected the hearts of both saline and dimethyl malonate-treated adult mice at 14- and 28-days post-MI and quantified structural regeneration by trichrome staining. By 14 days, fibrotic scarring in heart sections was evident in both dimethyl malonate-treated mice and saline-treated control (FIGS. 16A and 17). Quantification showed a trend for reduction in fibrosis in the dimethyl malonate-treated samples compared to controls at 14 days post-MI, but the difference was not significant (FIG. 16A). By 28 days post-MI, trichrome staining from the dimethyl malonate-injected hearts showed remarkable restoration of the myocardium with minimal fibrosis compared to the saline-injected controls that showed ventricle dilation and significant fibrotic scarring, as expected from an adult MI (FIGS. 16A, 18A, and 18B). Quantification of fibrosis demonstrated a significant reduction of scar size in the dimethyl malonate-treated mice at 28 days post-MI. Notably, there was incomplete regeneration in one mouse heart that was subjected to a large infarct (FIGS. 18A and 18B), indicating that the size of infarction can impact the regenerative response, similar to neonatal mouse heart regeneration[25]. Whether longer duration of malonate treatment can regenerate larger infarcts is yet to be determined.

Figure 16B:
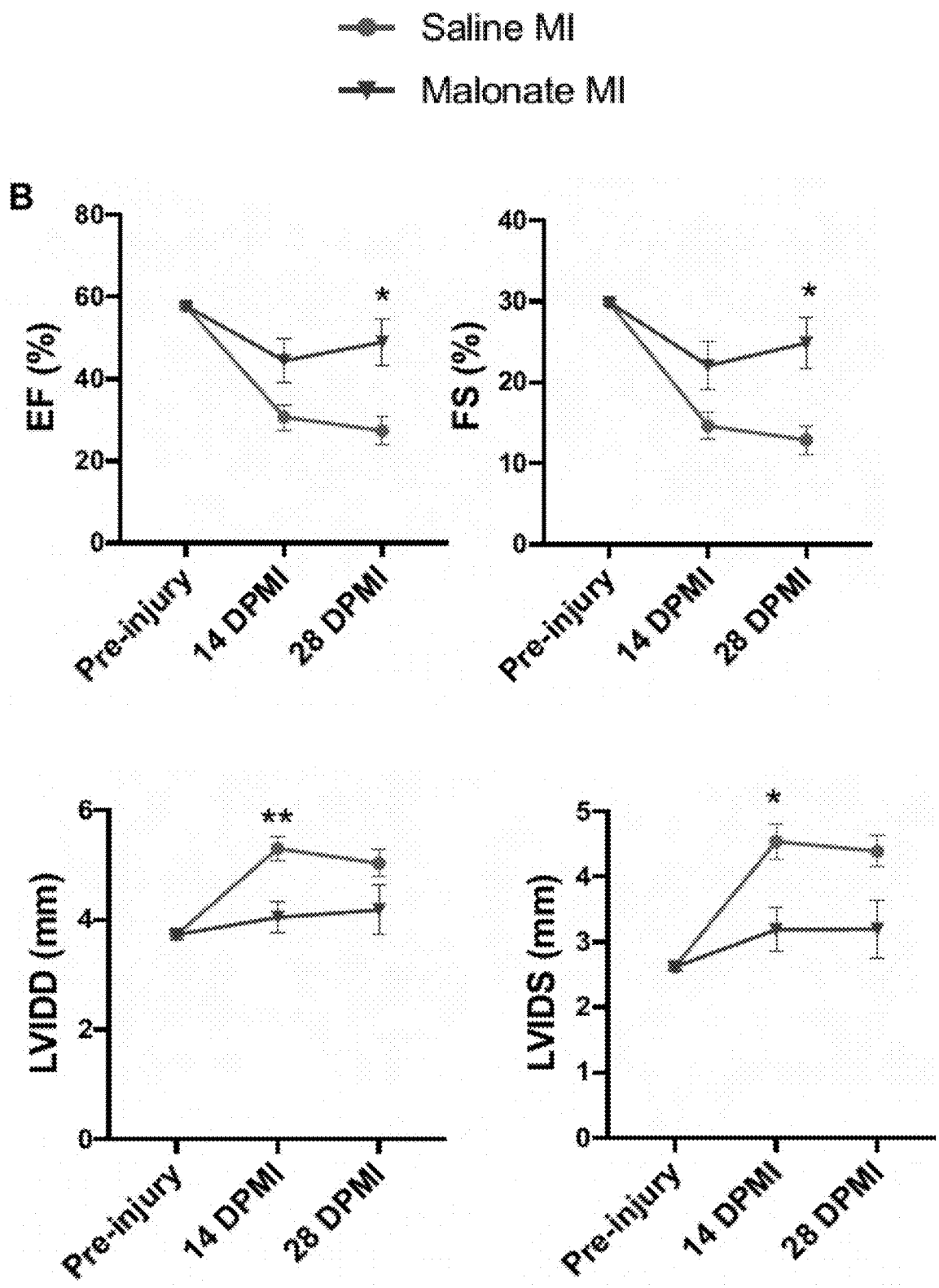
Figure 16C:
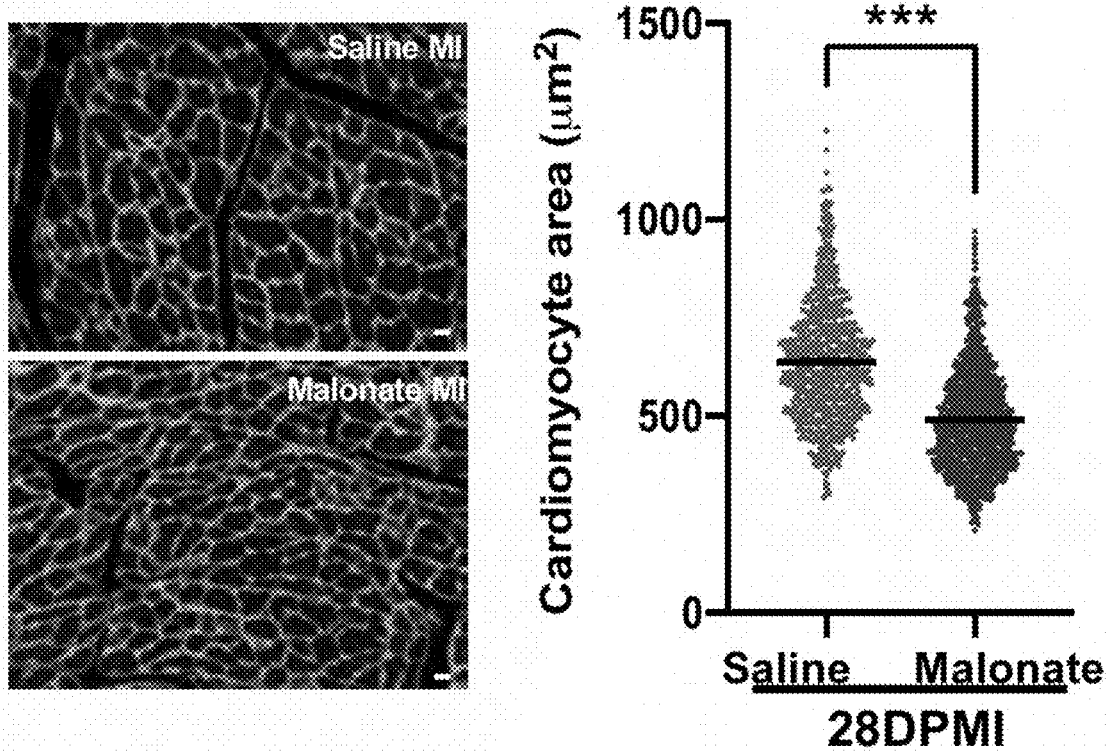
Figure 16D:
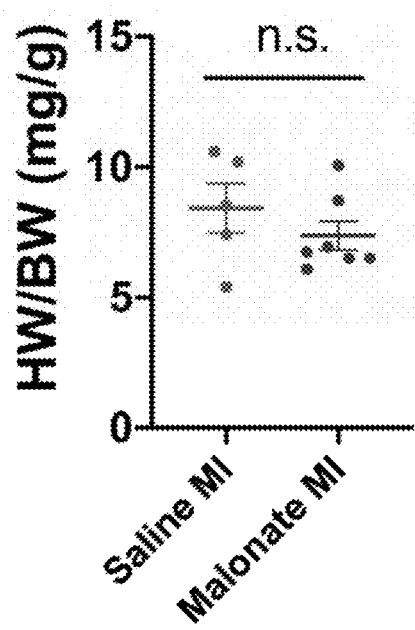

To determine whether this restoration of cardiac structure was accompanied by improvement in cardiac function, we performed echocardiographic measurements of both saline and dimethyl malonate-injected mice at 14- and 28-days post-MI. Our echocardiographic measurements demonstrated a reduction in cardiac function at 14 days post-MI (FIG. 16B and Tables 4A and 4B). There was a trending improvement in cardiac function of dimethyl malonate-injected hearts compared to controls by 14 days post-MI, but the difference was not significant (FIG. 16B). Remarkably, there was a significant improvement of cardiac function in dimethyl malonate-injected mice as measured by EF and FS at 28 days post-MI (FIG. 16B). Interestingly, there was a significant reduction in cardiomyocyte size in dimethyl malonate-injected mice compared to controls at 28 days post-MI as quantified by WGA staining (FIG. 16C). No significant differences in heart weight to body weight ratios were detected (FIG. 16D). Our results reveal that malonate is capable of restoring cardiac structure and function following adult MI. Collectively, these results demonstrate that malonate promotes adult cardiomyocyte proliferation and heart regeneration following adult MI.

TABLE 4A

The fundamental measured and calculated echocardiography parameters of saline-injected adult mice hearts.

|  | | Saline | | | |
|---|---|---|---|---|---|
|  | | SH | | MI | |
|  | Baseline | 14 DPMI | 28 DPMI | 14 DPMI | 28 DPMI |
| Measurement | | | | | |
| LVIDD (mm) | 3.731 ± 0.086 | 3.860 ± 0.268 | 3.902 ± 0.269 | 5.300 ± 0.223 | 5.032 ± 0.244 |
| LVPWD (mm) | 0.639 ± 0.006 | 0.646 ± 0.015 | 0.638 ± 0.013 | 0.528 ± 0.051 | 0.538 ± 0.036 |
| LVIDS (mm) | 2.619 ± 0.072 | 2.636 ± 0.247 | 2.776 ± 0.255 | 4.540 ± 0.267 | 4.388 ± 0.241 |
| LVPWS (mm) | 0.769 ± 0.005 | 0.790 ± 0.016 | 0.776 ± 0.023 | 0.664 ± 0.054 | 0.680 ± 0.034 |
| LVAWD (mm) | 0.641 ± 0.006 | 0.626 ± 0.018 | 0.638 ± 0.017 | 0.542 ± 0.027 | 0.572 ± 0.030 |
| LVAWS (mm) | 0.767 ± 0.005 | 0.774 ± 0.026 | 0.764 ± 0.025 | 0.662 ± 0.034 | 0.696 ± 0.023 |
| Calculation | | | | | |
| LV Vol; d (μL) | 59.761 ± 3.319 | 66.183 ± 10.380 | 67.892 ± 9.752 | 136.708 ± 12.866 | 121.738 ± 14.285 |
| LV Vol; s (μL) | 25.363 ± 1.705 | 27.093 ± 6.176 | 30.647 ± 5.855 | 96.225 ± 12.417 | 88.822 ± 12.143 |
| % EF | 57.761 ± 0.698 | 59.157 ± 5.946 | 56.083 ± 4.599 | 30.670 ± 3.111 | 27.369 ± 3.475 |
| % FS | 29.844 ± 0.434 | 31.633 ± 4.145 | 29.159 ± 2.850 | 14.624 ± 1.625 | 12.881 ± 1.763 |
| LV Mass (mg) | 78.043 ± 3.706 | 82.067 ± 8.035 | 85.207 ± 10.705 | 116.749 ± 13.013 | 109.525 ± 7.819 |
| HR (BPM) | 418.700 ± 11.326 | 411.800 ± 46.781 | 459.200 ± 41.189 | 413.600 ± 16.388 | 436.000 ± 23.700 |

Notes.
SH = Sham.
MI = Myocardial Infarction.
LVIDD = Left Ventricle Internal Diameter Diastole.
LVPWD = Left Ventricle Posterior Wall Thickness Diastole.
LVIDS = Left Ventricle Internal Diameter Systole.
LVPWS = Left Ventricle Posterior Wall Thickness Systole.
LVAWD = Left Ventricle Anterior Wall Thickness Diastole.
LVAWS = Left Ventricle Anterior Wall Thickness Systole.
LV Vol; d = Left Ventricular Volume; diastole.
LV Vol; s = Left Ventricular Volume; systole.
% EF = Ejection Fraction.
% FS = Fractional Shortening.
LV Mass = Left Ventricular Mass (Anatomical Weight).
HR = Heart Rate.
Data are expressed as mean ± SE.

TABLE 4B

The fundamental measured and calculated echocardiography parameters of malonate-injected adult mice hearts.

| | | Malonate | | | |
| --- | --- | --- | --- | --- | --- |
| | | SH | | MI | |
| | Baseline | 14 DPMI | 28 DPMI | 14 DPMI | 28 DPMI |
| Measurement | | | | | |
| LVIDD (mm) | 3.731 ± 0.086 | 4.005 ± 0.234 | 3.940 ± 0.137 | 4.047 ± 0.283 | 4.183 ± 0.448 |
| LVPWD (mm) | 0.639 ± 0.006 | 0.575 ± 0.035 | 0.618 ± 0.013 | 0.578 ± 0.014 | 0.600 ± 0.020 |
| LVIDS (mm) | 2.619 ± 0.072 | 2.940 ± 0.188 | 2.998 ± 0.170 | 3.188 ± 0.334 | 3.193 ± 0.451 |
| LVPWS (mm) | 0.769 ± 0.005 | 0.733 ± 0.046 | 0.753 ± 0.013 | 0.753 ± 0.016 | 0.755 ± 0.017 |
| LVAWD (mm) | 0.641 ± 0.006 | 0.575 ± 0.045 | 0.623 ± 0.014 | 0.583 ± 0.015 | 0.528 ± 0.033 |
| LVAWS (mm) | 0.767 ± 0.005 | 0.723 ± 0.047 | 0.755 ± 0.010 | 0.723 ± 0.020 | 0.693 ± 0.042 |
| Calculation | | | | | |
| LV Vol; d (µL) | 59.761 ± 3.319 | 71.304 ± 10.106 | 68.006 ± 5.647 | 74.738 ± 12.392 | 84.656 ± 22.884 |
| LV Vol; s (µL) | 25.363 ± 1.705 | 33.993 ± 5.072 | 35.538 ± 4.993 | 44.249 ± 11.125 | 47.375 ± 16.164 |
| % EF | 57.761 ± 0.698 | 52.458 ± 2.795 | 48.208 ± 3.686 | 44.421 ± 5.272 | 48.940 ± 5.707 |
| % FS | 29.844 ± 0.434 | 26.613 ± 1.724 | 24.032 ± 2.173 | 22.034 ± 2.951 | 24.858 ± 3.214 |
| LV Mass (mg) | 78.043 ± 3.706 | 78.241 ± 13.192 | 82.315 ± 5.106 | 80.024 ± 8.731 | 83.201 ± 16.390 |
| HR (BPM) | 418.700 ± 11.326 | 440.000 ± 34.578 | 463.000 ± 34.412 | 530.333 ± 14.113 | 504.833 ± 26.691 |

Notes.
SH = Sham.
MI = Myocardial Infarction.
LVIDD = Left Ventricle Internal Diameter Diastole.
LVPWD = Left Ventricle Posterior Wall Thickness Diastole.
LVIDS = Left Ventricle Internal Diameter Systole.
LVPWS = Left Ventricle Posterior Wall Thickness Systole.
LVAWD = Left Ventricle Anterior Wall Thickness Diastole.
LVAWS = Left Ventricle Anterior Wall Thickness Systole.
LV Vol; d = Left Ventricular Volume; diastole.
LV Vol; s = Left Ventricular Volume; systole.
% EF = Ejection Fraction.
% FS = Fractional Shortening.
LV Mass = Left Ventricular Mass (Anatomical Weight).
HR = Heart Rate.
Data are expressed as mean ± SE.

Malonate Induces a Metabolic Switch in the Adult Heart and Promotes Revascularization Following Infarction The metabolic switch from glycolysis to oxidative phosphorylation results in loss of the endogenous cardiac regenerative ability in mammals[6]. Furthermore, a metabolic switch to glycolysis promotes cardiomyocyte proliferation during zebrafish heart regeneration[16]. Interestingly, mutations in SDH have been demonstrated to induce a metabolic shift into glycolysis in familial cancer syndromes that promotes cell division and angiogenesis[13-15]. These studies together with our comprehensive results strongly suggest that SDH inhibition may promote a cardiac regenerative response by modulating the cardiac metabolic state. To determine whether inhibition of SDH promotes metabolic reprogramming from oxidative phosphorylation to glycolysis in the adult heart, we treated adult mice for 2 weeks with dimethyl malonate and performed metabolomics using LC-MS (FIG. 19A). There was a marked reduction in tricarboxylic acid (TCA) cycle metabolites as well as an increase in succinate levels, indicating a reduction in oxidative phosphorylation following SDH inhibition by malonate (FIG. 19B). This is consistent with previous studies showing inhibition of aerobic respiration in response to SDH inhibition, since SDH participates in both the TCA cycle and the electron transport chain (ETC)[10]. More importantly, this was accompanied by a dynamic shift in glucose metabolism and glycolytic intermediates (FIG. 19C). These results suggest that SDH inhibition by malonate stimulates a metabolic switch from oxidative phosphorylation to glycolysis in the adult heart, which is a metabolic state that promotes heart regeneration.

Figure 19D:
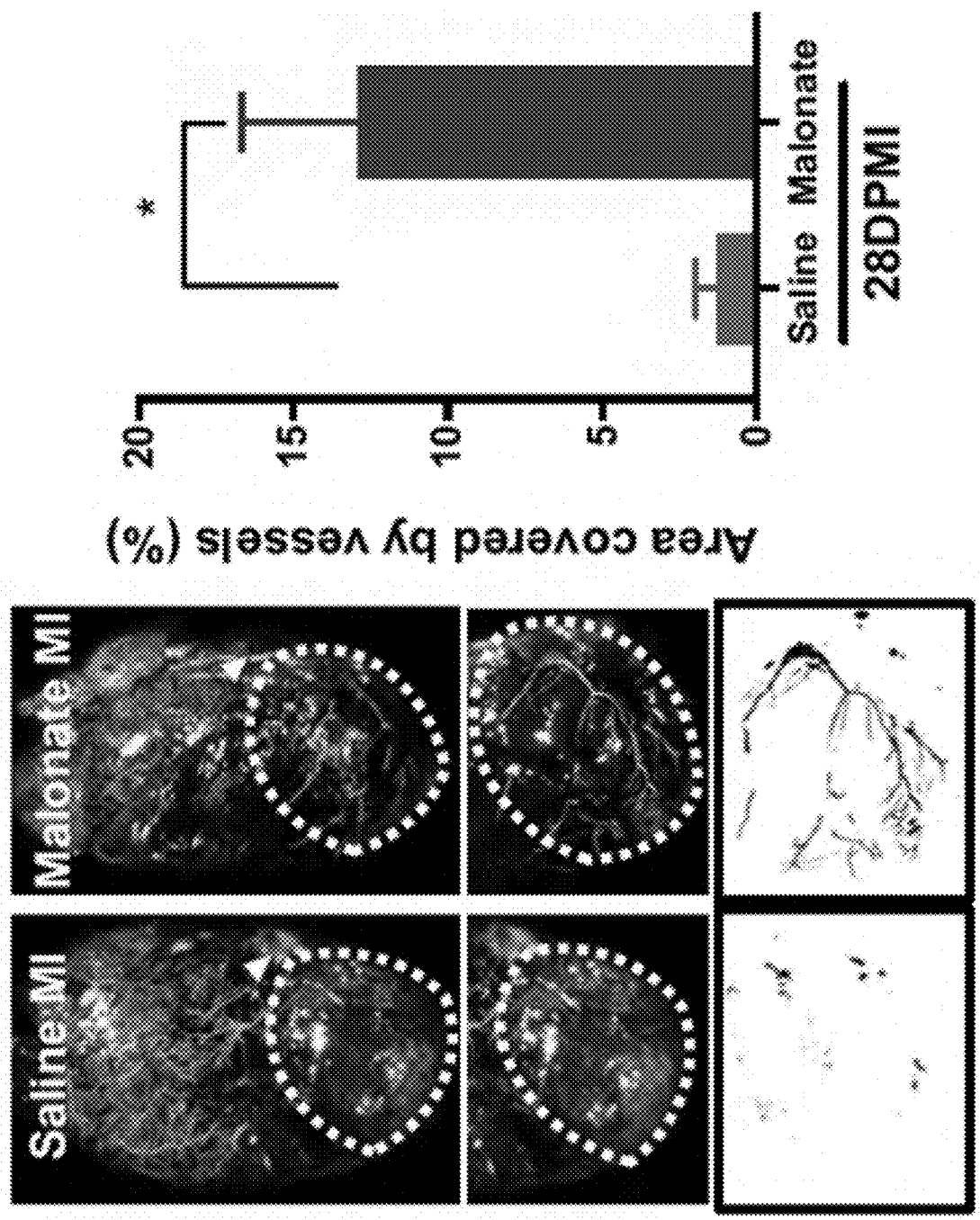
Figure 19E:
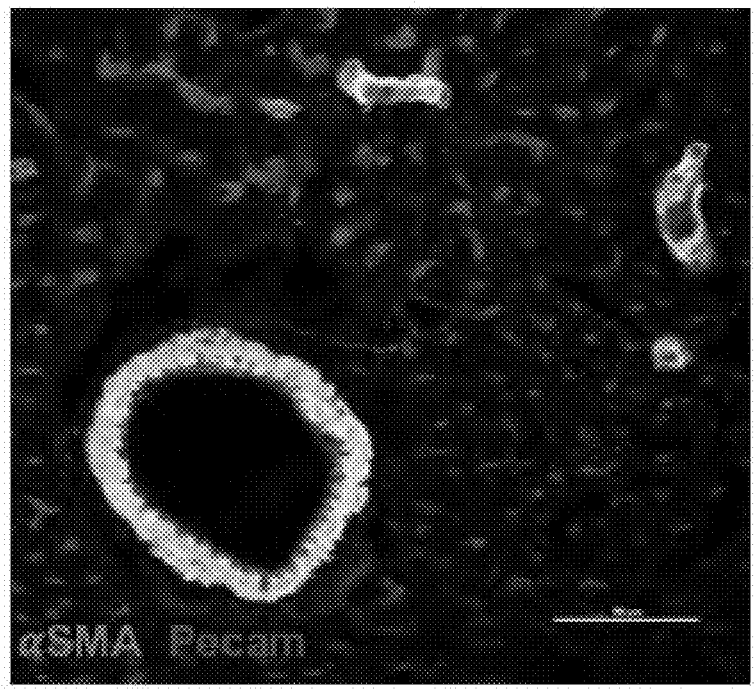
Figure 19F:
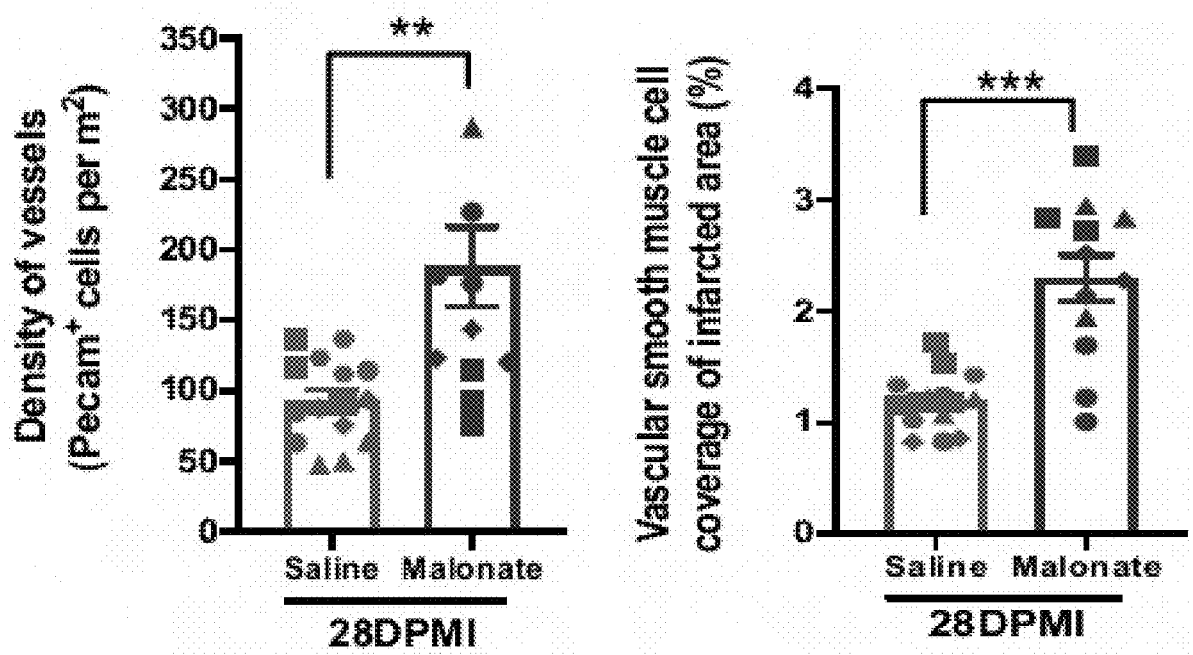

Cardiomyocyte proliferation is key to replenishing the lost myocardium following injury; however, complete regeneration following infarction requires coronary artery formation and revascularization to supply the newly formed myocardium with oxygenated blood. This response has been demonstrated to be activated during neonatal mouse regeneration and is a hallmark for complete regeneration following infarction[26]. Interestingly, glycolysis plays in important role in angiogenesis[27,28]. Since malonate treatment induces a cardiac metabolic shift in the adult heart, we wanted to determine whether malonate promotes heart regeneration by inducing coronary artery formation and revascularization following injury. To address this question, we performed coronary casting of saline and dimethyl malonate-injected hearts at 28 days post-MI. There was a remarkable formation of coronary arteries below the ligature site in the dimethyl malonate-injected mice compared to controls (FIG. 19D). In addition, there was a significant increase in capillary density and vascular smooth muscle cells in the infarct zone, suggesting an increase in newly synthesized vessels ranging in size from small capillaries to large-diameter vessels (FIGS. 19E and 19F). These results reveal that malonate can induce myocardial regeneration by stimulating adult cardiomyocyte proliferation as well as revascularization post-MI.

Figure 20A:
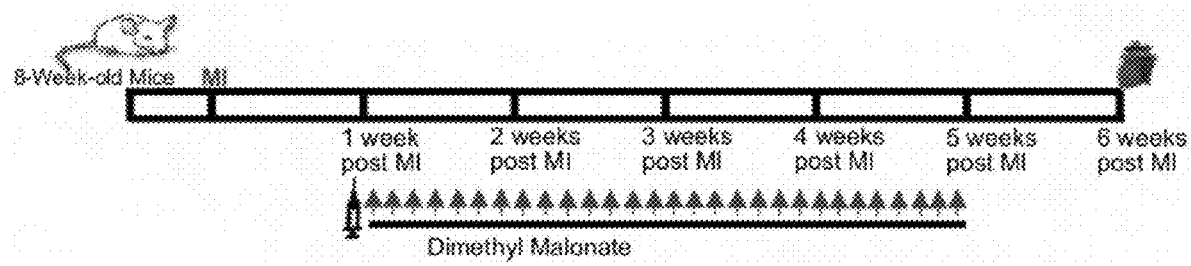
FIGS. 20A-20D. Malonate treatment starting 1-week post-MI promotes myocardial regeneration.
Figures 20B, 20C:
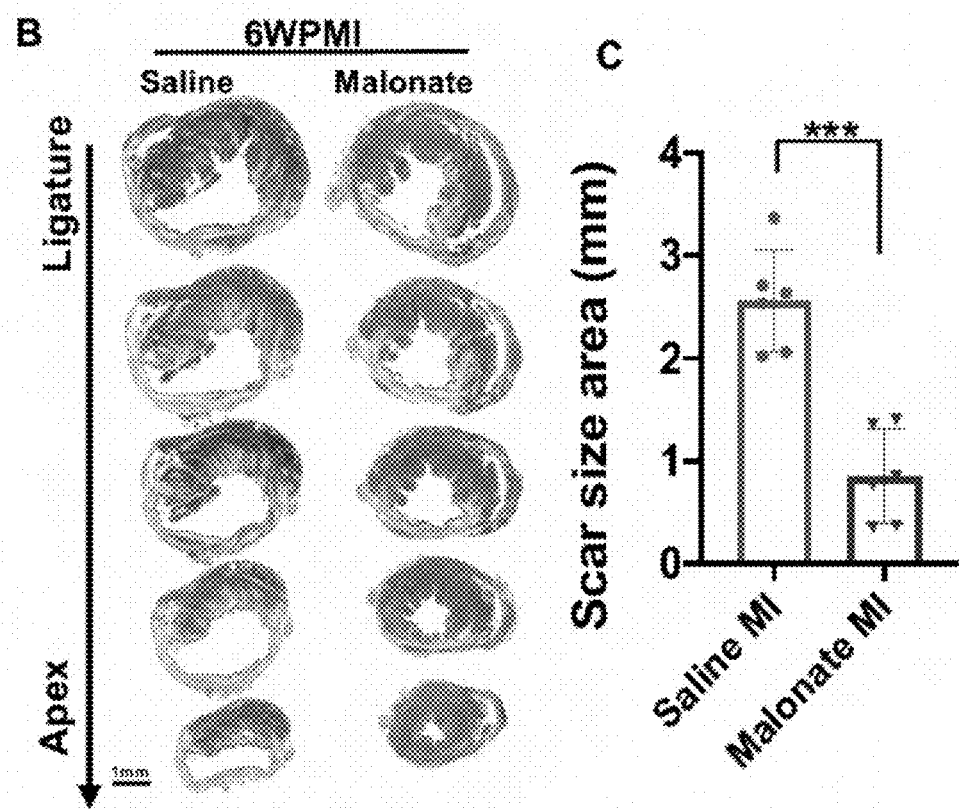
Figure 20D:
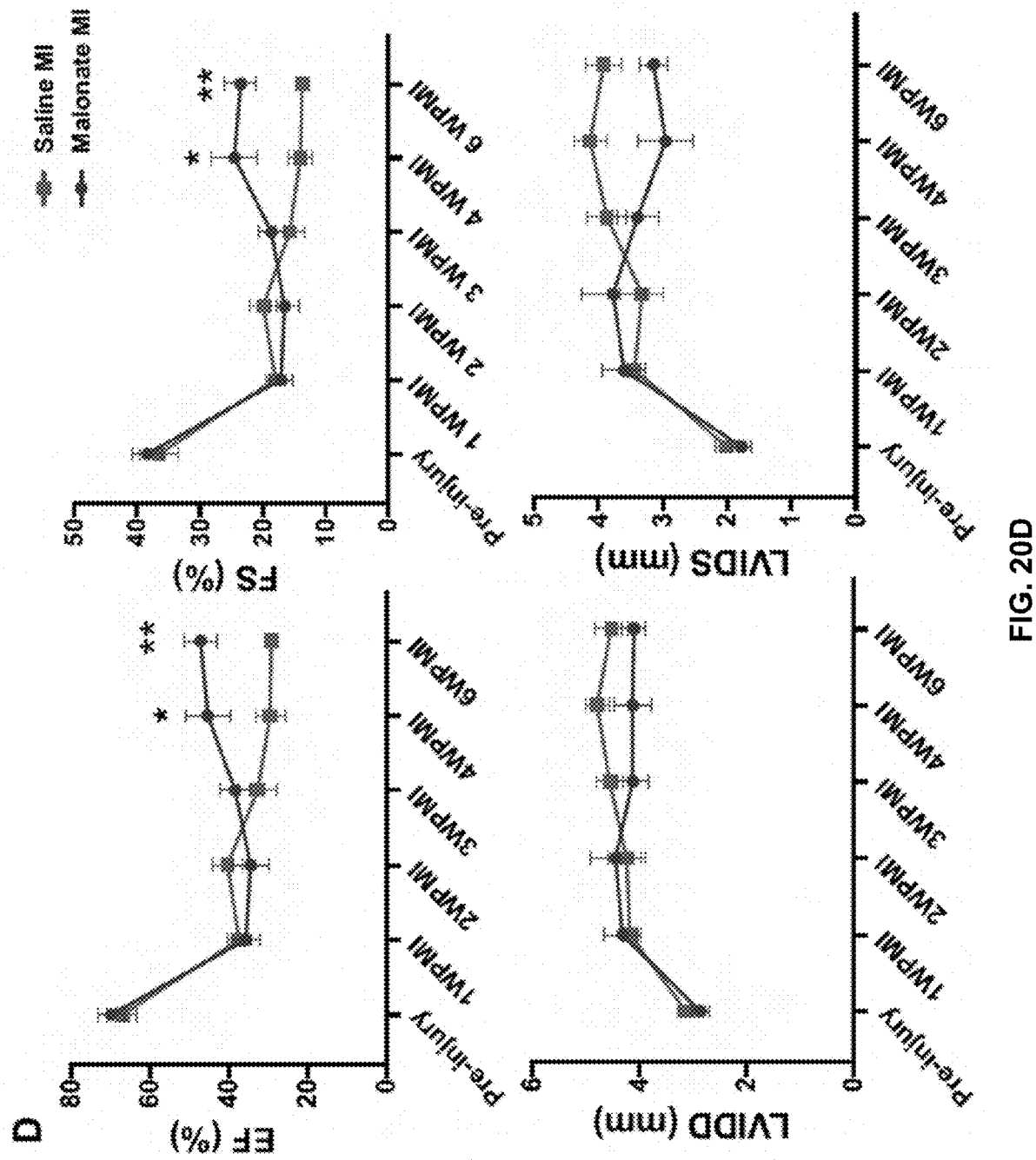
Figure 21A:
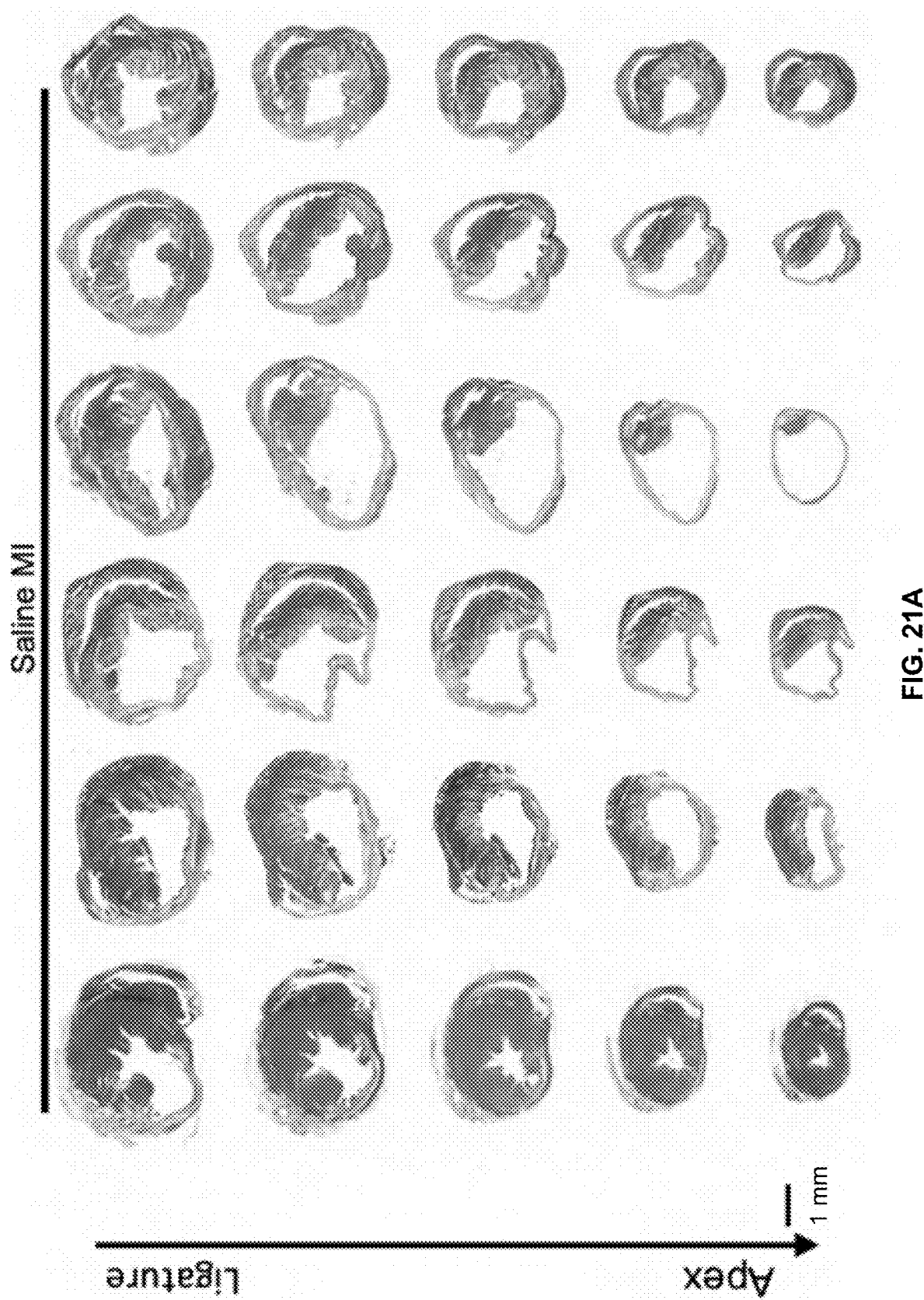
FIGS. 21A and 21B. Masson's trichrome-stained heart sections of saline-injected (FIG. 21A) or malonate-injected (FIG. 21B) mice at 1-week post-MI, hearts harvested at 6 weeks post-MI. Serial sections were cut from the site of the ligature to the apex. All hearts are shown.
Figure 21B:
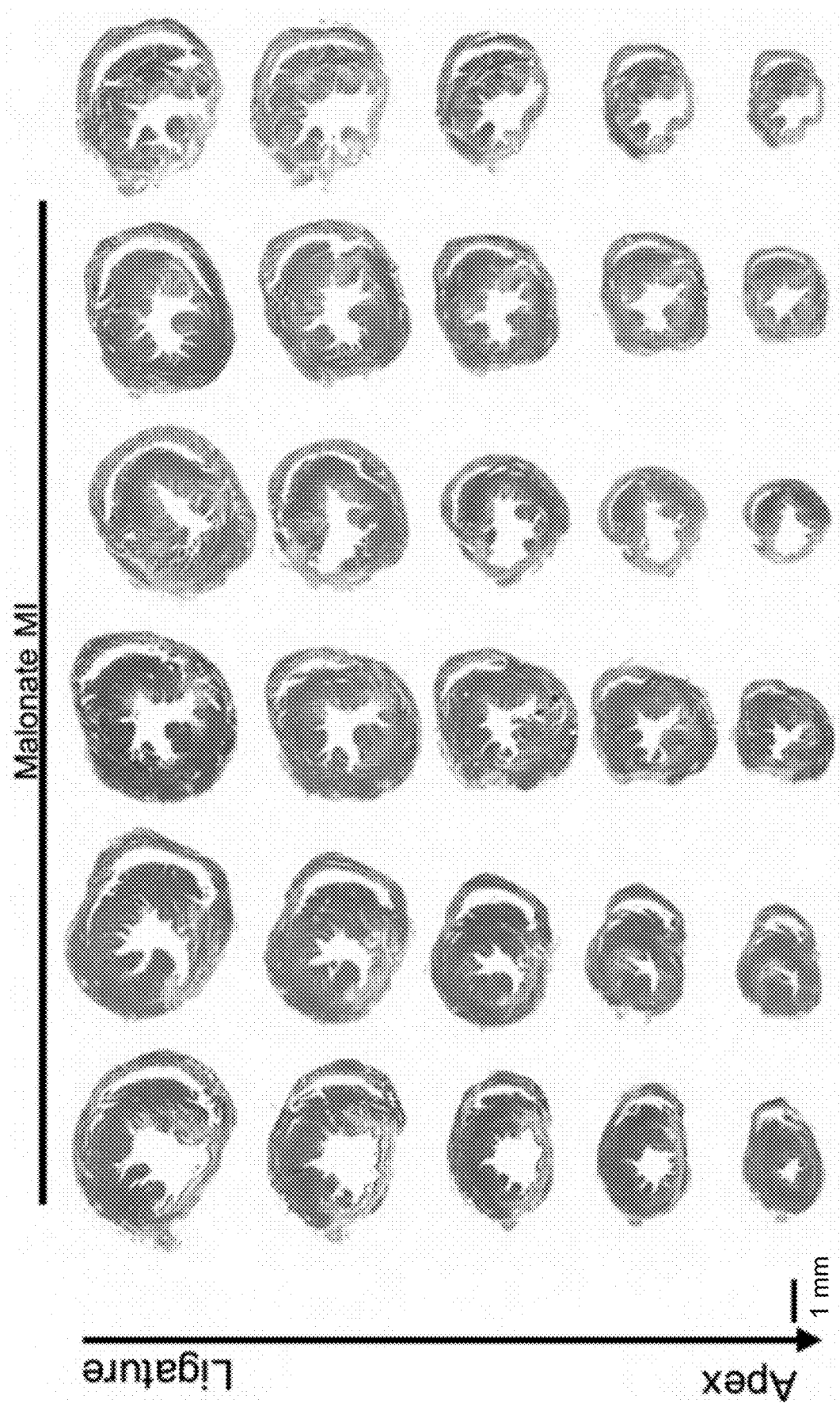

SDH Inhibitor Treatment at 1-Week Following Infarction Promotes Heart Regeneration To determine whether SDH inhibitors can promote a regenerative response following the establishment of infarction, we performed MI in 8-week-old mice and started malonate treatment at 1-week post-MI (FIG. 20A). The reduction of cardiac function was confirmed at 1-week post-MI by echocardiography (FIG. 20D). Mice were then randomized and treated with saline or malonate for a period of 4 weeks, and hearts were harvested at 6 weeks post-MI (FIG. 20A). Trichrome staining at 6 weeks post-MI showed a remarkable increase in myocardial thickness with minimal fibrosis in malonate-treated mice (FIGS. 20B, 21A, and 21B). Fibrosis quantification demonstrated a significant reduction in scar size in the malonate-treated mice at 6 weeks post-MI (FIG. 20C). Remarkably, there was a significant increase in cardiac function in malonate-treated mice at 4-weeks and 6-weeks post-MI (FIGS. 20D, 21A, and 21B and Tables 5A and 5B). Our results demonstrate that injection of malonate in adult mice at 1-week post-MI promoted myocardial regeneration and functional improvement over time. Together, these results demonstrate that SDH inhibition by malonate can stimulate a cardiac regenerative response following the establishment of infarction in the adult heart.

TABLE 5A

The fundamental measured and calculated echocardiography parameters of adult mice hearts that were injected with saline at 1 WPMI.

| | Saline | | | | | |
|---|---|---|---|---|---|---|
| | Pre | 1 WPMI | 2 WPMI | 3 WPMI | 4 WPMI | 6 WPMI |
| Measurement | | | | | | |
| LVIDD (mm) | 3.138 ± 0.154 | 4.189 ± 0.154 | 4.250 ± 0.353 | 4.566 ± 0.245 | 4.798 ± 0.220 | 4.545 ± 0.312 |
| LVPWD (mm) | 0.700 ± 0.024 | 0.561 ± 0.039 | 0.658 ± 0.044 | 0.546 ± 0.047 | 0.607 ± 0.062 | 0.578 ± 0.057 |
| LVIDS (mm) | 2.006 ± 0.173 | 3.439 ± 0.161 | 3.323 ± 0.334 | 3.869 ± 0.295 | 4.131 ± 0.250 | 3.920 ± 0.269 |
| LVPWS (mm) | 0.853 ± 0.013 | 0.718 ± 0.047 | 0.812 ± 0.045 | 0.667 ± 0.050 | 0.718 ± 0.069 | 0.703 ± 0.057 |
| LVAWD (mm) | 0.677 ± 0.028 | 0.565 ± 0.065 | 0.611 ± 0.029 | 0.564 ± 0.025 | 0.569 ± 0.011 | 0.555 ± 0.039 |
| LVAWS (mm) | 0.857 ± 0.030 | 0.684 ± 0.062 | 0.762 ± 0.016 | 0.717 ± 0.044 | 0.697 ± 0.029 | 0.692 ± 0.048 |
| Calculation | | | | | | |
| LV Vol; d (µL) | 39.808 ± 4.551 | 78.918 ± 7.141 | 95.580 ± 13.317 | 97.723 ± 12.093 | 109.132 ± 11.921 | 97.210 ± 14.876 |
| LV Vol; s (µL) | 13.716 ± 2.538 | 49.688 ± 5.777 | 55.987 ± 8.117 | 67.669 ± 11.552 | 77.650 ± 11.346 | 68.658 ± 10.723 |
| % EF | 67.029 ± 3.787 | 37.429 ± 2.893 | 40.417 ± 3.841 | 32.782 ± 4.648 | 29.616 ± 3.741 | 29.293 ± 1.743 |
| % FS | 36.578 ± 3.085 | 17.952 ± 1.564 | 19.945 ± 2.179 | 15.690 ± 2.458 | 14.041 ± 1.879 | 13.706 ± 0.897 |
| LV Mass (mg) | 64.802 ± 5.942 | 81.465 ± 8.930 | 108.770 ± 19.267 | 94.096 ± 11.624 | 110.671 ± 14.454 | 97.743 ± 19.470 |
| HR (BPM) | 475.667 ± 30.650 | 486.000 ± 34.126 | 482.400 ± 23.784 | 493.167 ± 42.918 | 469.167 ± 31.183 | 450.200 ± 35.541 |

Notes.
LVIDD = Left Ventricle Internal Diameter Diastole. LVPWD = Left Ventricle Posterior Wall Thickness Diastole. LVIDS = Left Ventricle Internal Diameter Systole. LVPWS = Left Ventricle Posterior Wall Thickness Systole. LVAWD = Left Ventricle Anterior Wall Thickness Diastole. LVAWS = Left Ventricle Anterior Wall Thickness Systole. LV Vol; d = Left Ventricular Volume; diastole. LV Vol; s = Left Ventricular Volume; systole. % EF = Ejection Fraction. % FS = Fractional Shortening. LV Mass = Left Ventricular Mass (Anatomical Weight). HR = Heart Rate. Data are expressed as mean ± SE.

TABLE 5B

The fundamental measured and calculated echocardiography parameters of adult mice hearts that were injected with malonate at 1 WPMI.

| | Malonate | | | | | |
|---|---|---|---|---|---|---|
| | Pre | 1 WPMI | 2 WPMI | 3 WPMI | 4 WPMI | 6 WPMI |
| Measurement | | | | | | |
| LVIDD (mm) | 2.872 ± 0.174 | 4.329 ± 0.343 | 4.458 ± 0.467 | 4.139 ± 0.296 | 4.136 ± 0.349 | 4.113 ± 0.228 |
| LVPWD (mm) | 0.717 ± 0.020 | 0.665 ± 0.033 | 0.671 ± 0.023 | 0.613 ± 0.017 | 0.962 ± 0.287 | 0.738 ± 0.018 |
| LVIDS (mm) | 1.779 ± 0.158 | 3.603 ± 0.326 | 3.772 ± 0.497 | 3.393 ± 0.326 | 2.958 ± 0.419 | 3.146 ± 0.214 |
| LVPWS (mm) | 0.829 ± 0.017 | 0.838 ± 0.025 | 0.814 ± 0.012 | 0.764 ± 0.018 | 1.015 ± 0.214 | 0.846 ± 0.017 |
| LVAWD (mm) | 0.704 ± 0.023 | 0.651 ± 0.018 | 0.698 ± 0.021 | 0.623 ± 0.024 | 0.687 ± 0.039 | 0.718 ± 0.011 |
| LVAWS (mm) | 0.838 ± 0.024 | 0.788 ± 0.016 | 0.833 ± 0.016 | 0.791 ± 0.028 | 0.809 ± 0.051 | 0.831 ± 0.019 |
| Calculation | | | | | | |
| LV Vol; d (µL) | 32.452 ± 4.967 | 87.566 ± 16.492 | 97.776 ± 23.854 | 78.984 ± 13.627 | 70.697 ± 15.089 | 75.865 ± 9.652 |
| LV Vol; s (µL) | 10.208 ± 2.260 | 57.371 ± 11.845 | 69.099 ± 20.899 | 50.781 ± 11.724 | 47.342 ± 10.954 | 40.253 ± 6.696 |
| % EF | 69.832 ± 3.238 | 35.760 ± 3.523 | 34.537 ± 4.592 | 38.518 ± 3.865 | 45.375 ± 5.597 | 47.208 ± 4.087 |
| % FS | 38.447 ± 2.452 | 17.077 ± 1.873 | 16.507 ± 2.337 | 18.642 ± 2.058 | 24.529 ± 3.624 | 23.535 ± 2.509 |
| LV Mass (mg) | 59.124 ± 6.101 | 105.118 ± 13.726 | 118.559 ± 20.724 | 90.090 ± 11.827 | 90.726 ± 13.717 | 107.845 ± 11.076 |
| HR (BPM) | 481.167 ± 53.447 | 462.600 ± 26.250 | 540.500 ± 33.895 | 486.500 ± 19.347 | 456.833 ± 40.940 | 465.000 ± 18.925 |

Notes.
LVIDD = Left Ventricle Internal Diameter Diastole. LVPWD = Left Ventricle Posterior Wall Thickness Diastole. LVIDS = Left Ventricle Internal Diameter Systole. LVPWS = Left Ventricle Posterior Wall Thickness Systole. LVAWD = Left Ventricle Anterior Wall Thickness Diastole. LVAWS = Left Ventricle Anterior Wall Thickness Systole. LV Vol; d = Left Ventricular Volume; diastole. LV Vol; s = Left Ventricular Volume; systole. % EF = Ejection Fraction. % FS = Fractional Shortening. LV Mass = Left Ventricular Mass (Anatomical Weight). HR = Heart Rate. Data are expressed as mean ± SE.

Discussion

Systolic heart failure often occurs as a consequence of the inability of the adult mammalian heart to regenerate following injury such as MI. Models of mammalian endogenous heart regeneration provide an opportunity to identify new approaches to restore adult human heart regeneration[29]. Lineage tracing studies demonstrated that proliferation of the pre-existing cardiomyocytes is the main source of the newly formed functional myocardium during endogenous regeneration. Thus, stimulating adult cardiomyocyte proliferation represents an important target towards regenerating the adult human heart following injury.

The metabolic switch in energy utilization of the postnatal heart and the subsequent increase in ROS production has emerged as an important factor in loss of this regenerative response[6]. The mechanisms that regulate this metabolic switch remain unclear. In this study, our results demonstrate a powerful link in succinate metabolism and succinate dehydrogenase (SDH) activity to the regenerative response of the mammalian heart. We demonstrate that high levels of succinate can induce cardiomyocyte DNA damage and inhibit cardiomyocyte proliferation and regeneration. More importantly, we demonstrate that inhibition of SDH activity by malonate and other SDH inhibitors can also restore a cardiac regenerative response in the adult heart by stimulating adult cardiomyocyte cell cycle re-entry and revascularization, important hallmarks of endogenous heart regeneration. This regenerative effect is largely due to SDH inhibition, since Atpenin A5, a potent inhibitor of SDH, can recapitulate the regenerative effect of malonate. More importantly, our metabolite analysis demonstrates that SDH inhibition promotes a dynamic metabolic shift from oxidative phosphorylation to glycolysis in the adult heart. This metabolic switch from aerobic respiration to glycolysis is in line with previous studies defining SDH as a tumor suppressor, where SDH mutations result in a metabolic reprogramming to glycolysis that promotes cancer growth[13-15].

Malonate has been demonstrated to play a cardioprotective role in reperfusion injury by inhibiting reverse activity of SDH, which prevents succinate accumulation and the subsequent redox insult and cardiac damage[7]. Interestingly, SDH inhibition by malonate for 2 weeks increased succinate levels, a consequence of inhibition of oxidative phosphorylation[22-24]. In contrast to reperfusion injury, our results demonstrate that malonate does not exhibit a cardioprotective role following myocardial infarction. The progression in restoration of cardiac structure and function over time strongly suggests a stimulation of a regenerative response by malonate following infarction, rather than protection. Furthermore, we demonstrate that malonate treatment starting 1-week post-MI promotes myocardial regeneration and functional improvement over time. Collectively, these results reveal a novel role for SDH in its ability to metabolically reprogram the adult heart to a regenerative state. This underscores the translational potential of SDH inhibition as a powerful metabolic target for promoting adult heart regeneration.

There is an emerging appreciation for the role of metabolism in controlling cell state. Adult neural stem cell activity changes from a quiescent to a proliferative state via a metabolic shift by a single metabolite[30]. Similarly, metabolic reprogramming regulates macrophage function in response to different stimuli[31,32]. Interestingly, a recent study demonstrated that metabolic reprogramming is required for cardiomyocyte proliferation during zebrafish heart regeneration[16]. The potential metabolic targeting of multiple cell types by systemic administration of malonate explains the striking regenerative effect following adult myocardial infarction. In this study, we demonstrate that SDH inhibition promotes adult cardiomyocyte proliferation and revascularization following injury. The overall impact of malonate on other cell types will need to be further investigated. For example, SDH inhibition by malonate has been shown to promote an anti-inflammatory state of macrophages following lipopolysaccharide stimulation[33]. Thus, whether SDH inhibition regulates the inflammatory response following infarction remains unclear. In addition, mutations in SDH have been shown to promote DNA methylation, demonstrating an interplay between epigenetics and metabolism[14, 22, 34]. Whether SDH inhibition by malonate can modulate the epigenetic landscape and the transcriptional activity of multiple cardiac cell types needs to be determined.

The effects of SDH inhibitors shown herein can be translated to the clinic for treatment of heart failure. The SDH inhibitors can be systemically delivered, but targeted delivery to the heart would avoid any off-target effects from systemic SDH inhibition. SDH inhibition plays a role in multiple cancers, so the regenerative effect of SDH inhibitors shown herein provides an unexpected therapeutic role for these agents. Malonate and other SDH inhibitors provide an opportunity for transient SDH inhibition. Promoting adult heart regeneration by SDH inhibition has enormous implications for treatment of systolic heart failure patients.

Example 2 References

1. Virani S S, Alonso A, Benjamin E J, Bittencourt M S, Callaway C W, Carson A P, Chamberlain A M, Chang A R, Cheng S, Delling F N, Djousse L, Elkind M S V, Ferguson J F, Fornage M, Khan S S, Kissela B M, Knutson K L, Kwan T W, Lackland D T, Lewis T T, Lichtman J H, Longenecker C T, Loop M S, Lutsey P L, Martin S S, Matsushita K, Moran A E, Mussolino M E, Perak A M, Rosamond W D, Roth G A, Sampson U K A, Satou G M, Schroeder E B, Shah S H, Shay C M, Spartano N L, Stokes A, Tirschwell D L, VanWagner L B, Tsao C W, American Heart Association Council on E, Prevention Statistics C and Stroke Statistics S. Heart Disease and Stroke Statistics-2020 Update: A Report From the American Heart Association. *Circulation.* 2020; 141:e139-e596.
2. Mahmoud A I, Porrello E R, Kimura W, Olson E N and Sadek H A. Surgical models for cardiac regeneration in neonatal mice. *Nature protocols.* 2014; 9:305-11.
3. Porrello E R, Mahmoud A I, Simpson E, Hill J A, Richardson J A, Olson E N and Sadek H A. Transient regenerative potential of the neonatal mouse heart. *Science.* 2011; 331:1078-80.
4. Porrello E R, Mahmoud A I, Simpson E, Johnson B A, Grinsfelder D, Canseco D,
Mammen P P, Rothermel B A, Olson E N and Sadek H A. Regulation of neonatal and adult mammalian heart regeneration by the miR-15 family. *Proceedings of the National Academy of Sciences of the United States of America.* 2013; 110:187-92.
5. Webster W S and Abela D. The effect of hypoxia in development. *Birth Defects Res C Embryo Today.* 2007; 81:215-28.
6. Puente B N, Kimura W, Muralidhar S A, Moon J, Amatruda J F, Phelps K L, Grinsfelder D, Rothermel B A, Chen R, Garcia J A, Santos C X, Thet S, Mori E, Kinter M T, Rindler P M, Zacchigna S, Mukherjee S, Chen D J, Mahmoud A I, Giacca M, Rabinovitch P S, Aroumougame A, Shah A M, Szweda L I and Sadek H A. The oxygen-rich postnatal environment induces cardiomyocyte cell-cycle arrest through DNA damage response. *Cell.* 2014; 157:565-79.

7. Chouchani E T, Pell V R, Gaude E, Aksentijevic D, Sundier S Y, Robb E L, Logan A, Nadtochiy S M, Ord E N J, Smith A C, Eyassu F, Shirley R, Hu C H, Dare A J, James A M, Rogatti S, Hartley R C, Eaton S, Costa A S H, Brookes P S, Davidson S M, Duchen M R, Saeb-Parsy K, Shattock M J, Robinson A J, Work L M, Frezza C, Krieg T and Murphy M P. Ischaemic accumulation of succinate controls reperfusion injury through mitochondrial ROS. *Nature.* 2014; 515:431-435.

8. Hochachka P W and Dressendorfer R H. Succinate accumulation in man during exercise. *Eur J Appl Physiol Occup Physiol.* 1976; 35:235-42.

9. Zhang J, Wang Y T, Miller J H, Day M M, Munger J C and Brookes P S. Accumulation of Succinate in Cardiac Ischemia Primarily Occurs via Canonical Krebs Cycle Activity. *Cell Rep.* 2018; 23:2617-2628.

10. King A, Selak M A and Gottlieb E. Succinate dehydrogenase and fumarate hydratase: linking mitochondrial dysfunction and cancer. *Oncogene.* 2006; 25:4675-82.

11. Kula-Alwar D, Prag H A and Krieg T. Targeting Succinate Metabolism in Ischemia/Reperfusion Injury. *Circulation.* 2019; 140:1968-1970.

12. Valls-Lacalle L, Barba I, Miro-Casas E, Ruiz-Meana M, Rodriguez-Sinovas A and Garcia-Dorado D. Selective Inhibition of Succinate Dehydrogenase in Reperfused Myocardium with Intracoronary Malonate Reduces Infarct Size. *Sci Rep.* 2018; 8:2442.

13. Gottlieb E and Tomlinson I P. Mitochondrial tumour suppressors: a genetic and biochemical update. *Nat Rev Cancer.* 2005; 5:857-66.

14. Her Y F and Maher L J, 3rd. Succinate Dehydrogenase Loss in Familial Paraganglioma: Biochemistry, Genetics, and Epigenetics. *Int J Endocrinol.* 2015; 2015:296167.

15. Tseng P L, Wu W H, Hu T H, Chen C W, Cheng H C, Li C F, Tsai W H, Tsai H J, Hsieh M C, Chuang J H and Chang W T. Decreased succinate dehydrogenase B in human hepatocellular carcinoma accelerates tumor malignancy by inducing the Warburg effect. *Sci Rep.* 2018; 8:3081.

16. Honkoop H, de Bakker D E, Aharonov A, Kruse F, Shakked A, Nguyen P D, de Heus C, Garric L, Muraro M J, Shoffner A, Tessadori F, Peterson J C, Noort W, Bertozzi A, Weidinger G, Posthuma G, Grun D, van der Laarse W J, Klumperman J, Jaspers R T, Poss K D, van Oudenaarden A, Tzahor E and Bakkers J. Single-cell analysis uncovers that metabolic reprogramming by ErbB2 signaling is essential for cardiomyocyte proliferation in the regenerating heart. *Elife.* 2019; 8.

17. Kumar D, Hacker T A, Buck J, Whitesell L F, Kaji E H, Douglas P S and Kamp T J. Distinct mouse coronary anatomy and myocardial infarction consequent to ligation. *Coron Artery Dis.* 2005; 16:41-4.

18. Singla D K, Hacker T A, Ma L, Douglas P S, Sullivan R, Lyons G E and Kamp T J. Transplantation of embryonic stem cells into the infarcted mouse heart: formation of multiple cell types. *J Mol Cell Cardiol.* 2006; 40:195-200.

19. Harris S P, Bartley C R, Hacker T A, McDonald K S, Douglas P S, greater M L, Powers P A and Moss R L. Hypertrophic cardiomyopathy in cardiac myosin binding protein-C knockout mice. *Circ Res.* 2002; 90:594-601.

20. Mahmoud A I, Kocabas F, Muralidhar S A, Kimura W, Koura A S, Thet S, Porrello E R and Sadek H A. Meis1 regulates postnatal cardiomyocyte cell cycle arrest. *Nature.* 2013; 497:249-253.

21. Miyadera H, Shiomi K, Ui H, Yamaguchi Y, Masuma R, Tomoda H, Miyoshi H, Osanai A, Kita K and Omura S. Atpenins, potent and specific inhibitors of mitochondrial complex II (succinate-ubiquinone oxidoreductase). *Proceedings of the National Academy of Sciences of the United States of America.* 2003; 100:473-7.

22. Letouze E, Martinelli C, Loriot C, Burnichon N, Abermil N, Ottolenghi C, Janin M, Menara M, Nguyen A T, Benit P, Buffet A, Marcaillou C, Bertherat J, Amar L, Rustin P, De Reynies A, Gimenez-Roqueplo A P and Favier J. SDH mutations establish a hypermethylator phenotype in paraganglioma. *Cancer Cell.* 2013; 23:739-52.

23. Pollard P J, Briere J J, Alam N A, Barwell J, Barclay E, Wortham N C, Hunt T, Mitchell M, Olpin S, Moat S J, Hargreaves I P, Heales S J, Chung Y L, Griffiths J R, Dalgleish A, McGrath J A, Gleeson M J, Hodgson S V, Poulsom R, Rustin P and Tomlinson I P. Accumulation of Krebs cycle intermediates and over-expression of HIF1alpha in tumours which result from germline F H and SDH mutations. *Hum Mol Genet.* 2005; 14:2231-9.

24. Sciacovelli M, Guzzo G, Morello V, Frezza C, Zheng L, Nannini N, Calabrese F, Laudiero G, Esposito F, Landriscina M, Defilippi P, Bernardi P and Rasola A. The mitochondrial chaperone TRAP1 promotes neoplastic growth by inhibiting succinate dehydrogenase. *Cell Metab.* 2013; 17:988-999.

25. Bryant D M, O'Meara C C, Ho N N, Gannon J, Cai L and Lee R T. A systematic analysis of neonatal mouse heart regeneration after apical resection. *J Mol Cell Cardiol.* 2015; 79:315-8.

26. Das S, Goldstone A B, Wang H, Farry J, D'Amato G, Paulsen M J, Eskandari A, Hironaka C E, Phansalkar R, Sharma B, Rhee S, Shamskhou E A, Agalliu D, de Jesus Perez V, Woo Y J and Red-Horse K. A Unique Collateral Artery Development Program Promotes Neonatal Heart Regeneration. *Cell.* 2019; 176:1128-1142 e18.

27. De Bock K, Georgiadou M, Schoors S, Kuchnio A, Wong B W, Cantelmo A R, Quaegebeur A, Ghesquiere B, Cauwenberghs S, Eelen G, Phng L K, Betz I, Tembuyser B, Brepoels K, Welti J, Geudens I, Segura I, Cruys B, Bifari F, Decimo I, Blanco R, Wyns S, Vangindertael J, Rocha S, Collins R T, Munck S, Daelemans D, Imamura H, Devlieger R, Rider M, Van Veldhoven P P, Schuit F, Bartrons R, Hofkens J, Fraisl P, Telang S, Deberardinis R J, Schoonjans L, Vinckier S, Chesney J, Gerhardt H, Dewerchin M and Carmeliet P. Role of PFKFB3-driven glycolysis in vessel sprouting. *Cell.* 2013; 154:651-63.

28. Eelen G, de Zeeuw P, Simons M and Carmeliet P. Endothelial cell metabolism in normal and diseased vasculature. *Circ Res.* 2015; 116:1231-44.

29. Sadek H and Olson E N. Toward the Goal of Human Heart Regeneration. *Cell Stem Cell.* 2020; 26:7-16.

30. Knobloch M, Pilz G A, Ghesquiere B, Kovacs W J, Wegleiter T, Moore D L, Hruzova M, Zamboni N, Carmeliet P and Jessberger S. A Fatty Acid Oxidation-Dependent Metabolic Shift Regulates Adult Neural Stem Cell Activity. *Cell Rep.* 2017; 20:2144-2155.

31. Kelly B and O'Neill L A. Metabolic reprogramming in macrophages and dendritic cells in innate immunity. *Cell Res.* 2015; 25:771-84.

32. Seim G L, Britt E C, John S V, Yeo F J, Johnson A R, Eisenstein R S, Pagliarini D J and Fan J. Two-stage metabolic remodelling in macrophages in response to lipopolysaccharide and interferon-γ stimulation. *Nature Metabolism.* 2019; 1:731-742.
33. Mills E L, Kelly B, Logan A, Costa A S H, Varma M, Bryant C E, Tourlomousis P, Dabritz J H M, Gottlieb E, Latorre I, Corr S C, McManus G, Ryan D, Jacobs H T, Szibor M, Xavier R J, Braun T, Frezza C, Murphy M P and O'Neill L A. Succinate Dehydrogenase Supports Metabolic Repurposing of Mitochondria to Drive Inflammatory Macrophages. *Cell.* 2016; 167:457-470 e13.
34. Kaelin W G, Jr. and McKnight S L. Influence of metabolism on epigenetics and disease. *Cell.* 2013; 153: 56-69.

We claim:

1. A method of improving cardiac structure and/or function in a subject, the method comprising administering a succinate dehydrogenase inhibitor to the subject starting at least 90 minutes after a cardiac event selected from the group consisting of cardiac ischemia, cardiac ischemia-reperfusion, myocardial infarction, and any combination thereof, wherein the succinate dehydrogenase inhibitor is administered in an amount and for a time effective to elicit an improvement in cardiac structure and/or function.

2. The method of claim 1, wherein the subject has a myocardial lesion.

3. The method of claim 1, wherein the subject has a myocardial lesion selected from the group consisting of fibrosis, decreased myocardial thickness, a myocardial infarct, and any combination thereof.

4. The method of claim 1, wherein the subject has a myocardial infarct.

5. The method of claim 1, wherein the administering comprises administering the succinate dehydrogenase inhibitor to the subject over a period of time after the cardiac event.

6. The method of claim 5, wherein the period of time comprises a point in time at least 90 minutes after the cardiac event.

7. The method of claim 5, wherein the period of time spans at least 24 hours.

8. The method of claim 5, wherein the succinate dehydrogenase inhibitor is intermittently administered to the subject over the period of time.

9. The method of claim 1, wherein the succinate dehydrogenase inhibitor is administered in an amount and for a time effective to elicit an improvement in cardiac function.

10. The method of claim 1, wherein the succinate dehydrogenase inhibitor is administered in an amount and for a time effective to elicit an improvement in cardiac function selected from the group consisting of an increase in cardiomyocyte proliferation, an increase in ejection fraction, an increase in fractional shortening, a decrease in left ventricle internal diameter diastole, a decrease in left ventricle internal diameter systole, and any combination thereof.

11. The method of claim 1, wherein the succinate dehydrogenase inhibitor is administered in an amount and for a time effective to elicit an improvement in cardiac structure.

12. The method of claim 11, wherein the improvement in cardiac structure occurs in an infarcted zone in the heart.

13. The method of claim 1, wherein the succinate dehydrogenase inhibitor is administered in an amount and for a time effective to elicit an improvement in cardiac structure selected from the group consisting of decreased fibrosis, an increase in myocardial thickness, an increase in coronary artery formation, an increase in capillary density, an increase in revascularization, a decrease in myocardial lesion size, and any combination thereof.

14. The method of claim 13, wherein the improvement in cardiac structure occurs in an infarcted zone in the heart.

15. The method of claim 1, wherein the succinate dehydrogenase inhibitor comprises a succinate-analog inhibitor.

16. The method of claim 15, wherein the succinate-analog inhibitor comprises a malonate compound.

17. The method of claim 1, wherein the succinate dehydrogenase inhibitor comprises a ubiquinone-type inhibitor.

18. The method of claim 17, wherein the ubiquinone-type inhibitor comprises an atpenin.

19. The method of claim 1, wherein:
the subject has a myocardial lesion;
the succinate dehydrogenase inhibitor is administered in an amount and for a time effective to elicit an improvement selected from the group consisting of an improvement in cardiac function and an improvement in cardiac structure, wherein:
  the improvement in cardiac function is selected from the group consisting of an increase in cardiomyocyte proliferation, an increase in ejection fraction, an increase in fractional shortening, a decrease in left ventricle internal diameter diastole, a decrease in left ventricle internal diameter systole, and any combination thereof; and
  the improvement in cardiac structure is selected from the group consisting of decreased fibrosis, an increase in myocardial thickness, an increase in coronary artery formation, an increase in capillary density, an increase in revascularization, a decrease in myocardial lesion size, and any combination thereof; and
the succinate dehydrogenase inhibitor is administered to the subject over a period of time spanning at least two weeks after the cardiac event.

* * * * *